US010272149B2

(12) United States Patent
Wentworth et al.

(10) Patent No.: US 10,272,149 B2
(45) Date of Patent: Apr. 30, 2019

(54) MODIFIED BAT INFLUENZA VIRUSES AND THEIR USES

(71) Applicants: Kansas State University Research Foundation, Manhattan, KS (US); David Wentworth, Decatur, GA (US); Bin Zhou, Albany, NY (US)

(72) Inventors: David Wentworth, Decatur, GA (US); Bin Zhou, Albany, NY (US); Wenjun Ma, Manhattan, KS (US); Jingjiao Ma, Manhattan, KS (US)

(73) Assignees: KANSAS STATE UNIVERSITY RESEARCH FOUNDATION, Manhattan, KS (US); J. CRAIG VENTER INSTITUTE, Rockville, MD (US)

( * ) Notice: Subject to any disclaimer, the term of this patent is extended or adjusted under 35 U.S.C. 154(b) by 0 days.

(21) Appl. No.: 15/508,670

(22) PCT Filed: Sep. 4, 2015

(86) PCT No.: PCT/US2015/048648

§ 371 (c)(1),
(2) Date: Mar. 3, 2017

(87) PCT Pub. No.: WO2016/037113

PCT Pub. Date: Mar. 10, 2016

(65) Prior Publication Data

US 2017/0274064 A1 Sep. 28, 2017

Related U.S. Application Data

(60) Provisional application No. 62/046,528, filed on Sep. 5, 2014.

(51) Int. Cl.

| | |
|---|---|
| ***A61K 39/145*** | (2006.01) |
| ***G01N 30/02*** | (2006.01) |
| ***C12N 15/09*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *C12N 15/09* (2013.01); *G01N 30/02* (2013.01); *A61K 2039/5254* (2013.01); *C12N 2760/16134* (2013.01)

(58) Field of Classification Search

None

See application file for complete search history.

(56) References Cited

FOREIGN PATENT DOCUMENTS

EP 2170382 7/2013

OTHER PUBLICATIONS

Juozapaitis et al. (Nature, Jul. 23, 2014, p. 1-9 in IDS on Mar. 3, 2017.*
Juozapatitis et al. (Nature, Jul. 23, 2014, p. 1-8).*
Tong et al. (PNAS, 2012, vol. 109, p. 4269-4274).*
Tong et al. (PLOS, 2013, vol. 9, p. 1-12).*
Zhou et al. (PLOS, Oct. 2014, vol. 10, p. 1-18).*
International Search Report and Written Opinion dated Feb. 9, 2016, in PCT/US15/48648, filed in Sep. 4, 2015.
Juozapaitis, Mindaugas "An infectious bat-derived chimeric influenza virus harbouring the entry machinery of an influenza A virus," Nature Communications, Jul. 23, 2014.
GenBank: CY103881.1 Influenza A virus (A/little yellow-shouldered bat/Guatemala/164/2009(H17N10) polymerase PB2(PB2) gene, complete cds, 2012.
GenBank: CY103882.1 Influenza A virus (A/little yellow-shouldered bat/Guatemala/164/2009(H17N10) polymerase PB1(PB1) gene, complete cds, 2012.
GenBank: CY103883.1 Influenza A virus (A/little yellow-shouldered bat/Guatemala/164/2009(H17N10) polymerase PA (PA) gene, complete cds, 2012.
GenBank: CY103885.1 Influenza A virus (A/little yellow-shouldered bat/Guatemala/164/2009(H17N10) polymerase NP gene, complete cds, 2012.
GenBank: CY103887.1 Influenza A virus (A/little yellow-shouldered bat/Guatemala/164/2009(H17N10) polymerase 2 (M2) and matrix protein 1 (M1) genes, complete cds, 2012.
GenBank: CY103888.1 Influenza A virus (A/little yellow-shouldered bat/Guatemala/164/2009(H17N10) nonstructural protein 2 (NS2) and nonstructural protein 1 (NS1) genes, complete cds, 2012.
GenBank: CY103884.1 Influenza A virus (A/little yellow-shouldered bat/Guatemala/164/2009(H17N10)) hemagglutinin (HA) gene complete cds, 2012.
GenBank: CY103886.1 Influenza A virus (A/little yellow-shouldered bat/Guatemala/164/2009(H17N10)) neuraminidase (NA) gene, complete cds, 2012.
Tong, Suxiang, "New World Bats Harbor Diverse Influenza A Viruses," PLOS Pathogens, Oct. 2013, vol. 8, Issue 10.
Dormitzer, Philip, "Synthetic Generation of Influenza Vaccine Viruses for Rapid Response to Pandemics," Science Translational Medicine, May 15, 2013, vol. 5, Issue 185.
Influenza Strain Details for A/little yellow-shouldered bat/Guatemala/164/2009 (H17N10) (2012).
Influenza Strain Details for A/flat-faced bat/Peru/033/2010(H18N11) (2013).
Influenza Strain Details for A/swine/Texas/4199-2/1998(H3N2) (2011).

* cited by examiner

*Primary Examiner* — Agnieszka Boesen
(74) *Attorney, Agent, or Firm* — Hovey Williams LLP

(57) ABSTRACT

Vaccine compositions useful for vaccination against a target influenza strain, and method and kits for using the same. The vaccines comprise a live attenuated influenza virus that is synthetically constructed based upon a backbone platform derived from a bat influenza strain, and heterologous surface proteins HA and NA derived from the target influenza strain. The live attenuated virus is non-reassortant with native, circulating influenza strains, and can be used to create vaccines for humans and other animals.

18 Claims, 25 Drawing Sheets

Specification includes a Sequence Listing.

SEQUENCE LISTING

```
<160> NUMBER OF SEQ ID NOS: 52

<210> SEQ ID NO 1
<211> LENGTH: 259
<212> TYPE: DNA
<213> ORGANISM: Influenza A virus
<220> FEATURE:
<221> NAME/KEY: misc_feature
<222> LOCATION: (1)..(259)
<223> OTHER INFORMATION: Synthetic cDNA construct encoding for chimeric
      hemagglutinin based on the hemagglutinin packaging sequence of bat
      H17N10
<220> FEATURE:
<221> NAME/KEY: misc_feature
<222> LOCATION: (1)..(34)
<223> OTHER INFORMATION: Noncoding region
<220> FEATURE:
<221> NAME/KEY: mutation
<222> LOCATION: (35)..(37)
<223> OTHER INFORMATION: ATG start codon mutated to GTG
<220> FEATURE:
<221> NAME/KEY: misc_feature
<222> LOCATION: (38)..(204)
<223> OTHER INFORMATION: Hemagglutinin coding region
<220> FEATURE:
<221> NAME/KEY: misc_feature
<222> LOCATION: (96)..(96)
<223> OTHER INFORMATION: N is A, T, C, or G, position of insertion of
      open reading frame sequence encoding heterologous hemagglutinin
<220> FEATURE:
<221> NAME/KEY: misc_feature
<222> LOCATION: (205)..(259)
<223> OTHER INFORMATION: Noncoding region

<400> SEQUENCE: 1

agcagaagca gggtcactat tactctgtgc tactgtggag ctgattgtcc tactaatcct      60

tctcaatcct tatactttg tattagggga cagaanactc tgtattctac cattgcatca      120

tccgtcgtgc ttggctcgtt gataatagcc gcttttcttt gggggtgcca aaaaggctca     180

atccaatgta aaatatgtat atagaacggt ggaattaacc ttgtcattca gaaaagcaaa     240

aaagaccctt gtttctact                                                  259


<210> SEQ ID NO 2
<211> LENGTH: 402
<212> TYPE: DNA
<213> ORGANISM: Influenza A virus
<220> FEATURE:
<221> NAME/KEY: misc_feature
<222> LOCATION: (1)..(402)
<223> OTHER INFORMATION: Synthetic cDNA construct encoding for chimeric
      neuraminidase based on the neuraminidase packaging sequence of bat
      H17N10
<220> FEATURE:
<221> NAME/KEY: misc_feature
<222> LOCATION: (1)..(23)
<223> OTHER INFORMATION: Noncoding region
<220> FEATURE:
```

-continued

<221> NAME/KEY: mutation
<222> LOCATION: (24)..(26)
<223> OTHER INFORMATION: ATG start codon mutated to CTG
<220> FEATURE:
<221> NAME/KEY: misc_feature
<222> LOCATION: (27)..(364)
<223> OTHER INFORMATION: Neuraminidase coding region
<220> FEATURE:
<221> NAME/KEY: misc_feature
<222> LOCATION: (207)..(207)
<223> OTHER INFORMATION: N is A, T, C, or G, insertion point for open
reading frame encoding for heterologous neuraminidase
<220> FEATURE:
<221> NAME/KEY: misc_feature
<222> LOCATION: (365)..(402)
<223> OTHER INFORMATION: Noncoding region

<400> SEQUENCE: 2

```
agcagaagca ggagttttta atactgtcta tcaacggaac gacctgtcta ctcacactca     60

gtctaatact cactgttata ctgatagggc tccaaatcct gctgcccttt attcttttct    120

ggaccaacag ccccccgcca gaaatctcca acagcactag ctgctgcaac ggaacctttc    180

tgactgaaac aaacaacaat ataaccnatt ctttcaaccc aaaggagacc tcatttctgg    240

atgccaacga atctgtttct ggctggaaat agaagatcaa acagtaggcc taggaatgat    300

tcaagaactc agcactttct gtgggataaa ctcacctgtt cagaatataa attgggattc    360

atgaccaatg gacagcgaat gaaaaaactc cttgtttcta ct                       402
```

<210> SEQ ID NO 3
<211> LENGTH: 264
<212> TYPE: DNA
<213> ORGANISM: Influenza A virus
<220> FEATURE:
<221> NAME/KEY: misc_feature
<222> LOCATION: (1)..(264)
<223> OTHER INFORMATION: Synthetic cDNA construct encoding for chimeric
hemagglutinin based on the hemagglutinin packaging sequence of bat
H18N11
<220> FEATURE:
<221> NAME/KEY: misc_feature
<222> LOCATION: (1)..(28)
<223> OTHER INFORMATION: Noncoding region
<220> FEATURE:
<221> NAME/KEY: mutation
<222> LOCATION: (29)..(31)
<223> OTHER INFORMATION: ATG start codon mutated to GTG
<220> FEATURE:
<221> NAME/KEY: misc_feature
<222> LOCATION: (32)..(207)
<223> OTHER INFORMATION: Hemagglutinin coding region
<220> FEATURE:
<221> NAME/KEY: misc_feature
<222> LOCATION: (90)..(90)
<223> OTHER INFORMATION: N is A, T, C, or G, insertion point for open
reading frame encoding for heterologous hemagglutinin
<220> FEATURE:
<221> NAME/KEY: misc_feature
<222> LOCATION: (208)..(264)
<223> OTHER INFORMATION: Noncoding region

<400> SEQUENCE: 3

```
agcagaagca gggtgattat tattcagagt gattacaata cttatcttgg tactccctat     60

tgttgtaggt gaccaaatat gcattggaan gtgcattaaa tcatttactc aacagtggca    120

agttcagtag tgcttggctt gattatacta gccgcaattg aatggggctg ttttaaaggg    180

aacctgcaat gcagaatatg tatttgaggc tgtggtgtta gctaatgtca atctattatt    240

gcaaaaaaca cccttgtttc tact                                           264
```

<210> SEQ ID NO 4
<211> LENGTH: 420
<212> TYPE: DNA
<213> ORGANISM: Influenza A virus
<220> FEATURE:
<221> NAME/KEY: misc_feature
<222> LOCATION: (1)..(420)
<223> OTHER INFORMATION: Synthetic cDNA construct encoding for chimeric neuraminidase based on the neutaminidase packaging sequence of bat H18N11
<220> FEATURE:
<221> NAME/KEY: misc_feature
<222> LOCATION: (1)..(23)
<223> OTHER INFORMATION: Noncoding region
<220> FEATURE:
<221> NAME/KEY: mutation
<222> LOCATION: (24)..(26)
<223> OTHER INFORMATION: ATG start codon mutated to CTG
<220> FEATURE:
<221> NAME/KEY: misc_feature
<222> LOCATION: (27)..(361)
<223> OTHER INFORMATION: Neuraminidase coding region
<220> FEATURE:
<221> NAME/KEY: misc_feature
<222> LOCATION: (207)..(207)
<223> OTHER INFORMATION: N is A, T, C, or G, insertion point for open reading frame encoding for heterologous neuraminidase
<220> FEATURE:
<221> NAME/KEY: misc_feature
<222> LOCATION: (362)..(420)
<223> OTHER INFORMATION: Noncoding region

<400> SEQUENCE: 4
agcagaagca ggagtttttc atactgtcgt ttcaaacatc gacatgtctg ttgattgttt 60
ccctaatatg tgggatacta acagtctgcc ttcaggtact gttacccttc atattgatat 120
ggacaaatac agaaccaaat tattcctgtg agtgtccagc tcccaacatc agtcttagct 180
gtccaaacgg gacttctgta acatatnagg cctgtatcag cctgcttatg aatcacgtga 240
ttgtcaagag ttgtgttttt ggattgaaat tgctgcaact accaaagcag gcttgtcatc 300
caatgatctg attacttttt gtgggacagg aggctcaatg ccagatgtca actgggggta 360
agtatatgat tacattcata ttttaaatgg atgtataaga aaaaactcct tgtttctact 420

<210> SEQ ID NO 5
<211> LENGTH: 2338
<212> TYPE: DNA
<213> ORGANISM: Influenza A virus
<220> FEATURE:
<221> NAME/KEY: misc_feature
<222> LOCATION: (1)..(2338)
<223> OTHER INFORMATION: Synthetic cDNA construct encoding for H17N10 PB2

<400> SEQUENCE: 5
agcagaagca ggtcagagat tgtcaatatg gagagaatca aagaattact agaaatggtc 60
aaaaattccc gcatgaggga aattttaaca accaccagcg ttgaccatat ggcagtaatc 120
aagaaataca ccagtgggag gcaggagaaa aaccctgcac tacgaatgaa atggatgatg 180
gccatgaaat acccaataag tgcctcctca cgaatcagag aaatgatacc agagaaagac 240
gaagacggaa acacactctg gaccaacacc aaagacgctg ggagtaaccg cgttcttgtt 300
tcccctaacg cagtcacatg gtggaacaga gctgggccag tgtccgacgt tgtgcactat 360
ccacgtgttt acaagatgta ttttgacaga ctggagagac taacccatgg gacatttgga 420
ccggtaaaat tctacaatca ggtgaaagta aggaaaagag tagacatcaa tccgggacac 480
aaagacctca cctccagaga ggcacaagaa gtcattatgg aagtggtgtt cccaaatgaa 540

-continued

```
gtcggagcaa ggacgctgtc ctctgacgct caattgacaa taaccaagga aaaaaaggaa     600

gagctgaaga actgcaaaat atcacctata atggttgcat acatgctgga aagggaacta     660

gtcagaagaa cgagatttct tccaatagca ggggcaactt caagcactta tgttgaggtc     720

ttacatttga cacaaggaac ctgctgggag caacagtaca ctccaggagg ggaagctgag     780

aatgatgatc ttgatcagac attaataatt gcatcaagaa acatagttag aagatcaata     840

gtagcaatag atcctcttgc ctcattacta tccatgtgtc acacaacgag tatatcttca     900

gagcccttag ttgaaattct tcgatccaac ccaactgatg agcaagcagt gaacatttgc     960

aaagccgctc tgggaattag aataaacaac agttttagtt ttgggggata caattttaag    1020

agggttaaag gaagctccca gagaacagaa aaagcagtgc taactggaaa tcttcaaact    1080

ttaaccatga caatatttga gggatatgaa gagtttaacg tttcgggtaa aagggcctct    1140

gccgttttaa agaaaggaac ccaacggctc atccaagcta taataggagg gagaacattg    1200

gaggacattt taaatttaat gattacacta atggtatttt ctcaggaaga aaaaatgctc    1260

aaagcagtaa gaggtgatct aaacttcgta aatagagcca accaaaggct aaacccaatg    1320

tatcaactcc ttaggcattt ccaaaaggac tcaagtactc tattaaggaa ttgggggact    1380

gaagaaatag accctataat gggaatagct ggtataatgc ctgatgggac gatcaataaa    1440

aaccaaacac ttataggagt caggctcagc caagggggtg tggatgagta ctctttcaat    1500

gaaagaatca gagtcaacat agacaaatat ctaagagtaa gaaatgaaaa gggagaactt    1560

ctcatcagcc ctgaggaagt cagtgaggcc cagggtcagg aaaaactccc aattaactac    1620

aactcttcct taatgtggga agtaaacgga ccagagtcca tcctcactaa cacctaccat    1680

tggataataa aaaactggga gctgctgaag acccaatgga tgaccgatcc aacagtctta    1740

tacaacagga tggaatttga gccatttcaa actttaatcc ctaaagggaa tcgggctacc    1800

tacagtggtt ttaccaggac tcttttccaa caaatgaggg atgtcgaagg aacatttgat    1860

agcatacaag taataaaact gctcccgttc tcagcccatc ctccctcttt gggaaggacc    1920

caattcagct cctttacact gaacataaga ggagcaccct taagactgct aataaggga     1980

aactctcagg tctttaacta caaccagatg gaaaatgtaa tcattgtctt ggggaagagt    2040

gttgggagtc ccgaaaggtc catactaact gaaagcagca gcattgaatc tgcggtattg    2100

agaggattcc tgatcttagg gaaagccaat agcaaatatg gacccgtgct aacaattggg    2160

gagctggaca aactagggcg gggagaaaaa gccaatgtcc tcataggaca aggggacaca    2220

gtgttggtca tgaaacgaaa aagagactct agcatactta ctgatagcca gacagccctc    2280

aaaagaattc gtttggagga gtcgaagtaa caatactaaa aatgaccttg tttctact      2338

<210> SEQ ID NO 6
<211> LENGTH: 2339
<212> TYPE: DNA
<213> ORGANISM: Influenza A virus
<220> FEATURE:
<221> NAME/KEY: misc_feature
<222> LOCATION: (1)..(2339)
<223> OTHER INFORMATION: Synthetic cDNA construct encoding for H17N10
      PB1

<400> SEQUENCE: 6

agcagaagca ggcaaactat tttaaaatgg acgtcaatcc gatgctaata ttcctgaaag      60

tcccagtgca aaatgccata agcacaacct ttccctacac cggggaccca ccgtacagcc     120

atggaacggg gactggctac acaatggaca cggtaatcag gactcatgat tactcatccc     180
```

-continued

```
gaggaatatg gaaaaccaac tctgaaacag gagctcagca actcaatcca atagatggac    240
ctcttcctga ggacaacgaa cctagcgggt atgcgcagac cgattgcgtg cttgaactga    300
tagaaaggct tgacagatca catcctggtc tctttgagac agcatgccag gaaaccattg    360
atgctatcca acaaacgaga gttgacaaac taacacaagg gagacagaca tatgactgga    420
cgctaaacag gaaccaaccg gccgccactg cactagccaa caccatcgag gtcttcagaa    480
aaaatggcca caagttaaat gagtcagggc ggctaattga ctttttgaaa gatgtcctac    540
tttcctttga aaataattct atggaagtga ccacacattt ccagaagaaa aaacgaataa    600
gggataacca cacaaagaaa atgattaccc aaagaacgat tgggaagaaa agggtaaaat    660
taactaagaa aaattaccta ataagggcac tgaccctaaa tacaatgacc aaggacgcag    720
agagaggtaa actaaaaaga agggccatag caaccccccgg gatgcaaatt agagggtttg   780
tttatttcgt cgagctactt gcgagaaaca tttgtgaaag acttgagcaa tcaggcttac    840
cagtaggggg gaacgaaaag aaagctaaac ttgcgaatgt tataaagaaa atgatggcca    900
aatccacgga tgaagaacta tcatacacca taacaggaga caatactaag tggaatgaga    960
accaaaatcc aagaatcttt ctagccatgg ttttaaaaat cacggcagga caaccggaat   1020
ggttcagaga cttattagca gttgctccca tcatgttttc caacaaagtt gcccgactag   1080
ggagaggcta tatgttcgaa agcaaatcta tgcatttaag aacccaaatt tccgcagaga   1140
acctgagtga catcaactta cgttatttta atgaagacac aaaaaagaaa atagagaaaa   1200
ttaggcacct tatggtggag ggaacagcat cacttagccc agggatgatg atgggaatgt   1260
tcaatatgct tagtacagta ctaggggtta gtgtcttgaa tttaggccaa agggagattt   1320
tgaaaagaac atattggtgg gatggcctcc agtcatcaga tgattttgca ttaattatta   1380
atggtcactt caaagaagat atccagcagg gagtcaacca cttctaccga acttgcaaat   1440
tagtagggat caacatgtca cagaaaaaat catatataaa taaaactggc acttttgaat   1500
ttacaagctt cttctacaga tatggcttcg ttgccaactt ctccatggag ttgccctcct   1560
ttggtgtagc ggggaacaac gaatcagcag acatgagcat aggaacaaca gtaatcaaaa   1620
ccaacatgat caacaatgat ctggggcccg ccacagcaca aatggcaatc cagcttttta   1680
taaaagatta tagatataca taccgatgcc acaggggga cacgaatcta gaaacaagaa   1740
gaacaaaaag catcaaacga ctctggactg agacaatctc aaaagctggg ctcctagtcg   1800
ctgatggggg ccccaacccc tacaatctta gaaacctgca cataccagaa gtctgtttaa   1860
aatgggacct aatggatcct gattatagag gaagactctg caaccccaac aaccccttg   1920
ttcaccatat ggaagtggaa agcactaatc ttgcagttgt catgccagcc cacgggccag   1980
ccaaatccct agaatacgac gcagtggcaa ccacacattc atggactccc aaaagaaatc   2040
ggtcaatcct aaacacaaat caaagaggaa ttctagaaga cgagaaaatt tatcaaaaat   2100
gctgccagat atttgaaaag tttttcccta gttcaactta tagaagacct atcggaatgg   2160
ccagcatgct agatgcaatg ctgtcaagag caagaataga tgcaagaata gacctggagt   2220
ctggaagaat cagcagccaa gatttctccg agataacgaa tacctgcaag gcgatcgaag   2280
cattgaaacg ccaataaggg tcattagttg ttgaaacgaa aaaatgcctt gtttctact    2339
```

<210> SEQ ID NO 7
<211> LENGTH: 2216
<212> TYPE: DNA
<213> ORGANISM: Influenza A virus
<220> FEATURE:
<221> NAME/KEY: misc_feature
<222> LOCATION: (1)..(2216)
<223> OTHER INFORMATION: Synthetic cDNA construct encoding for H17N10 PA

<400> SEQUENCE: 7
agcagaagca ggtacttaaa caatggagaa tttcgtgaga actaacttca atcccatgat 60
actagaaagg gctgaaaaaa ctatgaaaga atatggagaa aacccccaga atgagggaaa 120
caaatttgca gcaatatcta cacacatgga ggtatgtttc atgtattcag acttccactt 180
cattgacctt gaagggaata caatagtaaa ggaaagtgat gacgacaatg caatgctaaa 240
gcaccggttt gagataatcg aaggccaaga gagaaacatc gcatggacaa ttgtcaattc 300
aatttgcaac atgacagaaa atagcaaacc acgattccta cctgatcttt acgactacaa 360
aaccaacaaa ttcattgaaa tcggggtaac aaggagaaaa gttgaggact attattatga 420
aaaggccagt aaactgaaag gtgaaaatgt atatattcac atcttctcct ttgatggaga 480
agagatggcc acagatgatg agtatatact tgacgaagaa agcagagctc gaataaaaac 540
tcgactcttt gttcttagac aagaactagc cacagctggg ctctgggatt cctttcgcca 600
atcagagaag ggagaagaaa cactggagga ggaattttca tacccccaa cattccagag 660 gcttgcaaac cagagcctac ctccatcatt caaggactat caccaattca aagcgtacgt 720
gtcgagtttc aaagcaaacg gcaacataga ggctaaacta ggggcaatgt cagaagaggt 780
taacgcacaa atagagaact ttgaccccag gacaataagg gagctggagc tccccgaggg 840
aaaatcctgc actcaaagaa gcaaattcct gctaatggac gcaatgaaac tgtcggtttt 900
aaacccggca catgaagggg aaggaatccc aatgaaagac gccaaagctt gtcttgacac 960
cttctgggga tggaaaaaag ccacagttat caaaaagcat gaaaagggag tcaacactaa 1020
ctatctcatg atctgggagc agctcttaga atcaataaaa gaagtagagg gaaaattcct 1080
caacttaagg aaaaccaatc atctcaagtg ggggctggga gaagggcaag cgcccgaaaa 1140
gatggacttt gaagattgta aagaagtccc tgatctcttc caatacaaaa gtgaaccccc 1200
tgaaaagcga aaattggcca gctggatcca aagtgaattc aacaaagctt ctgagctcac 1260
aaactcaaac tggattgaat ttgatgagtt gggaaatgac gtggcaccca tcgagcacat 1320
tgccagtaga agaagaaatt tcttcaccgc agaggtatct caatgcagag cctcagaata 1380
tataatgaaa gcggtgtaca taaatacagc ccttcttaac tcctcatgca cggcaatgga 1440
ggaatatcag gtgatcccaa taatcaccaa atgtagagac acatcaggtc agagaaggac 1500
caatttatat gggttcatca tcaaaggtcg atctcacctt aggaatgata ctgatgttgt 1560
aaacttcatt tctttggagt tttcactgac cgatccccga aatgagattc ataagtggga 1620
gaaatactgc gtactagaga ttggagacat ggagattcgg acatcaataa gtacaataat 1680
gaaaccggtc tacctctata ttaggaccaa tggaacttca aaaatcaaaa tgaaatgggg 1740
aatggaaatg agaagatgct tactccaatc tctacaacaa gtggaaagca tgattgaagc 1800
agaatcagca gtcaaagaga aggatatgac tgaacccttc tttagaaatc gggaaaatga 1860
ctggccaata ggagagaagcc ctcaaggaat agagaaagga acgataggaa aagtatgcag 1920
ggttttactc gctaaatctg ttttcaacag catttatgcc tcagctcagc ttgaaggatt 1980
ttcagcagaa tcgagaaaat tactgttact cattcaagca tttagagata atttagatcc 2040
tggaactttt gacttgaaag ggctgtacga agccattgag gaatgcatca ttaatgatcc 2100
ttgggtcctt ttaaatgctt catggttcaa ctccttcctt aaagcagtac aattgagcat 2160
gtgaagaact ctatcagctt tgattcaatg taagaaaaaa gtaccttgtt tctact 2216

-continued

<210> SEQ ID NO 8
<211> LENGTH: 1558
<212> TYPE: DNA
<213> ORGANISM: Influenza A virus
<220> FEATURE:
<221> NAME/KEY: misc_feature
<222> LOCATION: (1)..(1558)
<223> OTHER INFORMATION: Synthetic cDNA construct encoding for H17N10 NP

<400> SEQUENCE: 8
agcagaagca gggttaataa tcacattgtg acatttaaag atgacaactc aaggccttaa 60
acgcaccttc gagcaaatgg agactgactc caaacagagc accactgaaa tcagatccgc 120
agtcggaaga atggtgaaag caattgggaa attctacatc caaatgtgtg cagaaatgaa 180
attagatgac aaggagggag ccctgatcca gaacagcata acaattgaaa ggatggcact 240
ctcagcattc gacgagagaa gaaataaata cttagaagag caccccactg tggggaaaga 300
ccccaagaag acaggtgggc ccatctacag gagaaaagat ggaaaatggg agagagagat 360
ggccctcatg gaaaaggaaa acatccgagc aatatggaaa atggctaatg aaggagagga 420
gaatctatct ggtctaagcc atattatgat ctggcactca aacttaaatg acacaaccta 480
tcagcgaaca agagcccttg tcagaacagg aatggaccca aggatgtgct cgttgatgca 540
gggctcaact cttccaagaa gagctggagc agctgggact gcagtcaaag gagtggggac 600
cctcataatg gagttgatcc ggatgatcaa aagaggaatg aatgacagaa atttctggaa 660
gggtgaacaa gggagaagaa ctcgaacagc ttatgaaagg ctctgtggaa acctgaaagg 720
aaagtttcaa acagccccac agaaagcaat ggttgatcaa gtcaaagaag gaaaaaaccc 780
aggaaatgca gaaatagagg acttactatt tcttgcaaga tctgccctga tcctccgagg 840
agcagtagct cataagtcag ctctcccagc ctgtgtatat ggtcttgggg tcgccagagg 900
gtttgacttt gaaaaagagg gatactctct agtaggcaga gacccctact tgctcctgca 960
gaactcccag attttctcca tcctgagaaa gggggagaac gctgcacaca aaagtcagct 1020
agtgtggatg gcctgccatg ctgcagcctt tgaggacata aggatcagca gctttatcaa 1080
gggaagcaaa ataatccctc ggggcaagct agaaacaaga ggattacaaa ttgctggctc 1140
tgaaagtcta gatgaaatcc tggtaatcag cttggacctc aaaagtcatt attgggcaat 1200
caaaactagg agtgggggta atccccaaca atcaagaagc acagctggtc aaatagcggt 1260
gcaacctacc ttttccgtcc aaagaaatat cccctttgag aaaaagacga tcatggcggc 1320
cttctcaaca accgaagaag ggagaatcac agacatgagg actgaaataa tcagacttat 1380
ggaaaactca gacccaaagg agaaagtctt catagggcga ggcgtcttcg agatgggaga 1440
cgagaaggca actaacccga tagtgcctcc actagatggg aatgacgagg gttcttattt 1500
ctttggagac aaggcagacg agttcgacat ttgagcaaaa aatacccttg tttctact 1558

<210> SEQ ID NO 9
<211> LENGTH: 497
<212> TYPE: PRT
<213> ORGANISM: Influenza A virus
<220> FEATURE:
<221> NAME/KEY: MISC_FEATURE
<222> LOCATION: (1)..(497)
<223> OTHER INFORMATION: H17N10 NP viral protein

<400> SEQUENCE: 9

Met Thr Thr Gln Gly Leu Lys Arg Thr Phe Glu Gln Met Glu Thr Asp
1 5 10 15

-continued

```
Ser Lys Gln Ser Thr Thr Glu Ile Arg Ser Ala Val Gly Arg Met Val
            20                  25                  30

Lys Ala Ile Gly Lys Phe Tyr Ile Gln Met Cys Ala Glu Met Lys Leu
        35                  40                  45

Asp Asp Lys Glu Gly Ala Leu Ile Gln Asn Ser Ile Thr Ile Glu Arg
    50                  55                  60

Met Ala Leu Ser Ala Phe Asp Glu Arg Arg Asn Lys Tyr Leu Glu Glu
65                  70                  75                  80

His Pro Thr Val Gly Lys Asp Pro Lys Lys Thr Gly Gly Pro Ile Tyr
                85                  90                  95

Arg Arg Lys Asp Gly Lys Trp Glu Arg Glu Met Ala Leu Met Glu Lys
            100                 105                 110

Glu Asn Ile Arg Ala Ile Trp Lys Met Ala Asn Glu Gly Glu Glu Asn
        115                 120                 125

Leu Ser Gly Leu Ser His Ile Met Ile Trp His Ser Asn Leu Asn Asp
    130                 135                 140

Thr Thr Tyr Gln Arg Thr Arg Ala Leu Val Arg Thr Gly Met Asp Pro
145                 150                 155                 160

Arg Met Cys Ser Leu Met Gln Gly Ser Thr Leu Pro Arg Arg Ala Gly
                165                 170                 175

Ala Ala Gly Thr Ala Val Lys Gly Val Gly Thr Leu Ile Met Glu Leu
            180                 185                 190

Ile Arg Met Ile Lys Arg Gly Met Asn Asp Arg Asn Phe Trp Lys Gly
        195                 200                 205

Glu Gln Gly Arg Arg Thr Arg Thr Ala Tyr Glu Arg Leu Cys Gly Asn
    210                 215                 220

Leu Lys Gly Lys Phe Gln Thr Ala Pro Gln Lys Ala Met Val Asp Gln
225                 230                 235                 240

Val Lys Glu Gly Lys Asn Pro Gly Asn Ala Glu Ile Glu Asp Leu Leu
                245                 250                 255

Phe Leu Ala Arg Ser Ala Leu Ile Leu Arg Gly Ala Val Ala His Lys
            260                 265                 270

Ser Ala Leu Pro Ala Cys Val Tyr Gly Leu Gly Val Ala Arg Gly Phe
        275                 280                 285

Asp Phe Glu Lys Glu Gly Tyr Ser Leu Val Gly Arg Asp Pro Tyr Leu
    290                 295                 300

Leu Leu Gln Asn Ser Gln Ile Phe Ser Ile Leu Arg Lys Gly Glu Asn
305                 310                 315                 320

Ala Ala His Lys Ser Gln Leu Val Trp Met Ala Cys His Ala Ala Ala
                325                 330                 335

Phe Glu Asp Ile Arg Ile Ser Ser Phe Ile Lys Gly Ser Lys Ile Ile
            340                 345                 350

Pro Arg Gly Lys Leu Glu Thr Arg Gly Leu Gln Ile Ala Gly Ser Glu
        355                 360                 365

Ser Leu Asp Glu Ile Leu Val Ile Ser Leu Asp Leu Lys Ser His Tyr
    370                 375                 380

Trp Ala Ile Lys Thr Arg Ser Gly Gly Asn Pro Gln Gln Ser Arg Ser
385                 390                 395                 400

Thr Ala Gly Gln Ile Ala Val Gln Pro Thr Phe Ser Val Gln Arg Asn
                405                 410                 415

Ile Pro Phe Glu Lys Lys Thr Ile Met Ala Ala Phe Ser Thr Thr Glu
            420                 425                 430

Glu Gly Arg Ile Thr Asp Met Arg Thr Glu Ile Ile Arg Leu Met Glu
```

```
        435                 440                 445

Asn Ser Asp Pro Lys Glu Lys Val Phe Ile Gly Arg Gly Val Phe Glu
    450                 455                 460

Met Gly Asp Glu Lys Ala Thr Asn Pro Ile Val Pro Pro Leu Asp Gly
465                 470                 475                 480

Asn Asp Glu Gly Ser Tyr Phe Phe Gly Asp Lys Ala Asp Glu Phe Asp
                485                 490                 495

Ile


<210> SEQ ID NO 10
<211> LENGTH: 1027
<212> TYPE: DNA
<213> ORGANISM: Influenza A virus
<220> FEATURE:
<221> NAME/KEY: misc_feature
<222> LOCATION: (1)..(1027)
<223> OTHER INFORMATION: Synthetic cDNA construct encoding for H17N10 M

<400> SEQUENCE: 10

agcagaagca ggcattatcc aaaatgagca tcttaacaga ggttgaaacg tacgttctat     60

caatcatccc atcagggcct ctaaaagctg acatagccca aaagctcgag gatgtcttct    120

caggccgaaa cagcgacctg gacaccttat tagaatggct aaaggccaga cccatactgt    180

ccccattaac aaagggaatt gtcggctttg ttttcacact cacagtgcca tgtgagaagg    240

gcgcccctag acggaaattc atacaaacgg ccctcaatgg aaatggagag gcggccaata    300

tggacaaggc agttaaaatc tacaaaaagt tgaaaaagga gataactttc catggggcca    360

aggaagtggc actaagctac ccaactgggg cattagcatg ctgcatgggg ctcatctaca    420

atagaatggg atctgtgaca accgaagtgg catttggctt agtctgtgct acttgtgagc    480

acattgccga ttctcaatat agatctcatc ggcagatgat aagctcgaca aatcccctga    540

tcagacatga aaacagaatg gcaacggcag caagcactgc aaaggccatg gaacaaatgg    600

ctagcagtag cgaacaagct gctgaagcaa tggaaattgc ttcacaggcc aggcaaatga    660

ttcaagcaat gagggctatc gggacccacc caacaacttc cagtgggctt aaagacgatc    720

tccttgataa tctacaggcc taccagaaga gaatgggaat ccaaatgcag aggtttaaat    780

gaagacttga tcctggcggc caacataatt ggaatccttc atctggcact ctggattata    840

gacagatggc tatacagcta tagtctagca ttatatcagc agatacggag ccactgggta    900

attagaactg tcgattccac aagggaacta agagaagaat ttaaagaaga acacacggca    960

attgaaaatc cggaccctat catagtaatc atggaaaagt gaaatgaaaa aatgccttgt   1020

ttctact                                                              1027


<210> SEQ ID NO 11
<211> LENGTH: 96
<212> TYPE: PRT
<213> ORGANISM: Influenza A virus
<220> FEATURE:
<221> NAME/KEY: MISC_FEATURE
<222> LOCATION: (1)..(96)
<223> OTHER INFORMATION: H17N10  M2 viral protein

<400> SEQUENCE: 11

Met Ser Ile Leu Thr Glu Val Glu Thr Pro Thr Arg Arg Glu Trp Glu
1               5                   10                  15

Ser Lys Cys Arg Gly Leu Asn Glu Asp Leu Ile Leu Ala Ala Asn Ile
            20                  25                  30
```

```
Ile Gly Ile Leu His Leu Ala Leu Trp Ile Ile Asp Arg Trp Leu Tyr
        35                  40                  45

Ser Tyr Ser Leu Ala Leu Tyr Gln Gln Ile Arg Ser His Trp Val Ile
    50                  55                  60

Arg Thr Val Asp Ser Thr Arg Glu Leu Arg Glu Glu Phe Lys Glu Glu
65                  70                  75                  80

His Thr Ala Ile Glu Asn Pro Asp Pro Ile Ile Val Ile Met Glu Lys
                85                  90                  95


<210> SEQ ID NO 12
<211> LENGTH: 252
<212> TYPE: PRT
<213> ORGANISM: Influenza A virus
<220> FEATURE:
<221> NAME/KEY: MISC_FEATURE
<222> LOCATION: (1)..(252)
<223> OTHER INFORMATION: H17N10  M1 viral protein

<400> SEQUENCE: 12

Met Ser Ile Leu Thr Glu Val Glu Thr Tyr Val Leu Ser Ile Ile Pro
1               5                   10                  15

Ser Gly Pro Leu Lys Ala Asp Ile Ala Gln Lys Leu Glu Asp Val Phe
            20                  25                  30

Ser Gly Arg Asn Ser Asp Leu Asp Thr Leu Leu Glu Trp Leu Lys Ala
        35                  40                  45

Arg Pro Ile Leu Ser Pro Leu Thr Lys Gly Ile Val Gly Phe Val Phe
    50                  55                  60

Thr Leu Thr Val Pro Cys Glu Lys Gly Ala Pro Arg Arg Lys Phe Ile
65                  70                  75                  80

Gln Thr Ala Leu Asn Gly Asn Gly Glu Ala Ala Asn Met Asp Lys Ala
                85                  90                  95

Val Lys Ile Tyr Lys Lys Leu Lys Lys Glu Ile Thr Phe His Gly Ala
            100                 105                 110

Lys Glu Val Ala Leu Ser Tyr Pro Thr Gly Ala Leu Ala Cys Cys Met
        115                 120                 125

Gly Leu Ile Tyr Asn Arg Met Gly Ser Val Thr Thr Glu Val Ala Phe
    130                 135                 140

Gly Leu Val Cys Ala Thr Cys Glu His Ile Ala Asp Ser Gln Tyr Arg
145                 150                 155                 160

Ser His Arg Gln Met Ile Ser Ser Thr Asn Pro Leu Ile Arg His Glu
                165                 170                 175

Asn Arg Met Ala Thr Ala Ala Ser Thr Ala Lys Ala Met Glu Gln Met
            180                 185                 190

Ala Ser Ser Ser Glu Gln Ala Ala Glu Ala Met Glu Ile Ala Ser Gln
        195                 200                 205

Ala Arg Gln Met Ile Gln Ala Met Arg Ala Ile Gly Thr His Pro Thr
    210                 215                 220

Thr Ser Ser Gly Leu Lys Asp Asp Leu Leu Asp Asn Leu Gln Ala Tyr
225                 230                 235                 240

Gln Lys Arg Met Gly Ile Gln Met Gln Arg Phe Lys
                245                 250


<210> SEQ ID NO 13
<211> LENGTH: 895
<212> TYPE: DNA
<213> ORGANISM: Influenza A virus
<220> FEATURE:
<221> NAME/KEY: misc_feature
```

<222> LOCATION: (1)..(895)
<223> OTHER INFORMATION: Synthetic cDNA construct encoding for H17N10 NS

<400> SEQUENCE: 13
agcagaagca gggtatctaa agacataatg gaaccaaacc cgacaactat cgcatttcag 60
gtagactgtt atctatggca cctgaaaaag acgcttagca tgatgggaga ggttgacgcc 120
ccgttcgagg accgactccg aagagaacag aaagcactga aaggaaggag catgactctg 180
gggatagaca ttcaatcagc aacccaagaa gggtactaca agatcaagtc tatcacagaa 240
gaaagcatgc cctcctatgg aatactacca aatgcaggac aaaacgaacc caaatatata 300
acagagatga ctcaagagga aacaatcaga aactgggtga tgatccaacc taagcaaaag 360
gttatctccg ggaggatctt gatcagcatg gaccaagcag taaccaataa agtcttaaca 420
ataaaggcaa atttcactgt ctgctttgga aaactagaaa ggcttgtatt agctagagct 480
ttcacagaag aagggacagt agtgggtgaa atcaaccctc tgtcttttgt tacaggacat 540
actggagagg atgtcaaaac tgcatatgaa ctcttcagaa gtggatttga atggaatgat 600
aacacaattg acgaatctca gattctacag agactcgcta ggggagtcat taatgagaac 660
cggagactac cgcaagatgg ctcaacagaa taacaattgg agactccaat taggggagaa 720
attaacaatt attagaaatc taattcaaac gtgccgggag gtgctaatga cctcatctaa 780
cagttttgta gagataacct tcctcgctgc acttgacctc ttattggagg tcgaaagaga 840
aatgagaacc ttggcttttc agctgatatg attaaaaaat acccttgttt ctact 895

<210> SEQ ID NO 14
<211> LENGTH: 221
<212> TYPE: PRT
<213> ORGANISM: Influenza A virus
<220> FEATURE:
<221> NAME/KEY: MISC_FEATURE
<222> LOCATION: (1)..(221)
<223> OTHER INFORMATION: H17N10 NS1 viral protein

<400> SEQUENCE: 14

Met Glu Pro Asn Pro Thr Thr Ile Ala Phe Gln Val Asp Cys Tyr Leu
1               5                   10                  15

Trp His Leu Lys Lys Thr Leu Ser Met Met Gly Glu Val Asp Ala Pro
            20                  25                  30

Phe Glu Asp Arg Leu Arg Arg Glu Gln Lys Ala Leu Lys Gly Arg Ser
        35                  40                  45

Met Thr Leu Gly Ile Asp Ile Gln Ser Ala Thr Gln Glu Gly Tyr Tyr
    50                  55                  60

Lys Ile Lys Ser Ile Thr Glu Glu Ser Met Pro Ser Tyr Gly Ile Leu
65                  70                  75                  80

Pro Asn Ala Gly Gln Asn Glu Pro Lys Tyr Ile Thr Glu Met Thr Gln
                85                  90                  95

Glu Glu Thr Ile Arg Asn Trp Val Met Ile Gln Pro Lys Gln Lys Val
            100                 105                 110

Ile Ser Gly Arg Ile Leu Ile Ser Met Asp Gln Ala Val Thr Asn Lys
        115                 120                 125

Val Leu Thr Ile Lys Ala Asn Phe Thr Val Cys Phe Gly Lys Leu Glu
    130                 135                 140

Arg Leu Val Leu Ala Arg Ala Phe Thr Glu Glu Gly Thr Val Val Gly
145                 150                 155                 160

Glu Ile Asn Pro Leu Ser Phe Val Thr Gly His Thr Gly Glu Asp Val
                165                 170                 175

```
Lys Thr Ala Tyr Glu Leu Phe Arg Ser Gly Phe Glu Trp Asn Asp Asn
            180                 185                 190

Thr Ile Asp Glu Ser Gln Ile Leu Gln Arg Leu Ala Arg Gly Val Ile
        195                 200                 205

Asn Glu Asn Arg Arg Leu Pro Gln Asp Gly Ser Thr Glu
    210                 215                 220


<210> SEQ ID NO 15
<211> LENGTH: 849
<212> TYPE: DNA
<213> ORGANISM: Influenza A virus
<220> FEATURE:
<221> NAME/KEY: misc_feature
<222> LOCATION: (1)..(849)
<223> OTHER INFORMATION: Synthetic cDNA construct encoding for H17N10 NS
      with a truncated Ns1 (NS1-128)

<400> SEQUENCE: 15

agcagaagca gggtatctaa agacataatg gaaccaaacc cgacaactat cgcatttcag      60

gtagactgtt atctatggca cctgaaaaag acgcttagca tgatgggaga ggttgacgcc     120

ccgttcgagg accgactccg aagagaacag aaagcactga aaggaaggag catgactctg     180

gggatagaca ttcaatcagc aacccaagaa gggtactaca agatcaagtc tatcacagaa     240

gaaagcatgc cctcctatgg aatactacca aatgcaggac aaaacgaacc caaatatata     300

acagagatga ctcaagagga aacaatcaga aactgggtga tgatccaacc taagcaaaag     360

gttatctccg ggaggatctt gatcagcatg gaccaagcag taaccaataa ataatagtga     420

ctaagtaaag agctttcaca gaagaaggga cagtagtggg tgaaatcaac cctctgtctt     480

ttgttacagg acatactgga gaggatgtca aaactgcata tgaactcttc agaagtggat     540

ttgaatggaa tgataacaca attgacgaat ctcagattct acagagactc gctaggggag     600

tcattaatga gaaccggaga ctaccgcaag atggctcaac agaataacaa ttggagactc     660

caattagggg agaaattaac aattattaga aatctaattc aaacgtgccg ggaggtgcta     720

atgacctcat ctaacagttt tgtagagata accttcctcg ctgcacttga cctcttattg     780

gaggtcgaaa gagaaatgag aaccttggct tttcagctga tatgattaaa aaataccctt     840

gtttctact                                                             849


<210> SEQ ID NO 16
<211> LENGTH: 684
<212> TYPE: DNA
<213> ORGANISM: Influenza A virus
<220> FEATURE:
<221> NAME/KEY: misc_feature
<222> LOCATION: (1)..(684)
<223> OTHER INFORMATION: Synthetic cDNA construct encoding for H17N10 NS
      with a truncated NS1 (NS1-73)

<400> SEQUENCE: 16

agcagaagca gggtatctaa agacataatg gaaccaaacc cgacaactat cgcatttcag      60

gtagactgtt atctatggca cctgaaaaag acgcttagca tgatgggaga ggttgacgcc     120

ccgttcgagg accgactccg aagagaacag aaagcactga aaggaaggag catgactctg     180

gggatagaca ttcaatcagc aacccaagaa gggtactaca agatcaagtc tatcacagaa     240

gaaagctaat agtgactaag taaagagctt tcacagaaga agggacagta gtgggtgaaa     300

tcaaccctct gtcttttgtt acaggacata ctggagagga tgtcaaaact gcatatgaac     360

tcttcagaag tggatttgaa tggaatgata acacaattga cgaatctcag attctacaga     420
```

```
gactcgctag gggagtcatt aatgagaacc ggagactacc gcaagatggc tcaacagaat    480

aacaattgga gactccaatt aggggagaaa ttaacaatta ttagaaatct aattcaaacg    540

tgccgggagg tgctaatgac ctcatctaac agttttgtag agataacctt cctcgctgca    600

cttgacctct tattggaggt cgaaagagaa atgagaacct tggcttttca gctgatatga    660

ttaaaaaata cccttgtttc tact                                           684


<210> SEQ ID NO 17
<211> LENGTH: 2367
<212> TYPE: DNA
<213> ORGANISM: Influenza A virus
<220> FEATURE:
<221> NAME/KEY: misc_feature
<222> LOCATION: (1)..(2367)
<223> OTHER INFORMATION: Synthetic cDNA construct encoding for H18N11
      PB2

<400> SEQUENCE: 17

tattcgtctc agggagcaga agcaggtcaa agattgtcaa aatggatcgc ataaaagaac     60

tactagaaat gacaaaaaat tcccgcatga gggaaatttt atcgacaaca agtgtcgacc    120

atatggcggt aatcagaaaa tacacaagtg ggagacaaga gaaaaacccg gcactaagaa    180

tgaaatggat gatggcaatg aaatttccaa taagtgcatc agccaaaata aaagaattaa    240

taccagaaaa ggatgaagat ggaaacgtat tgtggacaaa cacaaaggat gccgggagta    300

acagattact tgtttcacca aatgccgtga cttggtggaa tagagctgga ccaatctcag    360

aagttgtaca ttatcctaaa gtctacaaga tgtattttga tagacttgat cggttacaaa    420

atggaacata tggaccagtg aaattttaca accaaatgaa aataagaaag agagttgata    480

taaatcccgg gcacaaggat ttgacatcaa aagaagctca ggatgtaata atggaagttg    540

tctttccgaa tgaagtggga gcaagaacat tatcatcaga tgcacaatta gcgatcacca    600

aggagaaaaa acaagagttg cagaactgca aaatctctcc aattatggtt gcatacatgc    660

ttgaaaggga actagtacga aaaacaaggt tcctaccagt tgcaggggca acctcaagca    720

ctcatgttga agttttacac ctaacccaag gcacatgttg ggagcaacaa tatacaccag    780

gaggtgaagc agagaatgat gacatggatc agactttaat aattgctgcc aggaacattg    840

taagaagatc aattgttgca attgatccct tagcatcctt aatatctatg tgtcatacta    900

caaacatatc tgccgaacca ctcactgaaa tactaaaggc gaatccaaca gatgagcaag    960

ctgtaaatat ttgcaaagca gctcttggaa tcaaaataaa taatagtttt agctttggag   1020

gctataactt taagaaaata aaaggaaatt caaaaaggag tgaacagcag gtattgactg   1080

ggaatcttca gacattaaca ttaacaatct ttgaaggtta cgaagaattc aatgtatctg   1140

ggaaaagagc ttctgcagta ttgaagaaag gaacacaaag gctcatacaa gcaattattg   1200

gtggaagaac tattgaagat atactaaatt tgatgataac actgatggtc ttctctcaag   1260

aagataaaat gataaaatca gtaagagggg atttgaattt cctcaacaga gcaaatcaac   1320

gattgcaccc catgtaccaa ttattaagac atttccaaaa agactctgga gttcttttaa   1380

ggaactgggg aatggaagac atagacccag taatgggaat tatgggaata ttaccagatg   1440

gaacaataaa caggaatact acattggttg gagtaagaat aagtcaggga ggagttgatg   1500

aatactcttt caacgaaaga ataagagtgt caattgacaa atacttaagg gtcaaaaatg   1560

aaaagggaga attactaata agcccagaag aagtaagtga agcacaagga caagaaaaat   1620

taccaataaa ctacaattcg tccctgatgt gggaggtaaa tggcccagaa tcaatactaa   1680
```

```
caaacactta tcactggata ctaaaaaact gggaaatctt aaaaacccaa tggatgacta   1740

cacctaatat tctatataat agaatggaat ttgaaccttt tcaaacttta atacccaaag   1800

ggaatagagc tgcatatagt ggttttacta gaactctatt tcaacaaatg agagatgtag   1860

aaggaacctt tgacagtatt caaataataa agctcttacc atttgcagca cacccaccgt   1920

ctgctggtcg aagtcaattc agttccttca ccattaacat aagaggtgca ccactcaggc   1980

ttctaataag agggaactca caaattttca actacaataa aatggaaaac agtatcatta   2040

tattaggaaa aaatgtagga aaactagatg aatcaataat aacagaaacc aacactattg   2100

agtctgctgt gttaaggggt ttcctaattc ttgggaaagc caacagtaaa tatggacctg   2160

tattgactat tgcagagctt gataaattag gaaggggaga aaaagcaaat gtcctgatag   2220

gacagggaga tacagtgttg gtcatgaaac gaaaaagaga ctccagtata cttactgata   2280

gccagacagc catcaaaagg attcgtttgg aggaatcaaa ataaaatcac taaaaatgac   2340

cttgtttcta ctaatacgag acgatat                                       2367
```

```
<210> SEQ ID NO 18
<211> LENGTH: 2368
<212> TYPE: DNA
<213> ORGANISM: Influenza A virus
<220> FEATURE:
<221> NAME/KEY: misc_feature
<222> LOCATION: (1)..(2368)
<223> OTHER INFORMATION: Synthetic cDNA construct encoding for H18N11
      PB1

<400> SEQUENCE: 18
```

```
tattcgtctc agggagcaga agcaggcaaa ctattttgaa atggacgtca atccgatgct     60

aatatttcta aaggttccag tgcaaaatgc aattagcact actttcccat atacagggga    120

ccctccttac agccatggaa caggtactgg atataccatg gacactgtta taagaactca    180

tgaatattca aacaaaggag tttggactac aaacagtgaa acatcagcca ttcaattgaa    240

cccaattgat ggaccactac cagaggataa tgaacctagt ggatatgctc agacagactg    300

tgtattagaa ttgattgaaa aattaggaga gtcacatcca ggacttttta acattgcatg    360

ccaagagaca attgattcaa tccagcaaac tagagttgat aaacttactc aaggtagaca    420

aacctatgat tggactttaa atagaaatca accagctgca acagcacttg caaacactat    480

agaagttttc agaaaaaatg gctatacagc aaatgaatcg ggaagattaa tagactttct    540

aaaagatgta ctaatctctt ttgagaaaga atcaatggaa attgtaactc actatcaaaa    600

gaaaaagaga ataagagata atcacactaa aagaatggta actcagagga ctataggaaa    660

aagaaagaca aaattaagca gaaagtcata tctaataaga gctttaactc tcaataccat    720

gactaaagat gcagagagag gaaaattaaa acgccgtgct atagcaacac caggaatgca    780

aataagagga tttgtatatt ttgtagaatt acttgcaaga aacatctgtg aaagattaga    840

acaatcagga ttacctgtcg ggggcaatga aaagaaagct aaattagcaa atgttattaa    900

gaaaatgatg gccaagtcaa gtgatgagga actttcctac acaattactg gagacaacac    960

aaaatggaat gaaaaccaaa acccaaggat ttttctagct atgattctca aaataacaga   1020

aggtcaacct gaatggttca gagacctatt agctgtcgcc ccaataatgt tttccaacaa   1080

agttgcaaga cttggacggg gatacatgtt tgaaagtaag tcaatgaaag ttaggactca   1140

aatacctgca gaagaactga atactataag cttaaaatac ttcaatgagg aaacaaaaaa   1200

gaaaattgaa aaagtgagaa atcttatgat tgatggaaca gcatcactga gcccaggaat   1260
```

gatgatgggc atgttcaata tgctaagcac tgtgttagga gtcagcgttt taaacattgg 1320
gcaaaaacaa atgttaaaaa ccacatactg gtgggatgga ctacagtctt ccgatgactt 1380
tgctcttata gtaaatggac attttaaaaa tgatatacaa caaggcgtaa atcatttcta 1440
tagaatttgc aaattagtag gtataaacat gtctcaaaag aaatcctaca ttaacaaaac 1500
aggaaccttt gagttcacaa gtttttcta tagatatggt tttgtggcca atttttctat 1560
ggaactaccc tcttttggtg ttgcaggaaa caatgagtct gctgatatga gtataggcac 1620
aacagttata aaaacaaaca tgataaacaa tgatctaggc cctgcaacag cgcagatggc 1680
cattcagctc tttataaaag attacaggta cacttataga tgccatcggg gagacactaa 1740
tttagaaaca agaagaacca aaagtttaaa gagattatgg acagaaacaa tatccaaatc 1800
tggattatta gtatcagatg gtggtcctaa tccttacaat ttaaggaatt tacatatacc 1860
tgaagtatgt ctaaaatggc atttgatgga tccagagtac agagggaggc tgtgcaatcc 1920
caataatcca tttgtgcacc atatggaagt cgaaagcacg aatcttgcag taataatgcc 1980
agcccacggg ccagcaaagt caatggagta tgatgctgtt gctacaactc attcatggac 2040
acctaaaagg aatagatcaa ttttgaacac caatcaaaga ggaatattgg aagatgaaag 2100
aatttaccaa aaatgttgcc agatatttga aaaattcttc cccagttcaa gttataggag 2160
acctatcgga atggcaagta tgttggatgc tatgctgtca agagctaaaa tcgatgctag 2220
gatagatcta gaatcaggta gattaagcaa tcaagatttc tcagagataa tgaatatctg 2280
taaagcaatc gaaaatttga aacgcagata aggatcatta gctatcaatg cgaaaaaatg 2340
ccttgtttct actaatacga gacgatat 2368

<210> SEQ ID NO 19
<211> LENGTH: 2245
<212> TYPE: DNA
<213> ORGANISM: Influenza A virus
<220> FEATURE:
<221> NAME/KEY: misc_feature
<222> LOCATION: (1)..(2245)
<223> OTHER INFORMATION: Synthetic cDNA construct encoding for H18N11 PA

<400> SEQUENCE: 19
tattcgtctc agggagcaga agcaggtact tagacaatgg agaatttcat aagagcaaac 60
ttcaatccaa tgattctaga gagggcagaa aaaagtatga aagaatatgg agaaagtccc 120
caaaatgaag gaaacaagtt tgccgctata tctactcatc ttgaagtatg tttcatgtat 180
tctgattttc atttcattga tctagaaggg aatgcaataa tcaaagagtc agaagatgac 240
aacacaatgt taaaacatag atttgaaatc attgaaggcc aggaaagaaa tgttgcctgg 300
actattgtaa attcaatatg caatatgacc aatatagata aaccaaggta ccttccagat 360
ctctatgact acaaaactaa taggttcatt gaaattggag taactagaag aagggttgaa 420
gattattatt atgagaaagc taacaagttg aaagatggaa acgtttacat tcatatcttt 480
tcatttgacg gagaagaaat gtcaacagat gatgaataca ttcttgatga agaaagtaga 540
gcaagaatca aaacaaggct ctttgttcta cgtcaagaaa tggcatcagc aggactgtgg 600
gattcctttc gtcaatcaga aaagggtgaa gaaacagttg aggaggaatt caaatttcca 660
cccacattca agaagttggc ggatcaaagt cttccaccat cattcaagga ctataatcaa 720
ttcaaagtat atgtatcctc ttttaaatca aatggaaaca ttgaagctaa attaggagca 780
atgagtgaaa aagtaacagc tacaattgaa gaattcaatc ccaaagatat aactgagtta 840

-continued

```
aaaatgccca aaggtaaacc atgtacacaa aggagcaaat ttttgctaat ggactcaatg    900

aaattgtcaa tattaaatcc atctcatgaa ggtgaaggaa ttcctatgaa agatgcgact    960

gcatgcatgg aaaccttttg ggggtggaaa aaaccaaata taattaaaaa acatgataaa   1020

ggtgtgaata ccaattatct aatgatttgg gaacaactat ttgatgctct caaagagaat   1080

gaaaacaaat atcttaattt gaagaagact aatcatctaa aatgggggct aggagaagga   1140

caagctcctg aaaaaatgga ttttgaagat tgtaaagaca tccctgattt gttccaatac   1200

aaaagtgatc caccagaacc cagacaattg gcaagttgga ttcaaagtga attcaacaaa   1260

gcatcagagc taacaagctc aaactggatc gaatttgatg aactaggaga agatgtagct   1320

cctatagagc atatagcaag tagaagacga aacttcttca ctgcagaggt ctcacaatgt   1380

agagcctcag aatacattat gaaggctgta tacataaata cagcactttt aaactcctcc   1440

tgtacagcta tggaggaata tcaagtaata ccaataatta ccaaatgtag agacatctct   1500

ggacaaagga aaacaaacct atatgggttt attatcaagg gaagatccca tctaagaaat   1560

gacacagatg ttgtgaattt catatcattg gaattttcat tgactgatcc aaggaatgaa   1620

ccacataaat gggaaaaata ttgcgtcctg gaaattggtg atatggaaat aaaaaacatca  1680

ataagcacaa taatgaaacc agtttactta tatgttcgga ctaatgggac atccaaaata   1740

aaaatgaaat ggggaatgga aatgagaaga tgtttactac aatctcttca acaagtagaa   1800

agcatgatag aagcagaatc tgctgttaaa gaaaaagaca tgacagaaac attctttcga   1860

aataaagaga atgaatggcc tattggagaa agtccaaaag gaatagagaa aggcaccatt   1920

gggaaagtgt gcagagttct tctagccaaa tcagttttca atagcatata tgcttccgcc   1980

caattggaag gtttctccgc agaatctaga aaactttgt tgctaataca agcatataga   2040

gacaatttag accctggaac ttttgatctt aaagggctat acgaagcaat tgaggagtgt   2100

atcattaatg atccttgggt ccttttaaat gcgtcatggt ttaactcctt ccttagagca   2160

gtacaaagaa gcttgtaaat aactctatca gttttagttc aatataagaa aaaagtacct   2220

tgtttctact aatacgagac gatat                                         2245
```

<210> SEQ ID NO 20
<211> LENGTH: 1800
<212> TYPE: DNA
<213> ORGANISM: Influenza A virus
<220> FEATURE:
<221> NAME/KEY: misc_feature
<222> LOCATION: (1)..(1800)
<223> OTHER INFORMATION: Synthetic cDNA construct encoding for H18N11 HA

<400> SEQUENCE: 20

```
tattcgtctc agggagcaga agcagggtga ttattattca gaatgattac aatacttatc     60

ttggtactcc ctattgttgt aggtgaccaa atatgcattg gctatcattc aaataattca    120

acacaaacag tgaatactct ccttgaatca aatgtaccag tgacttcctc tcacagcatc    180

ctagaaaaag aacacaatgg tttgctttgc aagctaaaag ggaaagcacc cttggacctt    240

attgactgct ctcttcctgc atggcttatg ggaaacccaa aatgtgacga actcttaaca    300

gcaagcgaat gggcctacat aaaagaagac ccagaacctg aaaatggaat ctgttttcca    360

ggagattttg attctttaga ggatctgatt ttattggttt ctaacactga ccatttcaga    420

aaagagaaaa taatagacat gaccagattc tctgatgtga ctacaaacaa cgtagacagt    480

gcatgcccat atgacacaaa tggtgcttcc ttttacagaa atctaaactg ggtgcagcaa    540

aacaaaggca agcaactgat tttcactac cagaattctg aaaacaaccc acttttgata     600
```

-continued atttggggag tacaccagac atctaatgct gcagaacaaa acacatacta tggctcacag 660
actggctcaa caaccatcac tattggggaa gaaacaaaca cttatccact agtgataagt 720
gaaagttcta ttcttaacgg tcactctgat agaataaatt acttttgggg agttgtcaat 780
cctaatcaga atttttcaat tgtcagtaca gggaatttca tctggccaga gtacggatac 840
tttttccaaa aaacaaccaa tataagtgga ataataaaat caagtgaaaa gataagtgat 900
tgtgacacaa tctgccagac aaaaaattggg gcaataaaca gcacactgcc ttttcagaat 960
atccatcaaa atgcgattgg agattgtcct aaatatgtga aagcccaaga acttgttctt 1020
gcaactggat taaggaacaa tccaataaaa gaaacaagag ggctttttgg tgcaattgca 1080
ggtttcatcg agggaggatg gcaaggattg attgatggtt ggtatgggta tcaccaccag 1140
aactcagaag gttcaggcta tgctgctgac aaagaagcaa cccagaaggc tgttgatgca 1200
ataaccacaa aagtaaacaa cataatagac aaaatgaaca cgcaatttga atcaactgcc 1260
aaagaattca acaaaattga aatgagaata aaacatctca gtgacagagt tgatgatggc 1320
ttcttggatg tttggagtta caatgctgaa ttactcgttt tgctggaaaa tgaaagaact 1380
ctggacttcc atgatgcaaa tgttaacaat ttgtatcaaa aagtgaaagt ccagctgaaa 1440
gacaatgcaa ttgacatggg aaacggctgt ttcaagattc tacacaaatg caacaacaca 1500
tgtatggatg acattaaaaa cggaacatac aattattatg aatacagaaa ggaaagccac 1560
ttggagaaac aaaaaattga cggtgtgaag ctatcagaaa acagctcata taaaataatg 1620
atcatttact caacagtggc aagttcagta gtgcttggct tgattatact agccgcaatt 1680
gaatggggct gttttaaagg gaacctgcaa tgcagaatat gtatttgagg ctgtggtgtt 1740
agctaatgtc aatctattat tgcaaaaaac acccttgttt ctactaatac gagacgatat 1800

<210> SEQ ID NO 21
<211> LENGTH: 1586
<212> TYPE: DNA
<213> ORGANISM: Influenza A virus
<220> FEATURE:
<221> NAME/KEY: misc_feature
<222> LOCATION: (1)..(1586)
<223> OTHER INFORMATION: Synthetic cDNA construct encoding for H18N11 NP

<400> SEQUENCE: 21
tattcgtctc agggagcaga agcagggtta ataatcacat tgtgacattt aaagatggct 60
ggtcaaggta ctaagcgtac ctttgagcaa atggagactg attccaaaca aaacacaact 120
gaaatccgat cagcagtagg cagaatggta aaagcaattg ggcggtttta catccaaatg 180
tgtgcagagc ttaaattgga tgacaaagag gctgtgttaa tccaaaatag cctaactatt 240
gaaagaatgg tgctttcagc atttgatgaa agaaggaaca aatacctaga agagcatccc 300
acagttggga aagaccctaa gaaaaccgga gggccaatct acagaaggaa agaagggaaa 360
tgggaaagag agatggttct aatggaaaaa gaaaatatca gagccatttg gaagatggca 420
aatgatggag aagaaaacct ttcgggattg agccatataa tgatatggca ttccaacctc 480
aatgatacaa cataccaaag aacaagagca ttggtgagaa caggaatgga cccaagaatg 540
tgctctctga tgcaaggatc aacacttccc cgaagggccg gagcagcagg agctgccata 600
aaaggtgtgg gcacactgat aatggaacta atcaggatga taaagagagg gatgaatgac 660
aggaactttt ggaaaggtga acagggaaaa agaacaagag ctgcctacga aaggatctgc 720
aacaatttga agaataagtt tcagactgct ccacagaaag caatggttga ccaagtgaaa 780

-continued

```
gaagggaaaa atcctgggaa tgcagagatt gaagatctac tgtttctagc tagatcagca    840

ttgatcctca gaggagctgt tgctcataaa tcgagcctcc ctgcttgtgt atacggctta    900

ggggtatcca gaggatttga ttttgaaaga gagggttact cactggttgg gagagaccct    960

tatatgcttc tccagaactc acagatcttc tccataattc ggaaaggaga gaatgcagcc   1020

cacaagagcc aactggtatg gatggcctgc catgcagctg cttttgaaga cataagagta   1080

agcagtttta taaaaggaaa taaaatagtc cccagaggaa aattggagac tagaggtctc   1140

caaatagcag ggtcagaaac ccttgatgaa gccctggttg ttagcctgga cataaagagt   1200

cattattggg caatcaagac gaggagtgga ggaaatcctc aacagtcaag aagttcagct   1260

ggtcagattg ctgttcagcc aaccttctcc gtacaaagga atattccttt tgaaaagaaa   1320

acaataatgg ctgcattttc taacattgaa gagggaagaa tcactgacat gagaactgaa   1380

ataataaagc tgatggaaaa ttctgacccc aaagacaaag ttttcctggg gagaggagtg   1440

ttcgagatgg ctgatgagaa ggcaactaac ccgatagtgc cttctttgga tgggaatgac   1500

gagggttctt atttctttgg agacaaagca gaggagtttg acatatgaga aaaaataccc   1560

ttgtttctac taatacgaga cgatat                                        1586
```

<210> SEQ ID NO 22
<211> LENGTH: 1409
<212> TYPE: DNA
<213> ORGANISM: Influenza A virus
<220> FEATURE:
<221> NAME/KEY: misc_feature
<222> LOCATION: (1)..(1409)
<223> OTHER INFORMATION: Synthetic cDNA construct encoding for H18N11 NA

<400> SEQUENCE: 22

```
tattcgtctc agggagcaga agcaggagtt tttcataatg tcgtttcaaa catcgacatg     60

tctgttgatt gtttccctaa tatgtgggat actaacagtc tgccttcagg tactgttacc    120

cttcatattg atatggacaa atacagaacc aaattattcc tgtgagtgtc cagctcccaa    180

catcagtctt agctgtccaa acgggacttc tgtaacatat gacagtaaaa atataactga    240

aaacagcttc tacagttcaa caacaaacta cctgtcccct gtcattgcaa cccctctggt    300

gctaggagag aatctgtgca gcataaatgg gtgggttcca acctacagag gagaaggaac    360

aaccggaaaa attcctgatg aacaaatgct gaccagacag aactttgtat cctgctcaga    420

taaagagtgt cgaagatttt ttgtgagtat gggatacgga actaccacaa attttgcaga    480

cctaattgtg tcagaacaaa tgaatgttta cagtgtaaag ttaggagacc ctccaacacc    540

tgacaagtta aaatttgaag ctgttggctg gagtgccagc tcgtgtcatg atggctttca    600

gtggactgtc ctgtccgttg caggggacgg ttttgtgagc atcctttatg gaggaattat    660

aactgataca attcatccaa caaatggagg cccactgaga acacaagctt catcttgcat    720

atgcaatgat ggaacttgtt atacaatcat tgctgatgga accacttaca ctgcatcttc    780

tcacagactt tacagactag tcaatggaac atctgccggc tggaaggccc ttgataccac    840

agggttcaat tttgagtttc cgacttgcta ctatacaagt ggcaaagtaa aatgtaccgg    900

aacaaatctt tggaatgatg ccaagaggcc ctttcttgaa tttgaccagt ccttcactta    960

cactttcaag gagccatgct tggggttcct tggggacacc ccaagaggga ttgacaccac   1020

taattactgt gacaagacaa caacagaggg agagggtgga atccaaggtt tcatgattga   1080

aggctcaaac tcctggatag gaagaattat taatccagga tccaagaaag gatttgaaat   1140

ttataagttc ctgggaacat tgttttctgt ccaaactgta ggaaatagga actaccaatt   1200
```

gttaagtaac agcacaattg ggagatcagg cctgtatcag cctgcttatg aatcacgtga 1260
ttgtcaagag ttgtgttttt ggattgaaat tgctgcaact accaaagcag gcttgtcatc 1320
caatgatctg attacttttt gtgggacagg aggctcaatg ccagatgtca actgggggta 1380
agtatatgat tacaaatacg agacgatat 1409

<210> SEQ ID NO 23
<211> LENGTH: 1056
<212> TYPE: DNA
<213> ORGANISM: Influenza A virus
<220> FEATURE:
<221> NAME/KEY: misc_feature
<222> LOCATION: (1)..(1056)
<223> OTHER INFORMATION: Synthetic cDNA construct encoding for H18N11 M

<400> SEQUENCE: 23
tattcgtctc agggagcaga agcaggcatt attcaaaatg agtatcttga ctgaggttga 60
aacgtacgta ctatcaatca tcccatctgg gcctctcaaa gctgaaatag cccaaaagct 120
tgaggatgtc ttctcaggcc gtaatagtga cctggacacc ttgcttgaat ggctaaaaac 180
gagacccatt ctatcaccac taactaaggg gatagtcggg tttgttttca cactcactgt 240
gccctgtgag aagaatactt ccagaaggaa gtttatacaa acagccctca atgggaatgg 300
tgaaactgcc aacatggaca aggcagttaa aatttacaaa aagctcaaaa aagaaatcac 360
ctttcatgga gccaaggaag tggctctaag ttatccaact ggagccttag cctgctgcat 420
ggggctgatt tacaacagaa tgggctcagt aaccacagaa gttgcatttg gtttggtttg 480
tgccacatgt gagcacattg ctgactcaca gtacagatcc cataagcaaa tggtgggttc 540
tactaatcct ctgatcagac atgaaaaccg aatggcaact gcagctagca ctgctaaagc 600
catggaacaa atggcaagta gtagtgatca ggcagctgaa gcaatggaaa ttgcttcaca 660
agccagacaa atgatccagg cgatgagagc cattggaaca cacccaacaa cttccagtgg 720
cctcaaagat gatttgcttg acaatttgca ggcttaccag aaaaggatgg gaatccagat 780
gcagcggttt aaatgaagac ctgatattag ctgcaaacat aatcgggatc attcatctgg 840
cactttggat cattgacaga tggctctatc gctacagtct attaatatat cgaaaaattt 900
ggaatacttg gggactgaaa ccagttgatt ctacaaaaga attgagggaa gaattcaaag 960
aagagcacaa atcaatagaa tttccagatc caattatgac tatcatcgaa aattaaaatg 1020
aaaaaatgcc ttgtttctac taatacgaga cgatat 1056

<210> SEQ ID NO 24
<211> LENGTH: 924
<212> TYPE: DNA
<213> ORGANISM: Influenza A virus
<220> FEATURE:
<221> NAME/KEY: misc_feature
<222> LOCATION: (1)..(924)
<223> OTHER INFORMATION: Synthetic cDNA construct encoding for H18N11 NS

<400> SEQUENCE: 24
tattcgtctc agggagcaga agcagggtat ctaaagacat aatggaatcg accccgacaa 60
ctatcgcatt tcaggtggat tgctatttat ggcatttgaa gaaaatgcta agcctaatgg 120
gggaggtcga tgcacccttt gaagatcggt taagaagaga gcaaaaagct ctgaaaggaa 180
gaagcatgac tctggggata gacatccaag ctgcaacgaa agcaggatat tataaaataa 240
agtctatcac agaggatgcc atgccttact acgggattct ccccaatgcc ggacagagcg 300

```
aaccgaaata tatcactgaa atgacagtgg aagaaacaaa cagaaattgg attatgatcc    360
agccaaaaca gaaagtgatt ggtggaagga tcctcattag catggatcaa gcaatcactg    420
ataaagttat aacaataaag gcaaacttta cagtctgttt tggaaaagtt gaaagactgg    480
ttctagctcg agcattcact ccagaaggtg ctgtagtagg ggagataaac cctctgtctt    540
ttgttacagg acatactgga gaggatgtca aaactgcata tgaactcttc agaagcggat    600
ttgaatggaa tgataacgca attgaagaat ctcaaattct tcagggattc cttggaagaa    660
tcgctgatgc ggaacggaga ctacaggaaa atgagccagc agaatgaaaa ctggagatct    720
cagcttggag ataaattgaa tgttataaga aatctcatcc aaacttgcag ggagatttta    780
ctaacctcaa caaacagctt tatagagata acctttctcg ctgctcttaa cctcctattg    840
gaggttgaaa gagaaatgag aacattagca tttcaattaa tatgattaaa aaataccctt    900
gtttctacta atacgagacg atat                                           924
```

```
<210> SEQ ID NO 25
<211> LENGTH: 1993
<212> TYPE: DNA
<213> ORGANISM: Influenza A virus
<220> FEATURE:
<221> NAME/KEY: misc_feature
<222> LOCATION: (1)..(1993)
<223> OTHER INFORMATION: Chimeric cDNA sequence encoding hemagglutinin
      of H3N2 synthesized from published sequences of
      A/swine/Texas/4199-2/1998 and H18N11 platform

<400> SEQUENCE: 25
```

```
tattcgtctc agggagcaga agcagggtga ttattattca gagtgattac aatacttatc     60
ttggtactcc ctattgttgt aggtgaccaa atatgcattg gaaatgaaga ctatcattgc    120
tttgagctac attttatgtc tggttttcgc tcaaaaactt cccggaaatg acaacagcac    180
agcaacgctg tgcctgggac accatgcagt gccaaacgga accctagtga aaacaatcac    240
gaatgatcaa attgaagtga ctaatgctac tgagctggtt cagagttcct caacaggtag    300
aatatgcgac agtcctcacc gaatccttga tggaaaaaac tgcacattga tagatgctct    360
actgggagac cctcattgcg atggctttca aaataaggaa tgggaccttt ttattgaacg    420
cagcaaagct tacagcaact gttaccctta tgatgtgccg gattattcct cccttaggtc    480
actagttgcc tcatcaggca ccctggagtt taccaatgaa gacttcaatt ggactggggt    540
cgctcaggat gggggaagct attcttgcaa aaggggatct gttaaaagtt tctttagtag    600
attgaattgg ttacacaaat tagaatacaa atatccagca ctgaacgtga ctatgccaaa    660
caatgacaaa tttgacaaat tgtacatttg gggggttcac cacccgagca cggacagtga    720
acaaaccagc ctgtatgttc aagcaatagg gagagtcaca gtctctacca aaagtagcca    780
acaaactgta atcccgaaca tcgggtccag accctgggtg aggggcatct ccagtagaat    840
aagcatctat tggacaatag taaaaccggg agacatactt ttgattagca gcacagggaa    900
tctaattgct cctcggggtt acttcaaaat acgaaatggg aaaagctcaa taatgaggtc    960
agatgcaccc attgacaact gctattctga atgcatcact ccaaatggaa gcattcccaa   1020
tgacaaacct tttcaaaatg taaataggat cacatatggg gcctgtccca aatatgttaa   1080
gcaaaaaact ctgaaattgg caacagggat gcggaatgta ccagagaaac aaactagagg   1140
catattcggc gcaatcgcag gtttcataga aaatggttgg gagggaatgg tagacggttg   1200
gtacggtttc aggcatcaaa attctgaggg cacaggacaa gcagcagatc ttaaaagcac   1260
ccaagcagca atcgatcaag tcaacgggaa attgaatagg ttaatcgaga aaacgaacga   1320
```

gaaattccat caaatcgaaa aagaattttc agaagtagaa gggagaattc aggacctcga 1380
gaaatatgtt gaagacacta aaatagatct ctggtcttac aacgcggagc tccttgttgc 1440
cctggagaat caacatacaa ttgatctaac tgactcagaa atgaacaaac tgtttgaaaa 1500
aacaaggaag caactgaggg aaaatgctga ggacatgggc aatggttgct tcaaaatata 1560
ccacaaatgt gacaatgcct gcatagggtc aatcagaaat ggaacttatg accatgatgt 1620
atacagagac gaagcattaa acaaccggtt ccagatcaaa ggtgttgagc tgaaatcagg 1680
atacaaagat tggatcctat ggatttcctt tgccatatca tgctttttgc tttgtgttgt 1740
tttgctgggg ttcatcatgt gggcctgcca aaaaggcaac attaggtgca acatttgcat 1800
ttgagtgcat taaatcattt actcaacagt ggcaagttca gtagtgcttg gcttgattat 1860
actagccgca attgaatggg gctgttttaa agggaacctg caatgcagaa tatgtatttg 1920
aggctgtggt gttagctaat gtcaatctat tattgcaaaa aacacccttg tttctactaa 1980
tacgagacga tat 1993

<210> SEQ ID NO 26
<211> LENGTH: 1858
<212> TYPE: DNA
<213> ORGANISM: Influenza A virus
<220> FEATURE:
<221> NAME/KEY: misc_feature
<222> LOCATION: (1)..(1858)
<223> OTHER INFORMATION: Chimeric cDNA sequence encoding neuraminidase of H3N2 synthesized from published sequences of A/swine/Texas/4199-2/1998 and H18N11 platform

<400> SEQUENCE: 26
tattggtctc agggagcaga agcaggagtt tttcatactg tcgtttcaaa catcgacatg 60
tctgttgatt gtttccctaa tatgtgggat actaacagtc tgccttcagg tactgttacc 120
cttcatattg atatggacaa atacagaacc aaattattcc tgtgagtgtc cagctcccaa 180
catcagtctt agctgtccaa acgggacttc tgtaacatat atgaatccaa atcaaaagat 240
aataacgatt ggctctgttt ctctcactat tgccacaatg tgcttcctta tgcaaattgc 300
catcctggta actactgtaa cattgcattt caagcaatat gaatgcaact accccccaaa 360
caaccaagta atactgtgtg aaccaacaat aatagaaaga aacataacag agatagtgta 420
tctgaccaac accaccatag agaaggaaat atgccccaaa ctagcagaat acagaaattg 480
gtcaaagccg caatgtaaaa ttacaggatt tgcacctttt tccaaggaca attcgattag 540
gctttccgct ggtggggaca tttgggtgac aagagaacct tatgtgtcat gcgatcctga 600
caagtgttat caatttgccc ttggacaggg aacaacacta aacaacaggc attcaaatga 660
cacagtacat gataggaccc cttatcgaac cctattgatg aatgagttgg gtgttccatt 720
tcatttggga accaagcaag tgtgcatagc atggtccagc tcaagttgtc acgatggaaa 780
agcatggctg catgtttgtg taactgggca tgatgaaaat gcaactgcta gcttcattta 840
cgatgggagg cttgtagata gtattggttc atggtccaaa aaaatcctca ggacccagga 900
gtcggaatgc gtttgtatca atggaacttg tacagtagta atgactgatg ggagtgcttc 960
aggaagagct gatactaaaa tattattcat tgaggagggg aaaatcgttc atattagccc 1020
attgttagga agtgctcagc atgtcgagga gtgctcctgt tatcctcgat atcctggtgt 1080
cagatgtgtc tgcagagaca actggaaagg ctccaatagg cccatcgtag atataaatgt 1140
aaaggattat agcattgttt ccagttatgt gtgctcagga cttgttggag acacacccag 1200

```
aaaaaacgac agatccagca gtagcaattg cctgaatcct aacaatgagg aagggggtca   1260

tggagtgaaa ggctgggcct ttgatgatgg aaatgacgtg tggatgggaa gaacgatcaa   1320

cgagaagtta cgctcaggtt atgaaacctt caaagtcatt gaaggctggt ccaaacctaa   1380

ctccaaattg cagataaata ggcaagtcat agttgacaga ggtgataggt ccggttattc   1440

tggcattttc tctgttgaag gcaaaagctg catcaatcgg tgcttttatg tggagttgat   1500

aaggggaagg aaacaggaaa ctgaagtatg gtggacctca aacagtattg ttgtgttttg   1560

tggcacctca ggtacatatg gaacaggctc atggcctgat ggggcggaca tcaatctcat   1620

gcctatataa aggcctgtat cagcctgctt atgaatcacg tgattgtcaa gagttgtgtt   1680

tttggattga aattgctgca actaccaaag caggcttgtc atccaatgat ctgattactt   1740

tttgtgggac aggaggctca atgccagatg tcaactgggg gtaagtatat gattacattc   1800

atattttaaa tggatgtata agaaaaaact ccttgtttct actaatacga gaccatat     1858
```

```
<210> SEQ ID NO 27
<211> LENGTH: 1968
<212> TYPE: DNA
<213> ORGANISM: Influenza A virus
<220> FEATURE:
<221> NAME/KEY: misc_feature
<222> LOCATION: (1)..(1968)
<223> OTHER INFORMATION: Chimeric cDNA sequence encoding hemagglutinin
      of H3N2 synthesized from published sequences of
      A/swine/Texas/4199-2/1998 and H17N10 platform

<400> SEQUENCE: 27

agcagaagca gggtcactat tactctgtgc tactgtggag ctgattgtcc tactaatcct     60

tctcaatcct tatacttttg tattagggga cagaaatgaa gactatcatt gctttgagct    120

acattttatg tctggttttc gctcaaaaac ttcccggaaa tgacaacagc acagcaacgc    180

tgtgcctggg acaccatgca gtgccaaacg gaaccctagt gaaaacaatc acgaatgatc    240

aaattgaagt gactaatgct actgagctgg ttcagagttc ctcaacaggt agaatatgcg    300

acagtcctca ccgaatcctt gatggaaaaa actgcacatt gatagatgct ctactgggag    360

accctcattg cgatggcttt caaaataagg aatgggacct tttattgaa cgcagcaaag     420

cttacagcaa ctgttaccct tatgatgtgc cggattattc ctcccttagg tcactagttg    480

cctcatcagg caccctggag tttaccaatg aagacttcaa ttggactggg gtcgctcagg    540

atgggggaag ctattcttgc aaaaggggat ctgttaaaag tttctttagt agattgaatt    600

ggttacacaa attagaatac aaatatccag cactgaacgt gactatgcca aacaatgaca    660

aatttgacaa attgtacatt tgggggttc accacccgag cacggacagt gaacaaacca     720

gcctgtatgt tcaagcaata gggagagtca cagtctctac caaaagtagc caacaaactg    780

taatcccgaa catcgggtcc agaccctggg tgaggggcat ctccagtaga ataagcatct    840

attggacaat agtaaaaccg ggagacatac ttttgattag cagcacaggg aatctaattg    900

ctcctcgggg ttacttcaaa atacgaaatg ggaaaagctc aataatgagg tcagatgcac    960

ccattgacaa ctgctattct gaatgcatca ctccaaatgg aagcattccc aatgacaaac   1020

cttttcaaaa tgtaaatagg atcacatatg ggcctgtcc caaatatgtt aagcaaaaaa    1080

cyctgaaatt ggcaacaggg atgcggaatg taccagagaa acaaactaga ggcatattcg   1140

gcgcaatcgc aggtttcata gaaaatggtt gggagggaat ggtagacggt tggtacggtt   1200

tcaggcatca aaattctgag ggcacaggac aagcagcaga tcttaaaagc acccaagcag   1260

caatcgatca agtcaacggg aaattgaata ggttaatcga gaaaacgaac gagaaattcc   1320
```

-continued

```
atcaaatcga aaaagaattt tcagaagtag aagggagaat tcaggacctc gagaaatatg   1380

ttgaagacac taaaatagat ctctggtctt acaacgcgga gctccttgtt gccctggaga   1440

atcaacatac aattgatcta actgactcag aaatgaacaa actgtttgaa aaaacaagga   1500

agcaactgag ggaaaatgct gaggacatgg gcaatggttg cttcaaaata taccacaaat   1560

gtgacaatgc ctgcataggg tcaatcagaa atggaactta tgaccatgat gtatacagag   1620

acgaagcatt aaacaaccgg ttccagatca aggtgttga gctgaaatca ggatacaaag    1680

attggatcct atggatttcc tttgccatat catgcttttt gctttgtgtt gttttgctgg   1740

ggttcatcat gtgggcctgc caaaaaggca acattaggtg caacatttgc atttgagtgc   1800

attaaactct gtattctacc attgcatcat ccgtcgtgct tggctcgttg ataatagccg   1860

cttttctttg ggggtgccaa aaaggctcaa tccaatgtaa aatatgtata tagaacggtg   1920

gaattaacct tgtcattcag aaaagcaaaa aagacccttg tttctact                1968
```

<210> SEQ ID NO 28
<211> LENGTH: 1811
<212> TYPE: DNA
<213> ORGANISM: Influenza A virus
<220> FEATURE:
<221> NAME/KEY: misc_feature
<222> LOCATION: (1)..(1811)
<223> OTHER INFORMATION: Chimeric cDNA sequence encoding neuraminidase of H3N2 synthesized from published sequences of A/swine/Texas/4199-2/1998 and H17N10 platform

<400> SEQUENCE: 28

```
agcagaagca ggagttttta atactgtcta tcaacggaac gacctgtcta ctcacactca     60

gtctaatact cactgttata ctgatagggc tccaaatcct gctgcccttt attcttttct    120

ggaccaacag ccccccgcca gaaatctcca acagcactag ctgctgcaac ggaacctttc    180

tgactgaaac aaacaacaat ataaccatga atccaaatca aaagataata acgattggct    240

ctgtttctct cactattgcc acaatgtgct tccttatgca aattgccatc ctggtaacta    300

ctgtaacatt gcatttcaag caatatgaat gcaactaccc cccaaacaac caagtaatac    360

tgtgtgaacc aacaataata gaaagaaaca taacagagat agtgtatctg accaacacca    420

ccatagagaa ggaaatatgc cccaaactag cagaatacag aaattggtca aagccgcaat    480

gtaaaattac aggatttgca ccttttttcca aggacaattc gattaggctt tccgctggtg   540

gggacatttg ggtgacaaga gaaccttatg tgtcatgcga tcctgacaag tgttatcaat    600

ttgcccttgg acagggaaca acactaaaca acaggcattc aaatgacaca gtacatgata    660

ggacccctta tcgaacccta ttgatgaatg agttgggtgt tccatttcat ttgggaacca    720

agcaagtgtg catagcatgg tccagctcaa gttgtcacga tggaaaagca tggctgcatg    780

tttgtgtaac tgggcatgat gaaaatgcaa ctgctagctt catttacgat gggaggcttg    840

tagatagtat tggttcatgg tccaaaaaaa tcctcaggac ccaggagtcg gaatgcgttt    900

gtatcaatgg aacttgtaca gtagtaatga ctgatgggag tgcttcagga agagctgata    960

ctaaaatatt attcattgag gaggggaaaa tcgttcatat tagcccattg ttaggaagtg   1020

ctcagcatgt cgaggagtgc tcctgttatc ctcgatatcc tggtgtcaga tgtgtctgca   1080

gagacaactg gaaaggctcc aataggccca tcgtagatat aaatgtaaag gattatagca   1140

ttgtttccag ttatgtgtgc tcaggacttg ttggagacac acccagaaaa aacgacagat   1200

ccagcagtag caattgcctg aatcctaaca atgaggaagg gggtcatgga gtgaaaggct   1260
```

```
gggcctttga tgatggaaat gacgtgtgga tgggaagaac gatcaacgag aagttacgct   1320

caggttatga aaccttcaaa gtcattgaag gctggtccaa acctaactcc aaattgcaga   1380

taaataggca agtcatagtt gacagaggtg ataggtccgg ttattctggc attttctctg   1440

ttgaaggcaa aagctgcatc aatcggtgct tttatgtgga gttgataagg ggaaggaaac   1500

aggaaactga agtatggtgg acctcaaaca gtattgttgt gttttgtggc acctcaggta   1560

catatggaac aggctcatgg cctgatgggg cggacatcaa tctcatgcct atataaattc   1620

tttcaaccca aaggagacct catttctgga tgccaacgaa tctgtttctg gctggaaata   1680

gaagatcaaa cagtaggcct aggaatgatt caagaactca gcactttctg tgggataaac   1740

tcacctgttc agaatataaa ttgggattca tgaccaatgg acagcgaatg aaaaaactcc   1800

ttgtttctac t                                                         1811
```

<210> SEQ ID NO 29
<211> LENGTH: 1775
<212> TYPE: DNA
<213> ORGANISM: Influenza A virus
<220> FEATURE:
<221> NAME/KEY: misc_feature
<222> LOCATION: (1)..(1775)
<223> OTHER INFORMATION: Synthetic cDNA sequence encoding hemagglutinin from H1N1 A/Puerto Rico/8/1934

<400> SEQUENCE: 29

```
agcaaaagca ggggaaaata aaaacaacca aaatgaaggc aaacctactg gtcctgttaa     60

gtgcacttgc agctgcagat gcagacacaa tatgtatagg ctaccatgcg aacaattcaa    120

ccgacactgt tgacacagta ctcgagaaga atgtgacagt gacacactct gttaacctgc    180

tcgaagacag ccacaacgga aaactatgta gattaaaagg aatagcccca ctacaattgg    240

ggaaatgtaa catcgccgga tggctcttgg gaaacccaga atgcgaccca ctgcttccag    300

tgagatcatg gtcctacatt gtagaaacac caaactctga gaatggaata tgttatccag    360

gagatttcat cgactatgag gagctgaggg agcaattgag ctcagtgtca tcattcgaaa    420

gattcgaaat atttcccaaa gaaagctcat ggcccaacca caacacaaac ggagtaacgg    480

cagcatgctc ccatgagggg aaaagcagtt tttacagaaa tttgctatgg ctgacggaga    540

aggagggctc atacccaaag ctgaaaaatt cttatgtgaa caaaaaaggg aaagaagtcc    600

ttgtactgtg gggtattcat cacccgccta acagtaagga acaacagaat atctatcaga    660

atgaaaatgc ttatgtctct gtagtgactt caaattataa caggagattt accccggaaa    720

tagcagaaag acccaaagta agagatcaag ctgggaggat gaactattac tggaccttgc    780

taaaacccgg agacacaata atatttgagg caaatggaaa tctaatagca ccaatgtatg    840

ctttcgcact gagtagaggc tttgggtccg gcatcatcac ctcaaacgca tcaatgcatg    900

agtgtaacac gaagtgtcaa acacccctgg gagctataaa cagcagtctc ccttaccaga    960

atatacaccc agtcacaata ggagagtgcc caaaatacgt caggagtgcc aaattgagga   1020

tggttacagg actaaggaac actccgtcca ttcaatccag aggtctattt ggagccattg   1080

ccggttttat tgaaggggga tggactggaa tgatagatgg atggtatggt tatcatcatc   1140

agaatgaaca gggatcaggc tatgcagcgg atcaaaaaag cacacaaaat gccattaacg   1200

ggattacaaa caaggtgaac actgttatcg agaaaatgaa cattcaattc acagctgtgg   1260

gtaaagaatt caacaaatta gaaaaaagga tggaaaattt aaataaaaaa gttgatgatg   1320

gatttctgga catttggaca tataatgcag aattgttagt tctactggaa aatgaaagga   1380
```

-continued ctctggattt ccatgactca aatgtgaaga atctgtatga gaaagtaaaa agccaattaa 1440
agaataatgc caaagaaatc ggaaatggat gttttgagtt ctaccacaag tgtgacaatg 1500
aatgcatgga aagtgtaaga aatgggactt atgattatcc caaatattca gaagagtcaa 1560
agttgaacag ggaaaaggta gatggagtga aattggaatc aatggggatc tatcagattc 1620
tggcgatcta ctcaactgtc gccagttcac tggtgctttt ggtctccctg gggcaatca 1680 gtttctggat gtgttctaat ggatctttgc agtgcagaat atgcatctga gattagaatt 1740
tcagaaatat gaggaaaaac acccttgttt ctact 1775

<210> SEQ ID NO 30
<211> LENGTH: 1956
<212> TYPE: DNA
<213> ORGANISM: Influenza A virus
<220> FEATURE:
<221> NAME/KEY: misc_feature
<222> LOCATION: (1)..(1956)
<223> OTHER INFORMATION: Synthetic cDNA construct

<400> SEQUENCE: 30
agcagaagca gggtcactat tactctgtgc tactgtggag ctgattgtcc tactaatcct 60
tctcaatcct tatacttttg tattagggga cagaaatgaa ggcaaaccta ctggtcctgt 120
taagtgcact tgcagctgca gatgcagaca caatatgtat aggctaccat gcgaacaatt 180
caaccgacac tgttgacaca gtactcgaga agaatgtgac agtgacacac tctgttaacc 240
tgctcgaaga cagccacaac ggaaaactat gtagattaaa aggaatagcc ccactacaat 300
tggggaaatg taacatcgcc ggatggctct tgggaaaccc agaatgcgac ccactgcttc 360
cagtgagatc atggtcctac attgtagaaa caccaaactc tgagaatgga atatgttatc 420
caggagattt catcgactat gaggagctga gggagcaatt gagctcagtg tcatcattcg 480
aaagattcga aatatttccc aaagaaagct catggcccaa ccacaacaca aacggagtaa 540
cggcagcatg ctcccatgag gggaaaagca gtttttacag aaatttgcta tggctgacgg 600
agaaggaggg ctcataccca aagctgaaaa attcttatgt gaacaaaaaa gggaaagaag 660
tccttgtact gtggggtatt catcacccgc ctaacagtaa ggaacaacag aatctctatc 720
agaatgaaaa tgcttatgtc tctgtagtga cttcaaatta taacaggaga tttaccccgg 780
aaatagcaga aagacccaaa gtaagagatc aagctgggag gatgaactat tactggacct 840
tgctaaaacc cggagacaca ataatatttg aggcaaatgg aaatctaata gcaccaatgt 900
atgctttcgc actgagtaga ggctttgggt ccggcatcat cacctcaaac gcatcaatgc 960
atgagtgtaa cacgaagtgt caaacacccc tgggagctat aaacagcagt ctcccttacc 1020
agaatataca cccagtcaca ataggagagt gcccaaaata cgtcaggagt gccaaattga 1080
ggatggttac aggactaagg aacactccgt ccattcaatc cagaggtcta tttggagcca 1140
ttgccggttt tattgaaggg ggatggactg gaatgataga tggatggtat ggttatcatc 1200
atcagaatga acagggatca ggctatgcag cggatcaaaa aagcacacaa aatgccatta 1260
acgggattac aaacaaggtg aacactgtta tcgagaaaat gaacattcaa ttcacagctg 1320
tgggtaaaga attcaacaaa ttagaaaaaa ggatggaaaa tttaaataaa aaagttgatg 1380
atggatttct ggacatttgg acatataatg cagaattgtt agttctactg gaaaatgaaa 1440
ggactctgga tttccatgac tcaaatgtga agaatctgta tgagaaagta aaaagccaat 1500
taaagaataa tgccaaagaa atcggaaatg gatgttttga gttctaccac aagtgtgaca 1560
atgaatgcat ggaaagtgta agaaatggga cttatgatta tcccaaatat tcagaagagt 1620
caaagttgaa cagggaaaag gtagatggag tgaaattgga atcaatgggg atctatcaga 1680
ttctggcgat ctactcaact gtcgccagtt cactggtgct tttggtctcc ctgggggcaa 1740
tcagtttctg gatgtgttct aatggatctt tgcagtgcag aatatgcatc tgaactctgt 1800
attctaccat tgcatcatcc gtcgtgcttg gctcgttgat aatagccgct tttctttggg 1860
ggtgccaaaa aggctcaatc caatgtaaaa tatgtatata gaacggtgga attaaccttg 1920
tcattcagaa aagcaaaaaa gacccttgtt tctact 1956

<210> SEQ ID NO 31
<211> LENGTH: 1956
<212> TYPE: DNA
<213> ORGANISM: Influenza A virus
<220> FEATURE:
<221> NAME/KEY: misc_feature
<222> LOCATION: (1)..(1956)
<223> OTHER INFORMATION: Synthetic cDNA construct

<400> SEQUENCE: 31
agcagaagca gggtcactat tactctgtgc tactgtggag ctgattgtcc tactaatcct 60
tctcaatcct tatacttttg tattagggga cagaaatgaa agcgaatttg ttagttttac 120
tgtccgcgtt ggccgcggcc gacgcagaca caatatgtat aggctaccat gcgaacaatt 180
caaccgacac tgttgacaca gtactcgaga agaatgtgac agtgacacac tctgttaacc 240
tgctcgaaga cagccacaac ggaaaactat gtagattaaa aggaatagcc ccactacaat 300
tggggaaatg taacatcgcc ggatggctct tgggaaaccc agaatgcgac ccactgcttc 360
cagtgagatc atggtcctac attgtagaaa caccaaactc tgagaatgga atatgttatc 420
caggagattt catcgactat gaggagctga gggagcaatt gagctcagtg tcatcattcg 480
aaagattcga aatatttccc aaagaaagct catggcccaa ccacaacaca aacggagtaa 540
cggcagcatg ctcccatgag gggaaaagca gtttttacag aaatttgcta tggctgacgg 600
agaaggaggg ctcataccca aagctgaaaa attcttatgt gaacaaaaaa gggaaagaag 660
tccttgtact gtggggtatt catcacccgc ctaacagtaa ggaacaacag aatctctatc 720
agaatgaaaa tgcttatgtc tctgtagtga cttcaaatta taacaggaga tttaccccgg 780
aaatagcaga aagacccaaa gtaagagatc aagctgggag gatgaactat tactggacct 840
tgctaaaacc cggagacaca ataatatttg aggcaaatgg aaatctaata gcaccaatgt 900
atgctttcgc actgagtaga ggctttgggt ccggcatcat cacctcaaac gcatcaatgc 960
atgagtgtaa cacgaagtgt caaacacccc tgggagctat aaacagcagt ctcccttacc 1020
agaatataca cccagtcaca ataggagagt gcccaaaata cgtcaggagt gccaaattga 1080
ggatggttac aggactaagg aacactccgt ccattcaatc cagaggtcta tttggagcca 1140
ttgccggttt tattgaaggg ggatggactg gaatgataga tggatggtat ggttatcatc 1200
atcagaatga acagggatca ggctatgcag cggatcaaaa aagcacacaa aatgccatta 1260
acgggattac aaacaaggtg aacactgtta tcgagaaaat gaacattcaa ttcacagctg 1320
tgggtaaaga attcaacaaa ttagaaaaaa ggatggaaaa tttaaataaa aaagttgatg 1380
atggatttct ggacatttgg acatataatg cagaattgtt agttctactg gaaaatgaaa 1440
ggactctgga tttccatgac tcaaatgtga agaatctgta tgagaaagta aaaagccaat 1500
taaagaataa tgccaaagaa atcggaaatg gatgttttga gttctaccac aagtgtgaca 1560
atgaatgcat ggaaagtgta agaaatggga cttatgatta tcccaaatat tcagaagagt 1620

```
caaagttgaa cagggaaaag gtagatggag tgaaattgga atcaatgggg atctatcaga   1680

ttctggcgat ctactcaact gtcgcttcca gcctcgtctt gcttgttagt ctcggagcca   1740

tttccttttg gatgtgcagc aacggcagcc ttcaatgtag gatctgtatt tgaactctgt   1800

attctaccat tgcatcatcc gtcgtgcttg gctcgttgat aatagccgct tttctttggg   1860

ggtgccaaaa aggctcaatc caatgtaaaa tatgtatata gaacggtgga attaaccttg   1920

tcattcagaa aagcaaaaaa gacccttgtt tctact                             1956
```

```
<210> SEQ ID NO 32
<211> LENGTH: 1413
<212> TYPE: DNA
<213> ORGANISM: Influenza A virus
<220> FEATURE:
<221> NAME/KEY: misc_feature
<222> LOCATION: (1)..(1413)
<223> OTHER INFORMATION: Synthetic cDNA construct

<400> SEQUENCE: 32

agcgaaagca ggggtttaaa atgaatccaa atcagaaaat aacaaccatt ggatcaatct     60

gtctggtagt cggactaatt agcctaatat tgcaaatagg gaatataatc tcaatatgga    120

ttagccattc aattcaaact ggaagtcaaa accatactgg aatatgcaac caaaacatca    180

ttacctataa aaatagcacc tgggtaaagg acacaacttc agtgatatta accggcaatt    240

catctctttg tcccatccgt gggtgggcta tatacagcaa agacaatagc ataagaattg    300

gttccaaagg agacgttttt gtcataagag agccctttat ttcatgttct cacttggaat    360

gcaggacctt ttttctgacc caaggtgcct tactgaatga caagcattca aatgggactg    420

ttaaggacag aagcccttat agggccttaa tgagctgccc tgtcggtgaa gctccgtccc    480

cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc ggcaaagtga    840

tgtgtgtgtg cagagacaac tggcatggtt cgaaccggcc atgggtgtct ttcgatcaaa    900

acctggatta tcaaatagga tacatctgca gtggggtttt cggtgacaac ccgcgtcccg    960

aagatggaac aggcagctgt ggtccagtgt atgttgatgg agcaaacgga gtaaagggat   1020

tttcatatag gtatggtaat ggtgtttgga taggaaggac caaaagtcac agttccagac   1080

atgggtttga gatgatttgg gatcctaatg gatggacaga gactgatagt aagttctctg   1140

ttaggcaaga tgttgtggca atgactgatt ggtcagggta tagcggaagt ttcgttcaac   1200

atcctgagct aacagggcta gactgtatga ggccgtgctt ctgggttgaa ttaatcaggg   1260

gacgacctaa agaaaaaaca atctggacta gtgcgagcag catttctttt tgtggcgtga   1320

atagtgatac tgtagattgg tcttggccag acggtgctga gttgccattc agcattgaca   1380

agtagtctgt tcaaaaaact ccttgtttct act                                 1413
```

```
<210> SEQ ID NO 33
<211> LENGTH: 1766
<212> TYPE: DNA
<213> ORGANISM: Influenza A virus
<220> FEATURE:
<221> NAME/KEY: misc_feature
```

<222> LOCATION: (1)..(1766)
<223> OTHER INFORMATION: Synthetic cDNA construct

<400> SEQUENCE: 33
agcagaagca ggagttttta atactgtcta tcaacggaac gacctgtcta ctcacactca 60
gtctaatact cactgttata ctgatagggc tccaaatcct gctgcccttt attcttttct 120
ggaccaacag ccccccgcca gaaatctcca acagcactag ctgctgcaac ggaacctttc 180
tgactgaaac aaacaacaat ataaccatga atccaaatca gaaaataaca accattggat 240
caatctgtct ggtagtcgga ctaattagcc taatattgca aatagggaat ataatctcaa 300
tatggattag ccattcaatt caaactggaa gtcaaaacca tactggaata tgcaaccaaa 360
acatcattac ctataaaaat agcacctggg taaaggacac aacttcagtg atattaaccg 420
gcaattcatc tctttgtccc atccgtgggt gggctatata cagcaaagac aatagcataa 480
gaattggttc caaaggagac gtttttgtca taagagagcc ctttatttca tgttctcact 540
tggaatgcag gacctttttt ctgacccaag gtgccttact gaatgacaag cattcaaatg 600
ggactgttaa ggacagaagc ccttataggg ccttaatgag ctgccctgtc ggtgaagctc 660
cgtccccgta caattcaaga tttgaatcgg ttgcttggtc agcaagtgca tgtcatgatg 720
gcatgggctg gctaacaatc ggaatttcag gtccagataa tggagcagtg gctgtattaa 780
aatacaacgg cataataact gaaaccataa aaagttggag gaagaaaata ttgaggacac 840
aagagtctga atgtgcctgt gtaaatggtt catgttttac tataatgact gatggcccga 900
gtgatgggct ggcctcgtac aaaattttca agatcgaaaa ggggaaggtt actaaatcaa 960
tagagttgaa tgcacctaat tctcactatg aggaatgttc ctgttaccct gataccggca 1020
aagtgatgtg tgtgtgcaga gacaactggc atggttcgaa ccggccatgg gtgtctttcg 1080
atcaaaacct ggattatcaa ataggataca tctgcagtgg ggttttcggt gacaacccgc 1140
gtcccgaaga tggaacaggc agctgtggtc cagtgtatgt tgatggagca aacggagtaa 1200
agggattttc atataggtat ggtaatggtg tttggatagg aaggaccaaa agtcacagtt 1260
ccagacatgg gtttgagatg atttgggatc ctaatggatg gacagagact gatagtaagt 1320
tctctgttag gcaagatgtt gtggcaatga ctgattggtc agggtatagc ggaagtttcg 1380
ttcaacatcc tgagctaaca gggctagact gtatgaggcc gtgcttctgg gttgaattaa 1440
tcaggggacg acctaaagaa aaaacaatct ggactagtgc gagcagcatt tctttttgtg 1500
gcgtgaatag tgatactgta gattggtctt ggccagacgg tgctgagttg ccattcagca 1560
ttgacaagta gattctttca acccaaagga gacctcattt ctggatgcca acgaatctgt 1620
ttctggctgg aaatagaaga tcaaacagta ggcctaggaa tgattcaaga actcagcact 1680
ttctgtggga taaactcacc tgttcagaat ataaattggg attcatgacc aatggacagc 1740
gaatgaaaaa actccttgtt tctact 1766

<210> SEQ ID NO 34
<211> LENGTH: 1766
<212> TYPE: DNA
<213> ORGANISM: Influenza A virus
<220> FEATURE:
<221> NAME/KEY: misc_feature
<222> LOCATION: (1)..(1766)
<223> OTHER INFORMATION: Synthetic cDNA construct

<400> SEQUENCE: 34
agcagaagca ggagttttta atactgtcta tcaacggaac gacctgtcta ctcacactca 60

-continued gtctaatact cactgttata ctgatagggc tccaaatcct gctgcccttt attcttttct 120
ggaccaacag ccccccgcca gaaatctcca acagcactag ctgctgcaac ggaacctttc 180
tgactgaaac aaacaacaat ataaccatga accccaacca aaagatcacc actatcggca 240
gcatttgcct cgtggttggg ttgatctctt tgatcctcca gattggaaac atcattagca 300
tctggatctc tcattcaatt caaactggaa gtcaaaacca tactggaata tgcaaccaaa 360
acatcattac ctataaaaat agcacctggg taaaggacac aacttcagtg atattaaccg 420
gcaattcatc tctttgtccc atccgtgggt gggctatata cagcaaagac aatagcataa 480
gaattggttc caaaggagac gtttttgtca taagagagcc ctttatttca tgttctcact 540
tggaatgcag gacctttttt ctgacccaag gtgccttact gaatgacaag cattcaaatg 600
ggactgttaa ggacagaagc ccttataggg ccttaatgag ctgccctgtc ggtgaagctc 660
cgtccccgta caattcaaga tttgaatcgg ttgcttggtc agcaagtgca tgtcatgatg 720
gcatgggctg gctaacaatc ggaatttcag gtccagataa tggagcagtg gctgtattaa 780
aatacaacgg cataataact gaaaccataa aaagttggag gaagaaaata ttgaggacac 840
aagagtctga atgtgcctgt gtaaatggtt catgttttac tataatgact gatggcccga 900
gtgatgggct ggcctcgtac aaaattttca agatcgaaaa ggggaaggtt actaaatcaa 960
tagagttgaa tgcacctaat tctcactatg aggaatgttc ctgttaccct gataccggca 1020
aagtgatgtg tgtgtgcaga gacaactggc atggttcgaa ccggccatgg gtgtctttcg 1080
atcaaaacct ggattatcaa ataggataca tctgcagtgg ggttttcggt gacaacccgc 1140
gtcccgaaga tggaacaggc agctgtggtc cagtgtatgt tgatggagca aacggagtaa 1200
agggattttc atataggtat ggtaatggtg tttggatagg aaggaccaaa agtcacagtt 1260
ccagacatgg gtttgagatg atttgggatc ctaatggatg gacagagact gatagtaagt 1320
tctctgttag gcaagatgtt gtggcaatga ctgattggtc agggtatagc ggaagtttcg 1380
ttcaacatcc tgagctaaca gggctagact gtatgaggcc gtgcttctgg gttgaattaa 1440
tcaggggacg acctaaagaa aaaacaattt ggacctccgc atcttcaatc agcttctgcg 1500
gagttaactc cgacaccgtg gactggagct ggcccgatgg cgccgaactc cctttttcaa 1560
tcgataaata gattctttca acccaaagga gacctcattt ctggatgcca acgaatctgt 1620
ttctggctgg aaatagaaga tcaaacagta ggcctaggaa tgattcaaga actcagcact 1680
ttctgtggga taaactcacc tgttcagaat ataaattggg attcatgacc aatggacagc 1740
gaatgaaaaa actccttgtt tctact 1766

<210> SEQ ID NO 35
<211> LENGTH: 18
<212> TYPE: DNA
<213> ORGANISM: Artificial Sequence
<220> FEATURE:
<223> OTHER INFORMATION: Synthetic primer construct

<400> SEQUENCE: 35 gggggagca gaagcagg 18

<210> SEQ ID NO 36
<211> LENGTH: 22
<212> TYPE: DNA
<213> ORGANISM: Artificial Sequence
<220> FEATURE:
<223> OTHER INFORMATION: Synthetic primer construct

<400> SEQUENCE: 36
cgggttatta gtagaaacaa gg 22

<210> SEQ ID NO 37
<211> LENGTH: 12
<212> TYPE: DNA
<213> ORGANISM: Artificial Sequence
<220> FEATURE:
<223> OTHER INFORMATION: Synthetic primer construct

<400> SEQUENCE: 37
agcagaagca gg 12

<210> SEQ ID NO 38
<211> LENGTH: 12
<212> TYPE: DNA
<213> ORGANISM: Artificial Sequence
<220> FEATURE:
<223> OTHER INFORMATION: Synthetic primer construct

<400> SEQUENCE: 38
agcraaagca gg 12

<210> SEQ ID NO 39
<211> LENGTH: 760
<212> TYPE: PRT
<213> ORGANISM: Influenza A virus
<220> FEATURE:
<221> NAME/KEY: MISC_FEATURE
<222> LOCATION: (1)..(760)
<223> OTHER INFORMATION: H17N10 PB2 viral protein

<400> SEQUENCE: 39

```
Met Glu Arg Ile Lys Glu Leu Leu Glu Met Val Lys Asn Ser Arg Met
1               5                   10                  15

Arg Glu Ile Leu Thr Thr Thr Ser Val Asp His Met Ala Val Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Ser Ala Ser Ser Arg Ile Arg
    50                  55                  60

Glu Met Ile Pro Glu Lys Asp Glu Asp Gly Asn Thr Leu Trp Thr Asn
65                  70                  75                  80

Thr Lys Asp Ala Gly Ser Asn Arg Val Leu Val Ser Pro Asn Ala Val
                85                  90                  95

Thr Trp Trp Asn Arg Ala Gly Pro Val Ser Asp Val Val His Tyr Pro
            100                 105                 110

Arg Val Tyr Lys Met Tyr Phe Asp Arg Leu Glu Arg Leu Thr His Gly
        115                 120                 125

Thr Phe Gly Pro Val Lys Phe Tyr Asn Gln Val Lys Val Arg Lys Arg
    130                 135                 140

Val Asp Ile Asn Pro Gly His Lys Asp Leu Thr Ser Arg Glu Ala Gln
145                 150                 155                 160

Glu Val Ile Met Glu Val Val Phe Pro Asn Glu Val Gly Ala Arg Thr
                165                 170                 175

Leu Ser Ser Asp Ala Gln Leu Thr Ile Thr Lys Glu Lys Lys Glu Glu
            180                 185                 190

Leu Lys Asn Cys Lys Ile Ser Pro Ile Met Val Ala Tyr Met Leu Glu
        195                 200                 205

Arg Glu Leu Val Arg Arg Thr Arg Phe Leu Pro Ile Ala Gly Ala Thr
```

-continued

```
    210                 215                 220

Ser Ser Thr Tyr Val Glu Val Leu His Leu Thr Gln Gly Thr Cys Trp
225                 230                 235                 240

Glu Gln Gln Tyr Thr Pro Gly Gly Glu Ala Glu Asn Asp Asp Leu Asp
                245                 250                 255

Gln Thr Leu Ile Ile Ala Ser Arg Asn Ile Val Arg Arg Ser Ile Val
            260                 265                 270

Ala Ile Asp Pro Leu Ala Ser Leu Leu Ser Met Cys His Thr Thr Ser
        275                 280                 285

Ile Ser Ser Glu Pro Leu Val Glu Ile Leu Arg Ser Asn Pro Thr Asp
    290                 295                 300

Glu Gln Ala Val Asn Ile Cys Lys Ala Ala Leu Gly Ile Arg Ile Asn
305                 310                 315                 320

Asn Ser Phe Ser Phe Gly Gly Tyr Asn Phe Lys Arg Val Lys Gly Ser
                325                 330                 335

Ser Gln Arg Thr Glu Lys Ala Val Leu Thr Gly Asn Leu Gln Thr Leu
            340                 345                 350

Thr Met Thr Ile Phe Glu Gly Tyr Glu Glu Phe Asn Val Ser Gly Lys
        355                 360                 365

Arg Ala Ser Ala Val Leu Lys Lys Gly Thr Gln Arg Leu Ile Gln Ala
    370                 375                 380

Ile Ile Gly Gly Arg Thr Leu Glu Asp Ile Leu Asn Leu Met Ile Thr
385                 390                 395                 400

Leu Met Val Phe Ser Gln Glu Glu Lys Met Leu Lys Ala Val Arg Gly
                405                 410                 415

Asp Leu Asn Phe Val Asn Arg Ala Asn Gln Arg Leu Asn Pro Met Tyr
            420                 425                 430

Gln Leu Leu Arg His Phe Gln Lys Asp Ser Ser Thr Leu Leu Arg Asn
        435                 440                 445

Trp Gly Thr Glu Glu Ile Asp Pro Ile Met Gly Ile Ala Gly Ile Met
    450                 455                 460

Pro Asp Gly Thr Ile Asn Lys Asn Gln Thr Leu Ile Gly Val Arg Leu
465                 470                 475                 480

Ser Gln Gly Gly Val Asp Glu Tyr Ser Phe Asn Glu Arg Ile Arg Val
                485                 490                 495

Asn Ile Asp Lys Tyr Leu Arg Val Arg Asn Glu Lys Gly Glu Leu Leu
            500                 505                 510

Ile Ser Pro Glu Glu Val Ser Glu Ala Gln Gly Gln Glu Lys Leu Pro
        515                 520                 525

Ile Asn Tyr Asn Ser Ser Leu Met Trp Glu Val Asn Gly Pro Glu Ser
    530                 535                 540

Ile Leu Thr Asn Thr Tyr His Trp Ile Ile Lys Asn Trp Glu Leu Leu
545                 550                 555                 560

Lys Thr Gln Trp Met Thr Asp Pro Thr Val Leu Tyr Asn Arg Met Glu
                565                 570                 575

Phe Glu Pro Phe Gln Thr Leu Ile Pro Lys Gly Asn Arg Ala Thr Tyr
            580                 585                 590

Ser Gly Phe Thr Arg Thr Leu Phe Gln Gln Met Arg Asp Val Glu Gly
        595                 600                 605

Thr Phe Asp Ser Ile Gln Val Ile Lys Leu Leu Pro Phe Ser Ala His
    610                 615                 620

Pro Pro Ser Leu Gly Arg Thr Gln Phe Ser Ser Phe Thr Leu Asn Ile
625                 630                 635                 640
```

```
Arg Gly Ala Pro Leu Arg Leu Leu Ile Arg Gly Asn Ser Gln Val Phe
                645                 650                 655

Asn Tyr Asn Gln Met Glu Asn Val Ile Ile Val Leu Gly Lys Ser Val
            660                 665                 670

Gly Ser Pro Glu Arg Ser Ile Leu Thr Glu Ser Ser Ser Ile Glu Ser
        675                 680                 685

Ala Val Leu Arg Gly Phe Leu Ile Leu Gly Lys Ala Asn Ser Lys Tyr
    690                 695                 700

Gly Pro Val Leu Thr Ile Gly Glu Leu Asp Lys Leu Gly Arg Gly Glu
705                 710                 715                 720

Lys Ala Asn Val Leu Ile Gly Gln Gly Asp Thr Val Leu Val Met Lys
                725                 730                 735

Arg Lys Arg Asp Ser Ser Ile Leu Thr Asp Ser Gln Thr Ala Leu Lys
            740                 745                 750

Arg Ile Arg Leu Glu Glu Ser Lys
        755                 760


<210> SEQ ID NO 40
<211> LENGTH: 756
<212> TYPE: PRT
<213> ORGANISM: Influenza A virus
<220> FEATURE:
<221> NAME/KEY: MISC_FEATURE
<222> LOCATION: (1)..(756)
<223> OTHER INFORMATION: H17N10 PB1 Viral protein

<400> SEQUENCE: 40

Met Asp Val Asn Pro Met Leu Ile Phe Leu Lys Val Pro Val Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Ile Arg Thr His Asp
        35                  40                  45

Tyr Ser Ser Arg Gly Ile Trp Lys Thr Asn Ser Glu Thr Gly Ala Gln
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Leu Ile Glu Arg Leu Asp
                85                  90                  95

Arg Ser His Pro Gly Leu Phe Glu Thr Ala Cys Gln Glu Thr Ile Asp
            100                 105                 110

Ala Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Lys Asn Gly His Lys Leu Asn Glu Ser
145                 150                 155                 160

Gly Arg Leu Ile Asp Phe Leu Lys Asp Val Leu Leu Ser Phe Glu Asn
                165                 170                 175

Asn Ser Met Glu Val Thr Thr His Phe Gln Lys Lys Lys Arg Ile Arg
            180                 185                 190

Asp Asn His Thr Lys Lys Met Ile Thr Gln Arg Thr Ile Gly Lys Lys
        195                 200                 205

Arg Val Lys Leu Thr Lys Lys Asn Tyr Leu Ile Arg Ala Leu Thr Leu
    210                 215                 220
```

-continued

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Leu Leu Ala Arg Asn Ile Cys Glu Arg Leu Glu Gln Ser Gly Leu Pro
            260                 265                 270

Val Gly Gly Asn Glu Lys Lys Ala Lys Leu Ala Asn Val Ile Lys Lys
        275                 280                 285

Met Met Ala Lys Ser Thr Asp Glu Glu Leu Ser Tyr Thr Ile Thr Gly
    290                 295                 300

Asp Asn Thr Lys Trp Asn Glu Asn Gln Asn Pro Arg Ile Phe Leu Ala
305                 310                 315                 320

Met Val Leu Lys Ile Thr Ala Gly Gln Pro Glu Trp Phe Arg Asp Leu
                325                 330                 335

Leu Ala Val Ala Pro Ile Met Phe Ser Asn Lys Val Ala Arg Leu Gly
            340                 345                 350

Arg Gly Tyr Met Phe Glu Ser Lys Ser Met His Leu Arg Thr Gln Ile
        355                 360                 365

Ser Ala Glu Asn Leu Ser Asp Ile Asn Leu Arg Tyr Phe Asn Glu Asp
    370                 375                 380

Thr Lys Lys Lys Ile Glu Lys Ile Arg His Leu Met Val Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Leu Gly Gln Arg Glu Ile Leu
            420                 425                 430

Lys Arg Thr Tyr Trp Trp Asp Gly Leu Gln Ser Ser Asp Asp Phe Ala
        435                 440                 445

Leu Ile Ile Asn Gly His Phe Lys Glu Asp Ile Gln Gln Gly Val Asn
    450                 455                 460

His Phe Tyr Arg Thr Cys Lys Leu Val Gly Ile Asn Met Ser Gln Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ala Gly Asn Asn Glu Ser Ala Asp Met Ser Ile Gly Thr Thr
        515                 520                 525

Val Ile Lys Thr Asn Met Ile Asn Asn Asp Leu Gly Pro Ala Thr Ala
    530                 535                 540

Gln Met Ala Ile Gln Leu Phe Ile Lys Asp Tyr Arg Tyr Thr Tyr Arg
545                 550                 555                 560

Cys His Arg Gly Asp Thr Asn Leu Glu Thr Arg Arg Thr Lys Ser Ile
                565                 570                 575

Lys Arg Leu Trp Thr Glu Thr Ile Ser Lys Ala Gly Leu Leu Val Ala
            580                 585                 590

Asp Gly Gly Pro Asn Pro Tyr Asn Leu Arg Asn Leu His Ile Pro Glu
        595                 600                 605

Val Cys Leu Lys Trp Asp Leu Met Asp Pro Asp Tyr Arg Gly Arg Leu
    610                 615                 620

Cys Asn Pro Asn Asn Pro Phe Val His His Met Glu Val Glu Ser Thr
625                 630                 635                 640

Asn Leu Ala Val Val Met Pro Ala His Gly Pro Ala Lys Ser Leu Glu
```

```
                645                 650                 655

Tyr Asp Ala Val Ala Thr Thr His Ser Trp Thr Pro Lys Arg Asn Arg
            660                 665                 670

Ser Ile Leu Asn Thr Asn Gln Arg Gly Ile Leu Glu Asp Glu Lys Ile
        675                 680                 685

Tyr Gln Lys Cys Cys Gln Ile Phe Glu Lys Phe Phe Pro Ser Ser Thr
    690                 695                 700

Tyr Arg Arg Pro Ile Gly Met Ala Ser Met Leu Asp Ala Met Leu Ser
705                 710                 715                 720

Arg Ala Arg Ile Asp Ala Arg Ile Asp Leu Glu Ser Gly Arg Ile Ser
                725                 730                 735

Ser Gln Asp Phe Ser Glu Ile Thr Asn Thr Cys Lys Ala Ile Glu Ala
            740                 745                 750

Leu Lys Arg Gln
        755


<210> SEQ ID NO 41
<211> LENGTH: 713
<212> TYPE: PRT
<213> ORGANISM: Influenza A virus
<220> FEATURE:
<221> NAME/KEY: MISC_FEATURE
<222> LOCATION: (1)..(713)
<223> OTHER INFORMATION: H17N10 PA Viral protein

<400> SEQUENCE: 41

Met Glu Asn Phe Val Arg Thr Asn Phe Asn Pro Met Ile Leu Glu Arg
1               5                   10                  15

Ala Glu Lys Thr Met Lys Glu Tyr Gly Glu Asn Pro Gln Asn Glu Gly
            20                  25                  30

Asn Lys Phe Ala Ala Ile Ser Thr His Met Glu Val Cys Phe Met Tyr
        35                  40                  45

Ser Asp Phe His Phe Ile Asp Leu Glu Gly Asn Thr Ile Val Lys Glu
    50                  55                  60

Ser Asp Asp Asp Asn Ala Met Leu Lys His Arg Phe Glu Ile Ile Glu
65                  70                  75                  80

Gly Gln Glu Arg Asn Ile Ala Trp Thr Ile Val Asn Ser Ile Cys Asn
                85                  90                  95

Met Thr Glu Asn Ser Lys Pro Arg Phe Leu Pro Asp Leu Tyr Asp Tyr
            100                 105                 110

Lys Thr Asn Lys Phe Ile Glu Ile Gly Val Thr Arg Arg Lys Val Glu
        115                 120                 125

Asp Tyr Tyr Tyr Glu Lys Ala Ser Lys Leu Lys Gly Glu Asn Val Tyr
    130                 135                 140

Ile His Ile Phe Ser Phe Asp Gly Glu Glu Met Ala Thr Asp Asp Glu
145                 150                 155                 160

Tyr Ile Leu Asp Glu Glu Ser Arg Ala Arg Ile Lys Thr Arg Leu Phe
                165                 170                 175

Val Leu Arg Gln Glu Leu Ala Thr Ala Gly Leu Trp Asp Ser Phe Arg
            180                 185                 190

Gln Ser Glu Lys Gly Glu Glu Thr Leu Glu Glu Glu Phe Ser Tyr Pro
        195                 200                 205

Pro Thr Phe Gln Arg Leu Ala Asn Gln Ser Leu Pro Pro Ser Phe Lys
    210                 215                 220

Asp Tyr His Gln Phe Lys Ala Tyr Val Ser Ser Phe Lys Ala Asn Gly
225                 230                 235                 240
```

-continued

```
Asn Ile Glu Ala Lys Leu Gly Ala Met Ser Glu Glu Val Asn Ala Gln
                245                 250                 255

Ile Glu Asn Phe Asp Pro Arg Thr Ile Arg Glu Leu Glu Leu Pro Glu
            260                 265                 270

Gly Lys Ser Cys Thr Gln Arg Ser Lys Phe Leu Leu Met Asp Ala Met
        275                 280                 285

Lys Leu Ser Val Leu Asn Pro Ala His Glu Gly Glu Gly Ile Pro Met
    290                 295                 300

Lys Asp Ala Lys Ala Cys Leu Asp Thr Phe Trp Gly Trp Lys Lys Ala
305                 310                 315                 320

Thr Val Ile Lys Lys His Glu Lys Gly Val Asn Thr Asn Tyr Leu Met
                325                 330                 335

Ile Trp Glu Gln Leu Leu Glu Ser Ile Lys Glu Val Glu Gly Lys Phe
            340                 345                 350

Leu Asn Leu Arg Lys Thr Asn His Leu Lys Trp Gly Leu Gly Glu Gly
        355                 360                 365

Gln Ala Pro Glu Lys Met Asp Phe Glu Asp Cys Lys Glu Val Pro Asp
    370                 375                 380

Leu Phe Gln Tyr Lys Ser Glu Pro Pro Glu Lys Arg Lys Leu Ala Ser
385                 390                 395                 400

Trp Ile Gln Ser Glu Phe Asn Lys Ala Ser Glu Leu Thr Asn Ser Asn
                405                 410                 415

Trp Ile Glu Phe Asp Glu Leu Gly Asn Asp Val Ala Pro Ile Glu His
            420                 425                 430

Ile Ala Ser Arg Arg Arg Asn Phe Phe Thr Ala Glu Val Ser Gln Cys
        435                 440                 445

Arg Ala Ser Glu Tyr Ile Met Lys Ala Val Tyr Ile Asn Thr Ala Leu
    450                 455                 460

Leu Asn Ser Ser Cys Thr Ala Met Glu Glu Tyr Gln Val Ile Pro Ile
465                 470                 475                 480

Ile Thr Lys Cys Arg Asp Thr Ser Gly Gln Arg Arg Thr Asn Leu Tyr
                485                 490                 495

Gly Phe Ile Ile Lys Gly Arg Ser His Leu Arg Asn Asp Thr Asp Val
            500                 505                 510

Val Asn Phe Ile Ser Leu Glu Phe Ser Leu Thr Asp Pro Arg Asn Glu
        515                 520                 525

Ile His Lys Trp Glu Lys Tyr Cys Val Leu Glu Ile Gly Asp Met Glu
    530                 535                 540

Ile Arg Thr Ser Ile Ser Thr Ile Met Lys Pro Val Tyr Leu Tyr Ile
545                 550                 555                 560

Arg Thr Asn Gly Thr Ser Lys Ile Lys Met Lys Trp Gly Met Glu Met
                565                 570                 575

Arg Arg Cys Leu Leu Gln Ser Leu Gln Gln Val Glu Ser Met Ile Glu
            580                 585                 590

Ala Glu Ser Ala Val Lys Glu Lys Asp Met Thr Glu Pro Phe Phe Arg
        595                 600                 605

Asn Arg Glu Asn Asp Trp Pro Ile Gly Glu Ser Pro Gln Gly Ile Glu
    610                 615                 620

Lys Gly Thr Ile Gly Lys Val Cys Arg Val Leu Leu Ala Lys Ser Val
625                 630                 635                 640

Phe Asn Ser Ile Tyr Ala Ser Ala Gln Leu Glu Gly Phe Ser Ala Glu
                645                 650                 655
```

```
Ser Arg Lys Leu Leu Leu Leu Ile Gln Ala Phe Arg Asp Asn Leu Asp
            660                 665                 670

Pro Gly Thr Phe Asp Leu Lys Gly Leu Tyr Glu Ala Ile Glu Glu Cys
        675                 680                 685

Ile Ile Asn Asp Pro Trp Val Leu Leu Asn Ala Ser Trp Phe Asn Ser
    690                 695                 700

Phe Leu Lys Ala Val Gln Leu Ser Met
705                 710


<210> SEQ ID NO 42
<211> LENGTH: 122
<212> TYPE: PRT
<213> ORGANISM: Influenza A virus
<220> FEATURE:
<221> NAME/KEY: MISC_FEATURE
<222> LOCATION: (1)..(122)
<223> OTHER INFORMATION: H17N10 NS2 Viral protein

<400> SEQUENCE: 42

Met Glu Pro Asn Pro Thr Thr Ile Ala Phe Gln Asp Ile Leu Glu Arg
1               5                   10                  15

Met Ser Lys Leu His Met Asn Ser Ser Glu Val Asp Leu Asn Gly Met
            20                  25                  30

Ile Thr Gln Leu Thr Asn Leu Arg Phe Tyr Arg Asp Ser Leu Gly Glu
        35                  40                  45

Ser Leu Met Arg Thr Gly Asp Tyr Arg Lys Met Ala Gln Gln Asn Asn
    50                  55                  60

Asn Trp Arg Leu Gln Leu Gly Glu Lys Leu Thr Ile Ile Arg Asn Leu
65                  70                  75                  80

Ile Gln Thr Cys Arg Glu Val Leu Met Thr Ser Ser Asn Ser Phe Val
                85                  90                  95

Glu Ile Thr Phe Leu Ala Ala Leu Asp Leu Leu Leu Glu Val Glu Arg
            100                 105                 110

Glu Met Arg Thr Leu Ala Phe Gln Leu Ile
        115                 120


<210> SEQ ID NO 43
<211> LENGTH: 760
<212> TYPE: PRT
<213> ORGANISM: Influenza A virus
<220> FEATURE:
<221> NAME/KEY: MISC_FEATURE
<222> LOCATION: (1)..(760)
<223> OTHER INFORMATION: H18N11 PB2 Viral protein

<400> SEQUENCE: 43

Met Asp Arg Ile Lys Glu Leu Leu Glu Met Thr Lys Asn Ser Arg Met
1               5                   10                  15

Arg Glu Ile Leu Ser Thr Thr Ser Val Asp His Met Ala Val Ile Arg
            20                  25                  30

Lys Tyr Thr Ser Gly Arg Gln Glu Lys Asn Pro Ala Leu Arg Met Lys
        35                  40                  45

Trp Met Met Ala Met Lys Phe Pro Ile Ser Ala Ser Ala Lys Ile Lys
    50                  55                  60

Glu Leu Ile Pro Glu Lys Asp Glu Asp Gly Asn Val Leu Trp Thr Asn
65                  70                  75                  80

Thr Lys Asp Ala Gly Ser Asn Arg Leu Leu Val Ser Pro Asn Ala Val
                85                  90                  95

Thr Trp Trp Asn Arg Ala Gly Pro Ile Ser Glu Val Val His Tyr Pro
```

-continued

```
            100                 105                 110

Lys Val Tyr Lys Met Tyr Phe Asp Arg Leu Asp Arg Leu Gln Asn Gly
        115                 120                 125

Thr Tyr Gly Pro Val Lys Phe Tyr Asn Gln Met Lys Ile Arg Lys Arg
    130                 135                 140

Val Asp Ile Asn Pro Gly His Lys Asp Leu Thr Ser Lys Glu Ala Gln
145                 150                 155                 160

Asp Val Ile Met Glu Val Val Phe Pro Asn Glu Val Gly Ala Arg Thr
                165                 170                 175

Leu Ser Ser Asp Ala Gln Leu Ala Ile Thr Lys Glu Lys Lys Gln Glu
            180                 185                 190

Leu Gln Asn Cys Lys Ile Ser Pro Ile Met Val Ala Tyr Met Leu Glu
        195                 200                 205

Arg Glu Leu Val Arg Lys Thr Arg Phe Leu Pro Val Ala Gly Ala Thr
    210                 215                 220

Ser Ser Thr His Val Glu Val Leu His Leu Thr Gln Gly Thr Cys Trp
225                 230                 235                 240

Glu Gln Gln Tyr Thr Pro Gly Gly Glu Ala Glu Asn Asp Asp Met Asp
                245                 250                 255

Gln Thr Leu Ile Ile Ala Ala Arg Asn Ile Val Arg Arg Ser Ile Val
            260                 265                 270

Ala Ile Asp Pro Leu Ala Ser Leu Ile Ser Met Cys His Thr Thr Asn
        275                 280                 285

Ile Ser Ala Glu Pro Leu Thr Glu Ile Leu Lys Ala Asn Pro Thr Asp
    290                 295                 300

Glu Gln Ala Val Asn Ile Cys Lys Ala Ala Leu Gly Ile Lys Ile Asn
305                 310                 315                 320

Asn Ser Phe Ser Phe Gly Gly Tyr Asn Phe Lys Lys Ile Lys Gly Asn
                325                 330                 335

Ser Lys Arg Ser Glu Gln Gln Val Leu Thr Gly Asn Leu Gln Thr Leu
            340                 345                 350

Thr Leu Thr Ile Phe Glu Gly Tyr Glu Glu Phe Asn Val Ser Gly Lys
        355                 360                 365

Arg Ala Ser Ala Val Leu Lys Lys Gly Thr Gln Arg Leu Ile Gln Ala
    370                 375                 380

Ile Ile Gly Gly Arg Thr Ile Glu Asp Ile Leu Asn Leu Met Ile Thr
385                 390                 395                 400

Leu Met Val Phe Ser Gln Glu Asp Lys Met Ile Lys Ser Val Arg Gly
                405                 410                 415

Asp Leu Asn Phe Leu Asn Arg Ala Asn Gln Arg Leu His Pro Met Tyr
            420                 425                 430

Gln Leu Leu Arg His Phe Gln Lys Asp Ser Gly Val Leu Leu Arg Asn
        435                 440                 445

Trp Gly Met Glu Asp Ile Asp Pro Val Met Gly Ile Met Gly Ile Leu
    450                 455                 460

Pro Asp Gly Thr Ile Asn Arg Asn Thr Thr Leu Val Gly Val Arg Ile
465                 470                 475                 480

Ser Gln Gly Gly Val Asp Glu Tyr Ser Phe Asn Glu Arg Ile Arg Val
                485                 490                 495

Ser Ile Asp Lys Tyr Leu Arg Val Lys Asn Glu Lys Gly Glu Leu Leu
            500                 505                 510

Ile Ser Pro Glu Glu Val Ser Glu Ala Gln Gly Gln Glu Lys Leu Pro
        515                 520                 525
```

```
Ile Asn Tyr Asn Ser Ser Leu Met Trp Glu Val Asn Gly Pro Glu Ser
    530                 535                 540

Ile Leu Thr Asn Thr Tyr His Trp Ile Leu Lys Asn Trp Glu Ile Leu
545                 550                 555                 560

Lys Thr Gln Trp Met Thr Thr Pro Asn Ile Leu Tyr Asn Arg Met Glu
                565                 570                 575

Phe Glu Pro Phe Gln Thr Leu Ile Pro Lys Gly Asn Arg Ala Ala Tyr
            580                 585                 590

Ser Gly Phe Thr Arg Thr Leu Phe Gln Gln Met Arg Asp Val Glu Gly
        595                 600                 605

Thr Phe Asp Ser Ile Gln Ile Ile Lys Leu Leu Pro Phe Ala Ala His
    610                 615                 620

Pro Pro Ser Ala Gly Arg Ser Gln Phe Ser Ser Phe Thr Ile Asn Ile
625                 630                 635                 640

Arg Gly Ala Pro Leu Arg Leu Leu Ile Arg Gly Asn Ser Gln Ile Phe
                645                 650                 655

Asn Tyr Asn Lys Met Glu Asn Ser Ile Ile Ile Leu Gly Lys Asn Val
            660                 665                 670

Gly Lys Leu Asp Glu Ser Ile Ile Thr Glu Thr Asn Thr Ile Glu Ser
        675                 680                 685

Ala Val Leu Arg Gly Phe Leu Ile Leu Gly Lys Ala Asn Ser Lys Tyr
    690                 695                 700

Gly Pro Val Leu Thr Ile Ala Glu Leu Asp Lys Leu Gly Arg Gly Glu
705                 710                 715                 720

Lys Ala Asn Val Leu Ile Gly Gln Gly Asp Thr Val Leu Val Met Lys
                725                 730                 735

Arg Lys Arg Asp Ser Ser Ile Leu Thr Asp Ser Gln Thr Ala Ile Lys
            740                 745                 750

Arg Ile Arg Leu Glu Glu Ser Lys
        755                 760
```

<210> SEQ ID NO 44
<211> LENGTH: 756
<212> TYPE: PRT
<213> ORGANISM: Influenza A virus
<220> FEATURE:
<221> NAME/KEY: MISC_FEATURE
<222> LOCATION: (1)..(756)
<223> OTHER INFORMATION: H18N11 PB1 Viral protein

<400> SEQUENCE: 44

```
Met Asp Val Asn Pro Met Leu Ile Phe Leu Lys Val Pro Val Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Ile Arg Thr His Glu
        35                  40                  45

Tyr Ser Asn Lys Gly Val Trp Thr Thr Asn Ser Glu Thr Ser Ala Ile
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Leu Ile Glu Lys Leu Gly
                85                  90                  95

Glu Ser His Pro Gly Leu Phe Asn Ile Ala Cys Gln Glu Thr Ile Asp
            100                 105                 110
```

```
Ser Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Lys Asn Gly Tyr Thr Ala Asn Glu Ser
145                 150                 155                 160

Gly Arg Leu Ile Asp Phe Leu Lys Asp Val Leu Ile Ser Phe Glu Lys
                165                 170                 175

Glu Ser Met Glu Ile Val Thr His Tyr Gln Lys Lys Lys Arg Ile Arg
            180                 185                 190

Asp Asn His Thr Lys Arg Met Val Thr Gln Arg Thr Ile Gly Lys Arg
        195                 200                 205

Lys Thr Lys Leu Ser Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Leu Leu Ala Arg Asn Ile Cys Glu Arg Leu Glu Gln Ser Gly Leu Pro
            260                 265                 270

Val Gly Gly Asn Glu Lys Lys Ala Lys Leu Ala Asn Val Ile Lys Lys
        275                 280                 285

Met Met Ala Lys Ser Ser Asp Glu Glu Leu Ser Tyr Thr Ile Thr Gly
    290                 295                 300

Asp Asn Thr Lys Trp Asn Glu Asn Gln Asn Pro Arg Ile Phe Leu Ala
305                 310                 315                 320

Met Ile Leu Lys Ile Thr Glu Gly Gln Pro Glu Trp Phe Arg Asp Leu
                325                 330                 335

Leu Ala Val Ala Pro Ile Met Phe Ser Asn Lys Val Ala Arg Leu Gly
            340                 345                 350

Arg Gly Tyr Met Phe Glu Ser Lys Ser Met Lys Val Arg Thr Gln Ile
        355                 360                 365

Pro Ala Glu Glu Leu Asn Thr Ile Ser Leu Lys Tyr Phe Asn Glu Glu
    370                 375                 380

Thr Lys Lys Lys Ile Glu Lys Val Arg Asn Leu Met Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Val Leu Asn Ile Gly Gln Lys Gln Met Leu
            420                 425                 430

Lys Thr Thr Tyr Trp Trp Asp Gly Leu Gln Ser Ser Asp Asp Phe Ala
        435                 440                 445

Leu Ile Val Asn Gly His Phe Lys Asn Asp Ile Gln Gln Gly Val Asn
    450                 455                 460

His Phe Tyr Arg Ile Cys Lys Leu Val Gly Ile Asn Met Ser Gln Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ala Gly Asn Asn Glu Ser Ala Asp Met Ser Ile Gly Thr Thr
        515                 520                 525

Val Ile Lys Thr Asn Met Ile Asn Asn Asp Leu Gly Pro Ala Thr Ala
```

```
    530                 535                 540

Gln Met Ala Ile Gln Leu Phe Ile Lys Asp Tyr Arg Tyr Thr Tyr Arg
545                 550                 555                 560

Cys His Arg Gly Asp Thr Asn Leu Glu Thr Arg Arg Thr Lys Ser Leu
                565                 570                 575

Lys Arg Leu Trp Thr Glu Thr Ile Ser Lys Ser Gly Leu Leu Val Ser
            580                 585                 590

Asp Gly Gly Pro Asn Pro Tyr Asn Leu Arg Asn Leu His Ile Pro Glu
        595                 600                 605

Val Cys Leu Lys Trp His Leu Met Asp Pro Glu Tyr Arg Gly Arg Leu
    610                 615                 620

Cys Asn Pro Asn Asn Pro Phe Val His His Met Glu Val Glu Ser Thr
625                 630                 635                 640

Asn Leu Ala Val Ile Met Pro Ala His Gly Pro Ala Lys Ser Met Glu
                645                 650                 655

Tyr Asp Ala Val Ala Thr Thr His Ser Trp Thr Pro Lys Arg Asn Arg
            660                 665                 670

Ser Ile Leu Asn Thr Asn Gln Arg Gly Ile Leu Glu Asp Glu Arg Ile
        675                 680                 685

Tyr Gln Lys Cys Cys Gln Ile Phe Glu Lys Phe Phe Pro Ser Ser Ser
    690                 695                 700

Tyr Arg Arg Pro Ile Gly Met Ala Ser Met Leu Asp Ala Met Leu Ser
705                 710                 715                 720

Arg Ala Lys Ile Asp Ala Arg Ile Asp Leu Glu Ser Gly Arg Leu Ser
                725                 730                 735

Asn Gln Asp Phe Ser Glu Ile Met Asn Ile Cys Lys Ala Ile Glu Asn
            740                 745                 750

Leu Lys Arg Arg
        755


<210> SEQ ID NO 45
<211> LENGTH: 713
<212> TYPE: PRT
<213> ORGANISM: Influenza A virus
<220> FEATURE:
<221> NAME/KEY: MISC_FEATURE
<222> LOCATION: (1)..(713)
<223> OTHER INFORMATION: H18N11 PA Viral protein

<400> SEQUENCE: 45

Met Glu Asn Phe Ile Arg Ala Asn Phe Asn Pro Met Ile Leu Glu Arg
1               5                   10                  15

Ala Glu Lys Ser Met Lys Glu Tyr Gly Glu Ser Pro Gln Asn Glu Gly
            20                  25                  30

Asn Lys Phe Ala Ala Ile Ser Thr His Leu Glu Val Cys Phe Met Tyr
        35                  40                  45

Ser Asp Phe His Phe Ile Asp Leu Glu Gly Asn Ala Ile Ile Lys Glu
    50                  55                  60

Ser Glu Asp Asp Asn Thr Met Leu Lys His Arg Phe Glu Ile Ile Glu
65                  70                  75                  80

Gly Gln Glu Arg Asn Val Ala Trp Thr Ile Val Asn Ser Ile Cys Asn
                85                  90                  95

Met Thr Asn Ile Asp Lys Pro Arg Tyr Leu Pro Asp Leu Tyr Asp Tyr
            100                 105                 110

Lys Thr Asn Arg Phe Ile Glu Ile Gly Val Thr Arg Arg Arg Val Glu
        115                 120                 125
```

-continued

```
Asp Tyr Tyr Tyr Glu Lys Ala Asn Lys Leu Lys Asp Gly Asn Val Tyr
    130                 135                 140

Ile His Ile Phe Ser Phe Asp Gly Glu Glu Met Ser Thr Asp Asp Glu
145                 150                 155                 160

Tyr Ile Leu Asp Glu Glu Ser Arg Ala Arg Ile Lys Thr Arg Leu Phe
                165                 170                 175

Val Leu Arg Gln Glu Met Ala Ser Ala Gly Leu Trp Asp Ser Phe Arg
            180                 185                 190

Gln Ser Glu Lys Gly Glu Glu Thr Val Glu Glu Glu Phe Lys Phe Pro
        195                 200                 205

Pro Thr Phe Lys Lys Leu Ala Asp Gln Ser Leu Pro Pro Ser Phe Lys
    210                 215                 220

Asp Tyr Asn Gln Phe Lys Val Tyr Val Ser Ser Phe Lys Ser Asn Gly
225                 230                 235                 240

Asn Ile Glu Ala Lys Leu Gly Ala Met Ser Glu Lys Val Thr Ala Thr
                245                 250                 255

Ile Glu Glu Phe Asn Pro Lys Asp Ile Thr Glu Leu Lys Met Pro Lys
            260                 265                 270

Gly Lys Pro Cys Thr Gln Arg Ser Lys Phe Leu Leu Met Asp Ser Met
        275                 280                 285

Lys Leu Ser Ile Leu Asn Pro Ser His Glu Gly Glu Gly Ile Pro Met
    290                 295                 300

Lys Asp Ala Thr Ala Cys Met Glu Thr Phe Trp Gly Trp Lys Lys Pro
305                 310                 315                 320

Asn Ile Ile Lys Lys His Asp Lys Gly Val Asn Thr Asn Tyr Leu Met
                325                 330                 335

Ile Trp Glu Gln Leu Phe Asp Ala Leu Lys Glu Asn Glu Asn Lys Tyr
            340                 345                 350

Leu Asn Leu Lys Lys Thr Asn His Leu Lys Trp Gly Leu Gly Glu Gly
        355                 360                 365

Gln Ala Pro Glu Lys Met Asp Phe Glu Asp Cys Lys Asp Ile Pro Asp
    370                 375                 380

Leu Phe Gln Tyr Lys Ser Asp Pro Pro Glu Pro Arg Gln Leu Ala Ser
385                 390                 395                 400

Trp Ile Gln Ser Glu Phe Asn Lys Ala Ser Glu Leu Thr Ser Ser Asn
                405                 410                 415

Trp Ile Glu Phe Asp Glu Leu Gly Glu Asp Val Ala Pro Ile Glu His
            420                 425                 430

Ile Ala Ser Arg Arg Arg Asn Phe Phe Thr Ala Glu Val Ser Gln Cys
        435                 440                 445

Arg Ala Ser Glu Tyr Ile Met Lys Ala Val Tyr Ile Asn Thr Ala Leu
    450                 455                 460

Leu Asn Ser Ser Cys Thr Ala Met Glu Glu Tyr Gln Val Ile Pro Ile
465                 470                 475                 480

Ile Thr Lys Cys Arg Asp Ile Ser Gly Gln Arg Lys Thr Asn Leu Tyr
                485                 490                 495

Gly Phe Ile Ile Lys Gly Arg Ser His Leu Arg Asn Asp Thr Asp Val
            500                 505                 510

Val Asn Phe Ile Ser Leu Glu Phe Ser Leu Thr Asp Pro Arg Asn Glu
        515                 520                 525

Pro His Lys Trp Glu Lys Tyr Cys Val Leu Glu Ile Gly Asp Met Glu
    530                 535                 540
```

```
Ile Lys Thr Ser Ile Ser Thr Ile Met Lys Pro Val Tyr Leu Tyr Val
545                 550                 555                 560

Arg Thr Asn Gly Thr Ser Lys Ile Lys Met Lys Trp Gly Met Glu Met
                565                 570                 575

Arg Arg Cys Leu Leu Gln Ser Leu Gln Gln Val Glu Ser Met Ile Glu
            580                 585                 590

Ala Glu Ser Ala Val Lys Glu Lys Asp Met Thr Glu Thr Phe Phe Arg
        595                 600                 605

Asn Lys Glu Asn Glu Trp Pro Ile Gly Glu Ser Pro Lys Gly Ile Glu
    610                 615                 620

Lys Gly Thr Ile Gly Lys Val Cys Arg Val Leu Leu Ala Lys Ser Val
625                 630                 635                 640

Phe Asn Ser Ile Tyr Ala Ser Ala Gln Leu Glu Gly Phe Ser Ala Glu
                645                 650                 655

Ser Arg Lys Leu Leu Leu Leu Ile Gln Ala Tyr Arg Asp Asn Leu Asp
            660                 665                 670

Pro Gly Thr Phe Asp Leu Lys Gly Leu Tyr Glu Ala Ile Glu Glu Cys
        675                 680                 685

Ile Ile Asn Asp Pro Trp Val Leu Leu Asn Ala Ser Trp Phe Asn Ser
    690                 695                 700

Phe Leu Arg Ala Val Gln Arg Ser Leu
705                 710


<210> SEQ ID NO 46
<211> LENGTH: 561
<212> TYPE: PRT
<213> ORGANISM: Influenza A virus
<220> FEATURE:
<221> NAME/KEY: MISC_FEATURE
<222> LOCATION: (1)..(561)
<223> OTHER INFORMATION: H18N11 HA Viral protein

<400> SEQUENCE: 46

Met Ile Thr Ile Leu Ile Leu Val Leu Pro Ile Val Val Gly Asp Gln
1               5                   10                  15

Ile Cys Ile Gly Tyr His Ser Asn Asn Ser Thr Gln Thr Val Asn Thr
            20                  25                  30

Leu Leu Glu Ser Asn Val Pro Val Thr Ser Ser His Ser Ile Leu Glu
        35                  40                  45

Lys Glu His Asn Gly Leu Leu Cys Lys Leu Lys Gly Lys Ala Pro Leu
    50                  55                  60

Asp Leu Ile Asp Cys Ser Leu Pro Ala Trp Leu Met Gly Asn Pro Lys
65                  70                  75                  80

Cys Asp Glu Leu Leu Thr Ala Ser Glu Trp Ala Tyr Ile Lys Glu Asp
                85                  90                  95

Pro Glu Pro Glu Asn Gly Ile Cys Phe Pro Gly Asp Phe Asp Ser Leu
            100                 105                 110

Glu Asp Leu Ile Leu Leu Val Ser Asn Thr Asp His Phe Arg Lys Glu
        115                 120                 125

Lys Ile Ile Asp Met Thr Arg Phe Ser Asp Val Thr Thr Asn Asn Val
    130                 135                 140

Asp Ser Ala Cys Pro Tyr Asp Thr Asn Gly Ala Ser Phe Tyr Arg Asn
145                 150                 155                 160

Leu Asn Trp Val Gln Gln Asn Lys Gly Lys Gln Leu Ile Phe His Tyr
                165                 170                 175

Gln Asn Ser Glu Asn Asn Pro Leu Leu Ile Ile Trp Gly Val His Gln
```

```
            180                 185                 190

Thr Ser Asn Ala Ala Glu Gln Asn Thr Tyr Tyr Gly Ser Gln Thr Gly
        195                 200                 205

Ser Thr Thr Ile Thr Ile Gly Glu Glu Thr Asn Thr Tyr Pro Leu Val
    210                 215                 220

Ile Ser Glu Ser Ser Ile Leu Asn Gly His Ser Asp Arg Ile Asn Tyr
225                 230                 235                 240

Phe Trp Gly Val Val Asn Pro Asn Gln Asn Phe Ser Ile Val Ser Thr
                245                 250                 255

Gly Asn Phe Ile Trp Pro Glu Tyr Gly Tyr Phe Phe Gln Lys Thr Thr
            260                 265                 270

Asn Ile Ser Gly Ile Ile Lys Ser Ser Glu Lys Ile Ser Asp Cys Asp
        275                 280                 285

Thr Ile Cys Gln Thr Lys Ile Gly Ala Ile Asn Ser Thr Leu Pro Phe
    290                 295                 300

Gln Asn Ile His Gln Asn Ala Ile Gly Asp Cys Pro Lys Tyr Val Lys
305                 310                 315                 320

Ala Gln Glu Leu Val Leu Ala Thr Gly Leu Arg Asn Asn Pro Ile Lys
                325                 330                 335

Glu Thr Arg Gly Leu Phe Gly Ala Ile Ala Gly Phe Ile Glu Gly Gly
            340                 345                 350

Trp Gln Gly Leu Ile Asp Gly Trp Tyr Gly Tyr His His Gln Asn Ser
        355                 360                 365

Glu Gly Ser Gly Tyr Ala Ala Asp Lys Glu Ala Thr Gln Lys Ala Val
    370                 375                 380

Asp Ala Ile Thr Thr Lys Val Asn Asn Ile Ile Asp Lys Met Asn Thr
385                 390                 395                 400

Gln Phe Glu Ser Thr Ala Lys Glu Phe Asn Lys Ile Glu Met Arg Ile
                405                 410                 415

Lys His Leu Ser Asp Arg Val Asp Asp Gly Phe Leu Asp Val Trp Ser
            420                 425                 430

Tyr Asn Ala Glu Leu Leu Val Leu Leu Glu Asn Glu Arg Thr Leu Asp
        435                 440                 445

Phe His Asp Ala Asn Val Asn Asn Leu Tyr Gln Lys Val Lys Val Gln
    450                 455                 460

Leu Lys Asp Asn Ala Ile Asp Met Gly Asn Gly Cys Phe Lys Ile Leu
465                 470                 475                 480

His Lys Cys Asn Asn Thr Cys Met Asp Asp Ile Lys Asn Gly Thr Tyr
                485                 490                 495

Asn Tyr Tyr Glu Tyr Arg Lys Glu Ser His Leu Glu Lys Gln Lys Ile
            500                 505                 510

Asp Gly Val Lys Leu Ser Glu Asn Ser Ser Tyr Lys Ile Met Ile Ile
        515                 520                 525

Tyr Ser Thr Val Ala Ser Ser Val Val Leu Gly Leu Ile Ile Leu Ala
    530                 535                 540

Ala Ile Glu Trp Gly Cys Phe Lys Gly Asn Leu Gln Cys Arg Ile Cys
545                 550                 555                 560

Ile
```

<210> SEQ ID NO 47
<211> LENGTH: 497
<212> TYPE: PRT
<213> ORGANISM: Influenza A virus
<220> FEATURE:

```
<221> NAME/KEY: MISC_FEATURE
<222> LOCATION: (1)..(497)
<223> OTHER INFORMATION: H18N11 NP Viral protein

<400> SEQUENCE: 47

Met Ala Gly Gln Gly Thr Lys Arg Thr Phe Glu Gln Met Glu Thr Asp
1               5                   10                  15

Ser Lys Gln Asn Thr Thr Glu Ile Arg Ser Ala Val Gly Arg Met Val
            20                  25                  30

Lys Ala Ile Gly Arg Phe Tyr Ile Gln Met Cys Ala Glu Leu Lys Leu
        35                  40                  45

Asp Asp Lys Glu Ala Val Leu Ile Gln Asn Ser Leu Thr Ile Glu Arg
    50                  55                  60

Met Val Leu Ser Ala Phe Asp Glu Arg Arg Asn Lys Tyr Leu Glu Glu
65                  70                  75                  80

His Pro Thr Val Gly Lys Asp Pro Lys Lys Thr Gly Gly Pro Ile Tyr
                85                  90                  95

Arg Arg Lys Glu Gly Lys Trp Glu Arg Glu Met Val Leu Met Glu Lys
            100                 105                 110

Glu Asn Ile Arg Ala Ile Trp Lys Met Ala Asn Asp Gly Glu Glu Asn
        115                 120                 125

Leu Ser Gly Leu Ser His Ile Met Ile Trp His Ser Asn Leu Asn Asp
    130                 135                 140

Thr Thr Tyr Gln Arg Thr Arg Ala Leu Val Arg Thr Gly Met Asp Pro
145                 150                 155                 160

Arg Met Cys Ser Leu Met Gln Gly Ser Thr Leu Pro Arg Arg Ala Gly
                165                 170                 175

Ala Ala Gly Ala Ala Ile Lys Gly Val Gly Thr Leu Ile Met Glu Leu
            180                 185                 190

Ile Arg Met Ile Lys Arg Gly Met Asn Asp Arg Asn Phe Trp Lys Gly
        195                 200                 205

Glu Gln Gly Lys Arg Thr Arg Ala Ala Tyr Glu Arg Ile Cys Asn Asn
    210                 215                 220

Leu Lys Asn Lys Phe Gln Thr Ala Pro Gln Lys Ala Met Val Asp Gln
225                 230                 235                 240

Val Lys Glu Gly Lys Asn Pro Gly Asn Ala Glu Ile Glu Asp Leu Leu
                245                 250                 255

Phe Leu Ala Arg Ser Ala Leu Ile Leu Arg Gly Ala Val Ala His Lys
            260                 265                 270

Ser Ser Leu Pro Ala Cys Val Tyr Gly Leu Gly Val Ser Arg Gly Phe
        275                 280                 285

Asp Phe Glu Arg Glu Gly Tyr Ser Leu Val Gly Arg Asp Pro Tyr Met
    290                 295                 300

Leu Leu Gln Asn Ser Gln Ile Phe Ser Ile Ile Arg Lys Gly Glu Asn
305                 310                 315                 320

Ala Ala His Lys Ser Gln Leu Val Trp Met Ala Cys His Ala Ala Ala
                325                 330                 335

Phe Glu Asp Ile Arg Val Ser Ser Phe Ile Lys Gly Asn Lys Ile Val
            340                 345                 350

Pro Arg Gly Lys Leu Glu Thr Arg Gly Leu Gln Ile Ala Gly Ser Glu
        355                 360                 365

Thr Leu Asp Glu Ala Leu Val Val Ser Leu Asp Ile Lys Ser His Tyr
    370                 375                 380

Trp Ala Ile Lys Thr Arg Ser Gly Gly Asn Pro Gln Gln Ser Arg Ser
```

385 390 395 400

Ser Ala Gly Gln Ile Ala Val Gln Pro Thr Phe Ser Val Gln Arg Asn
405 410 415

Ile Pro Phe Glu Lys Lys Thr Ile Met Ala Ala Phe Ser Asn Ile Glu
420 425 430

Glu Gly Arg Ile Thr Asp Met Arg Thr Glu Ile Ile Lys Leu Met Glu
435 440 445

Asn Ser Asp Pro Lys Asp Lys Val Phe Leu Gly Arg Gly Val Phe Glu
450 455 460

Met Ala Asp Glu Lys Ala Thr Asn Pro Ile Val Pro Ser Leu Asp Gly
465 470 475 480

Asn Asp Glu Gly Ser Tyr Phe Phe Gly Asp Lys Ala Glu Glu Phe Asp
485 490 495

Ile

<210> SEQ ID NO 48
<211> LENGTH: 447
<212> TYPE: PRT
<213> ORGANISM: Influenza A virus
<220> FEATURE:
<221> NAME/KEY: MISC_FEATURE
<222> LOCATION: (1)..(447)
<223> OTHER INFORMATION: H18N11 NA Viral protein

<400> SEQUENCE: 48

Met Ser Phe Gln Thr Ser Thr Cys Leu Leu Ile Val Ser Leu Ile Cys
1 5 10 15

Gly Ile Leu Thr Val Cys Leu Gln Val Leu Leu Pro Phe Ile Leu Ile
20 25 30

Trp Thr Asn Thr Glu Pro Asn Tyr Ser Cys Glu Cys Pro Ala Pro Asn
35 40 45

Ile Ser Leu Ser Cys Pro Asn Gly Thr Ser Val Thr Tyr Asp Ser Lys
50 55 60

Asn Ile Thr Glu Asn Ser Phe Tyr Ser Ser Thr Thr Asn Tyr Leu Ser
65 70 75 80

Pro Val Ile Ala Thr Pro Leu Val Leu Gly Glu Asn Leu Cys Ser Ile
85 90 95

Asn Gly Trp Val Pro Thr Tyr Arg Gly Glu Gly Thr Thr Gly Lys Ile
100 105 110

Pro Asp Glu Gln Met Leu Thr Arg Gln Asn Phe Val Ser Cys Ser Asp
115 120 125

Lys Glu Cys Arg Arg Phe Phe Val Ser Met Gly Tyr Gly Thr Thr Thr
130 135 140

Asn Phe Ala Asp Leu Ile Val Ser Glu Gln Met Asn Val Tyr Ser Val
145 150 155 160

Lys Leu Gly Asp Pro Pro Thr Pro Asp Lys Leu Lys Phe Glu Ala Val
165 170 175

Gly Trp Ser Ala Ser Ser Cys His Asp Gly Phe Gln Trp Thr Val Leu
180 185 190

Ser Val Ala Gly Asp Gly Phe Val Ser Ile Leu Tyr Gly Gly Ile Ile
195 200 205

Thr Asp Thr Ile His Pro Thr Asn Gly Gly Pro Leu Arg Thr Gln Ala
210 215 220

Ser Ser Cys Ile Cys Asn Asp Gly Thr Cys Tyr Thr Ile Ile Ala Asp
225 230 235 240

```
Gly Thr Thr Tyr Thr Ala Ser Ser His Arg Leu Tyr Arg Leu Val Asn
                245                 250                 255

Gly Thr Ser Ala Gly Trp Lys Ala Leu Asp Thr Thr Gly Phe Asn Phe
            260                 265                 270

Glu Phe Pro Thr Cys Tyr Tyr Thr Ser Gly Lys Val Lys Cys Thr Gly
        275                 280                 285

Thr Asn Leu Trp Asn Asp Ala Lys Arg Pro Phe Leu Glu Phe Asp Gln
    290                 295                 300

Ser Phe Thr Tyr Thr Phe Lys Glu Pro Cys Leu Gly Phe Leu Gly Asp
305                 310                 315                 320

Thr Pro Arg Gly Ile Asp Thr Thr Asn Tyr Cys Asp Lys Thr Thr Thr
                325                 330                 335

Glu Gly Glu Gly Gly Ile Gln Gly Phe Met Ile Glu Gly Ser Asn Ser
            340                 345                 350

Trp Ile Gly Arg Ile Ile Asn Pro Gly Ser Lys Lys Gly Phe Glu Ile
        355                 360                 365

Tyr Lys Phe Leu Gly Thr Leu Phe Ser Val Gln Thr Val Gly Asn Arg
    370                 375                 380

Asn Tyr Gln Leu Leu Ser Asn Ser Thr Ile Gly Arg Ser Gly Leu Tyr
385                 390                 395                 400

Gln Pro Ala Tyr Glu Ser Arg Asp Cys Gln Glu Leu Cys Phe Trp Ile
                405                 410                 415

Glu Ile Ala Ala Thr Thr Lys Ala Gly Leu Ser Ser Asn Asp Leu Ile
            420                 425                 430

Thr Phe Cys Gly Thr Gly Gly Ser Met Pro Asp Val Asn Trp Gly
        435                 440                 445


<210> SEQ ID NO 49
<211> LENGTH: 252
<212> TYPE: PRT
<213> ORGANISM: Influenza A virus
<220> FEATURE:
<221> NAME/KEY: MISC_FEATURE
<222> LOCATION: (1)..(252)
<223> OTHER INFORMATION: H18N11 M1 Viral protein

<400> SEQUENCE: 49

Met Ser Ile Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ser Gly Arg Asn Ser Asp Leu Asp Thr Leu Leu Glu Trp Leu Lys Thr
        35                  40                  45

Arg Pro Ile Leu Ser Pro Leu Thr Lys Gly Ile Val Gly Phe Val Phe
    50                  55                  60

Thr Leu Thr Val Pro Cys Glu Lys Asn Thr Ser Arg Arg Lys Phe Ile
65                  70                  75                  80

Gln Thr Ala Leu Asn Gly Asn Gly Glu Thr Ala Asn Met Asp Lys Ala
                85                  90                  95

Val Lys Ile Tyr Lys Lys Leu Lys Lys Glu Ile Thr Phe His Gly Ala
            100                 105                 110

Lys Glu Val Ala Leu Ser Tyr Pro Thr Gly Ala Leu Ala Cys Cys Met
        115                 120                 125

Gly Leu Ile Tyr Asn Arg Met Gly Ser Val Thr Thr Glu Val Ala Phe
    130                 135                 140

Gly Leu Val Cys Ala Thr Cys Glu His Ile Ala Asp Ser Gln Tyr Arg
```

```
145                 150                 155                 160

Ser His Lys Gln Met Val Gly Ser Thr Asn Pro Leu Ile Arg His Glu
                165                 170                 175

Asn Arg Met Ala Thr Ala Ala Ser Thr Ala Lys Ala Met Glu Gln Met
            180                 185                 190

Ala Ser Ser Ser Asp Gln Ala Ala Glu Ala Met Glu Ile Ala Ser Gln
        195                 200                 205

Ala Arg Gln Met Ile Gln Ala Met Arg Ala Ile Gly Thr His Pro Thr
    210                 215                 220

Thr Ser Ser Gly Leu Lys Asp Asp Leu Leu Asp Asn Leu Gln Ala Tyr
225                 230                 235                 240

Gln Lys Arg Met Gly Ile Gln Met Gln Arg Phe Lys
                245                 250


<210> SEQ ID NO 50
<211> LENGTH: 96
<212> TYPE: PRT
<213> ORGANISM: Influenza A virus
<220> FEATURE:
<221> NAME/KEY: MISC_FEATURE
<222> LOCATION: (1)..(96)
<223> OTHER INFORMATION: H18N11 M2 Viral protein

<400> SEQUENCE: 50

Met Ser Ile Leu Thr Glu Val Glu Thr Leu Thr Arg Lys Gly Trp Glu
1               5                   10                  15

Ser Arg Cys Ser Gly Leu Asn Glu Asp Leu Ile Leu Ala Ala Asn Ile
            20                  25                  30

Ile Gly Ile Ile His Leu Ala Leu Trp Ile Ile Asp Arg Trp Leu Tyr
        35                  40                  45

Arg Tyr Ser Leu Leu Ile Tyr Arg Lys Ile Trp Asn Thr Trp Gly Leu
    50                  55                  60

Lys Pro Val Asp Ser Thr Lys Glu Leu Arg Glu Glu Phe Lys Glu Glu
65                  70                  75                  80

His Lys Ser Ile Glu Phe Pro Asp Pro Ile Met Thr Ile Ile Glu Asn
                85                  90                  95


<210> SEQ ID NO 51
<211> LENGTH: 221
<212> TYPE: PRT
<213> ORGANISM: Influenza A virus
<220> FEATURE:
<221> NAME/KEY: MISC_FEATURE
<222> LOCATION: (1)..(221)
<223> OTHER INFORMATION: H18N11 NS1 Viral protein

<400> SEQUENCE: 51

Met Glu Ser Thr Pro Thr Thr Ile Ala Phe Gln Val Asp Cys Tyr Leu
1               5                   10                  15

Trp His Leu Lys Lys Met Leu Ser Leu Met Gly Glu Val Asp Ala Pro
            20                  25                  30

Phe Glu Asp Arg Leu Arg Arg Glu Gln Lys Ala Leu Lys Gly Arg Ser
        35                  40                  45

Met Thr Leu Gly Ile Asp Ile Gln Ala Ala Thr Lys Ala Gly Tyr Tyr
    50                  55                  60

Lys Ile Lys Ser Ile Thr Glu Asp Ala Met Pro Tyr Tyr Gly Ile Leu
65                  70                  75                  80

Pro Asn Ala Gly Gln Ser Glu Pro Lys Tyr Ile Thr Glu Met Thr Val
                85                  90                  95
```

-continued

```
Glu Glu Thr Asn Arg Asn Trp Ile Met Ile Gln Pro Lys Gln Lys Val
            100                 105                 110

Ile Gly Gly Arg Ile Leu Ile Ser Met Asp Gln Ala Ile Thr Asp Lys
        115                 120                 125

Val Ile Thr Ile Lys Ala Asn Phe Thr Val Cys Phe Gly Lys Val Glu
    130                 135                 140

Arg Leu Val Leu Ala Arg Ala Phe Thr Pro Glu Gly Ala Val Val Gly
145                 150                 155                 160

Glu Ile Asn Pro Leu Ser Phe Val Thr Gly His Thr Gly Glu Asp Val
                165                 170                 175

Lys Thr Ala Tyr Glu Leu Phe Arg Ser Gly Phe Glu Trp Asn Asp Asn
            180                 185                 190

Ala Ile Glu Glu Ser Gln Ile Leu Gln Gly Phe Leu Gly Arg Ile Ala
        195                 200                 205

Asp Ala Glu Arg Arg Leu Gln Glu Asn Glu Pro Ala Glu
    210                 215                 220


<210> SEQ ID NO 52
<211> LENGTH: 122
<212> TYPE: PRT
<213> ORGANISM: Influenza A virus
<220> FEATURE:
<221> NAME/KEY: MISC_FEATURE
<222> LOCATION: (1)..(122)
<223> OTHER INFORMATION: H18N11 NS2 Viral protein

<400> SEQUENCE: 52

Met Glu Ser Thr Pro Thr Thr Ile Ala Phe Gln Asp Ile Leu Glu Arg
1               5                   10                  15

Met Ser Lys Leu His Met Asn Ser Ser Glu Ala Asp Leu Asn Gly Met
            20                  25                  30

Ile Thr Gln Leu Lys Asn Leu Lys Phe Phe Arg Asp Ser Leu Glu Glu
        35                  40                  45

Ser Leu Met Arg Asn Gly Asp Tyr Arg Lys Met Ser Gln Gln Asn Glu
    50                  55                  60

Asn Trp Arg Ser Gln Leu Gly Asp Lys Leu Asn Val Ile Arg Asn Leu
65                  70                  75                  80

Ile Gln Thr Cys Arg Glu Ile Leu Leu Thr Ser Thr Asn Ser Phe Ile
                85                  90                  95

Glu Ile Thr Phe Leu Ala Ala Leu Asn Leu Leu Leu Glu Val Glu Arg
            100                 105                 110

Glu Met Arg Thr Leu Ala Phe Gln Leu Ile
        115                 120
```

MODIFIED BAT INFLUENZA VIRUSES AND THEIR USES

CROSS-REFERENCE TO RELATED APPLICATIONS

The present application is the U.S. National Stage of International Patent Application No. PCT/US2015/048648, filed Sep. 4, 2015, which claims the priority benefit of U.S. Provisional Application Ser. No. 62/046,528, filed Sep. 5, 2014, entitled Modified Bat Influenza Viruses and their uses, each of which is incorporated by reference in its entirety herein.

SEQUENCE LISTING

The following application contains a sequence listing in computer readable format (CRF), submitted as a text file in ASCII format entitled "SequenceListing," created on Sep. 4, 2015, as 136 KB. The content of the CRF is hereby incorporated by reference herein in its entirety.

BACKGROUND OF THE INVENTION

Field of the Invention

The present invention relates to live attenuated influenza vaccines.

Description of Related Art

Bats are present throughout most of the world and account for more than a fifth of mammalian species. They are natural reservoirs of some of the most deadly zoonotic viruses, including rabies virus, Ebola virus, Henipaviruses, and SARS coronavirus. Recently, nucleic acids obtained from bat samples indicated bats may be a reservoir of a new group of influenza viruses (bat-influenza) that are phylogenetically very distantly related to other influenza viruses. Type A, B, and C influenza viruses belong to the Orthomyxoviridae family and their genomes are composed of 7-8 negative sense RNA segments (vRNAs). While influenza B (IBV) and C viruses mainly infect human hosts, influenza A virus (IAV) has a broad host range; including humans, marine mammals, horses, pigs, waterfowl, and poultry. New subtypes of IAV, which have novel hemagglutinin (HA) and/or neuraminidase (NA) surface glycoproteins, are introduced into the human population by zoonosis and this periodically leads to devastating pandemics. Past pandemics include the "Spanish flu" (H1N1) in 1918, "Asian flu" (H2N2) in 1957, "Hong Kong flu" (H3N2) in 1968, "Russian flu" (H1N1) in 1977, and the recent "swine origin" flu (pH1N1) in 2009. Pandemic viruses are often reassortant viruses composed of vRNAs that are derived from multiple IAV lineages that previously circulated in swine and/or avian reservoirs (e.g., 1957 avian-human reassortant, 1968 avian-human reassortant, and 2009 avian-swine-human reassortant). The discovery of putative bat-influenza viruses expands the known host species reservoirs that may serve as a source of novel viruses, which is a major concern for public and animal health.

Infectious bat-influenza viruses couldn't be isolated and although several structural and biochemical characterization studies have been conducted with the putative bat-influenza HA, NA, and part of PA, none of the vRNAs have been shown to be functional in a replicative virus. This has led to questions such as: (1) are the putative bat-influenza vRNA sequences identified derived from infectious viruses or are they merely nucleic acid relics harbored in bats, (2) are the vRNA segments sequenced from a single bat-influenza virus or are they from multiple potentially incompatible viruses, and (3) were the sequences of the complete gene segments, which is a significant technical challenge, determined accurately. The inability to culture infectious viruses is the major hurdle to confirm the existence of these novel influenza viruses, and to answer important questions, such as pathogenicity in animal models, ability to reassort with other influenza viruses, and their potential risk to public health.

Modified live attenuated influenza vaccines for swine industry have been developed and shown that they are more efficacious than the traditional inactivated vaccines, but they are not applied on the market. The big concern is the safety issue, i.e., that the live attenuated vaccine might reassort with the endemic influenza A viruses to generate more virulent virus in a host.

SUMMARY OF THE INVENTION

The present invention is broadly concerned with vaccine compositions useful for vaccination against a target influenza strain. The compositions comprise a live synthetic influenza virus dispersed in a pharmaceutically-acceptable carrier. The influenza virus comprises a backbone of viral segments derived from a bat influenza strain, and heterologous surface proteins HA and NA derived from the target influenza strain. Advantageously, each of the heterologous surface proteins HA and NA are encoded by a chimeric viral segment comprising a protein open reading frame for the HA or NA of the target influenza strain, and noncoding regions and viral packaging sequences derived from the bat influenza strain.

Methods of vaccinating against a target influenza strain to prevent or mitigate influenza infection in a subject are also described herein. The methods comprise administering a vaccine composition according to embodiments of the invention to the subject.

A kit for vaccination against a target influenza strain to prevent or mitigate influenza infection in a subject is also described herein. The kit comprises a vaccine composition according to embodiments of the invention, instructions for administering the vaccine composition to the subject.

Also described herein is the use of a composition according to embodiments of the invention for vaccination against a target influenza strain to prevent or mitigate influenza infection in a subject.

Kits for study and/or generation of chimeric influenza virus strains are also described herein. The kits comprise vectors encoding for backbone viral segments derived from a bat influenza strain to produce a platform virus, along with vectors encoding for non-bat surface proteins HA and NA or vectors for inserting non-bat HA and NA sequences for generation of the chimeric virus strains. Instruction for transfecting cells with said vectors to generate said chimeric virus strains are also included in the kit.

The invention is also concerned with synthetic cDNA encoding for hemagglutinin surface protein useful for generating live influenza viruses comprising SEQ ID NO:1 or 3. Synthetic cDNA encoding for neuraminidase surface protein useful for generating live influenza viruses comprising SEQ ID NO:2 or 4 is also disclosed.

BRIEF DESCRIPTION OF THE DRAWINGS

FIG. 2A: EM picture of Bat09 (left), Bat09: mH1mN1 (middle), and PR8 (right). FIG. 2B: Viral titers in transfection supernatants of Bat09 and PR8-HA/NA reassortants, and Bat09:mH1mN1. Each bar represents an independent rescue experiment. FIG. 2C: mH1 contains PR8-HA coding region and Bat09-HA packaging region (start codon removed). The mN1 was constructed using the same strategy. FIG. 2D: Bat09:mH1mN1 and PR8 replication kinetics in MDCK cells. FIG. 2E: Peak titers of the viruses in embryonated chicken eggs. *, $P<0.05$, compared to PR8.

FIG. 3A: Modified. HA (mH1) and modified NA (mN1). FIG. 3B: modified HA and NA regions with silent substitutions into the coding region of mH1 to disrupt the remaining packaging signals in the PR8-HA and NA coding regions. FIG. 3C: wild type NS gene and the NS1 truncated NS gene from Bat09. FIG. 3D: Bat09 NP and NS coding regions flanked by putative cis-acting packaging regions from PR8 NP and NS. PR8 NP and NS coding regions flanked by putative cis-acting packaging regions from Bat NP and NS. FIG. 3E: pPol1-Bat-NS-Luc, pPol1-FluA-NS-Luc, and pPol1-HUB-NS-Luc reporter genes.

FIG. 4A: Virus titers of Bat09:mH1mN1 and PR8 in mouse lungs at 3 and 5 dpi. Each mouse was intranasally inoculated with 1.0*3 $TCID_{50}$ of each virus. FIG. 4B: Mouse weight on each day post inoculation was represented as a percentage of the weight on day 0 (100%). Each mouse was intranasally inoculated with 10*4 $TCID_{50}$ of Bat09:mH1mN1 or PR8. FIG. 4C: Survival rate of the mice inoculated with 10*4 $TCID_{50}$ of virus. FIG. 4D: H&E staining of microscopic lung sections from mice inoculated with 10*3 $TCID_{50}$ of virus at 5 dpi. FIG. 4E: IHC staining of lung sections at 5 dpi. *, $P<0.05$, Bat09: mH1mN1 compared to PR8.

FIG. 5A: Modified HA (mH3) and modified NA (mN2) constructs. FIG. 5B: Bat09:mH3mN2 and TX98 replication kinetics in MDCK cells. MDCK cells were inoculated at a multiplicity of infection (MOI) of 0.01 $TCID_{50}$/cell with the Bat09:mH3mN2 or TX98 viruses. FIG. 5C: Weight loss of mice mock-infected or infected with Bat09:mH3mN2 or TX98 viruses. Each mouse was intranasally inoculated with 3×10*5 $TCID_{50}$ of each virus. FIG. 5D: Virus titers of Bat09:mH3mN2 and TX98 viruses in mouse lungs at 3 and 5 dpi. Each mouse was intranasally inoculated with 3×10*4 $TCID_{50}$ of each virus. *, $P<0.05$, Bat09:mH3mN2 compared to TX98.

FIG. 6A: Luciferase reporter mediated assay to quantitate the NS1 protein inhibition effects on interferon-promoter activation. FIG. 6B: VSV-luciferase mediated bioassay to quantitate the inhibitory effects on VSV virus infection resulted from the immune response induced by the different NS1 WT or truncated viruses. FIG. 6C: Virus replication kinetics in human lung epithelial Calu-3 cells. * or #, $P<0.05$, Bat-NS1-128 compared to PR8-NS1-126 (*) and Bat-NS1-73 compared to PR8-NS1-73 (#) are shown in 6B and 6C.

FIG. 7A: Virus titers of Bat09: mH1mN1ss and NS1 mutants in mouse lungs at 3 and 5 dpi. Each mouse was intranasally inoculated with 10*4 $TCID_{50}$ of each virus. FIG. 7B: Mouse weight on each day post inoculation was represented as a percentage of the weight on day 0 (100%). Each mouse was intranasally inoculated with 10*5 $TCID_{50}$ of the indicated viruses. FIG. 7C: Survival rate of the mice inoculated with 10*5 $TCID_{50}$ of the viruses. Higher virus doses were used in this experiment based on the PR8-NS1-126 control virus, which caused significant weight loss but had low mortality at 10*5 $TCID_{50}$ so the attenuation of Bat-NS1 truncated viruses can be appropriately compared to it. *, $P<0.05$, truncated Bat09:mH1mN1ss-128 and Bat09: mH1mN1ss-73 compared to PR8-NS1-126.

FIG. 8A: Virus titers of Bat09: mH1mN1 and PB2 mutants in mouse lungs at 3 and 5 dpi. Each mouse was intranasally inoculated with 10*3 $TCID_{50}$ of each virus. FIG. 8B: Mouse weight on each day post inoculation was represented as a percentage of the weight on day 0 (100%). Each mouse was intranasally inoculated with 10*4 $TCID_{50}$ of the indicated viruses. FIG. 8C: Survival rate of the mice inoculated with 10*4 $TCID_{50}$ of the viruses. *, $P<0.05$, PB2 mutants compared to Bat09:mH1mN1. For mouse body weight, * is only marked on the first day of each group that is significantly different from Bat09:mH1mN1.

FIGS. 11A-11I: PB2, PB1, PA, and NP from Bat09 and various influenza A viruses as indicated. FIG. 11J: PB2, PB1, PA and NP from Bat09 and B/Russia/69. FIG. 11K: PB2, PB1, PA and NP from Bat09 and Bat10.

FIGS. 12A-12B show the sequence alignment of: FIG. 12A PR8-HA, mH1, mH1ss, and FIG. 12B PR8-NA, mN1, mN1ss.

Figure 1:
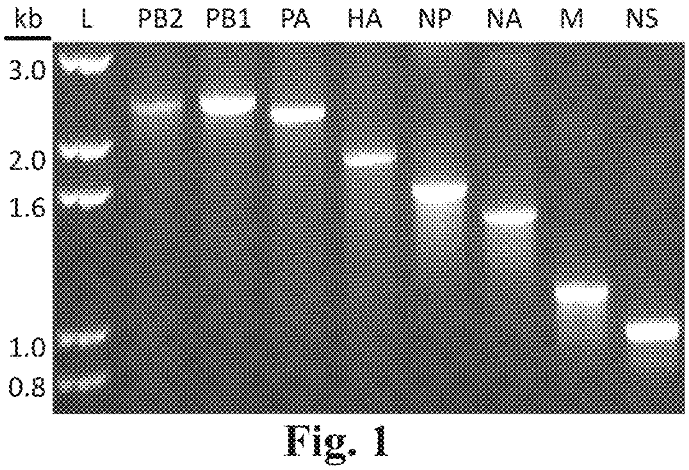
FIG. 1 is a DNA image of synthetic generation of the eight full-length genomic segments of A/little yellow-shouldered bat/Guatemala/164/2009 (Bat09). The products were assembled from oligonucleotides and error corrected, L: 1 Kb Plus DNA ladder from Life Technologies.

Virus titers in BALF samples of infected pigs at 3, 5 and 7 dpi and contact pigs at 5 dpc; B) Virus titers in nasal swabs of infected pigs at 3, 5 and 7 dpi and contact pigs at 2, 4 and 5 dpc. All animals were positive for virus isolation at indicated time points unless otherwise indicated (e.g., ⅛=1 of 8 animals positive). Dotted lines represent the limit of detection. Error bars represent±SEM (* $P<0.05$;  $P<0.01$; * $P<0.001$).

DETAILED DESCRIPTION

Provided herein is a synthetically generated replicative virus that can be used as a model to better understand bat-influenza viruses and to create safe and efficacious live attenuated vaccines. The viruses described herein are referred to as being "modified" or "chimeric," which means that they differ from wild-type virus strains and have non-wild type genomes and virions in which at least a portion thereof originates from a different species. More specifically, the chimeric (non-wild type) influenza viruses incorporate backbone genome segments of bat influenza and heterologous surface proteins hemagglutinin (HA) and neuraminidase (NA) from the target influenza strain(s). These chimeric viruses are "synthetic" in that the individual viral segments are synthetically constructed from oligonucleotides to form functional viral segments, as discussed in more detail below, and then the segments are expressed to generate live, replicating virus particles with heterologous surface proteins HA and NA. These live, synthetic viruses are useful in vaccine formulations for eliciting immune responses against the target influenza strain(s). In general, the "target" influenza virus refers to the strain or strains against which the vaccine is designed to have prophylactic (or therapeutic) effect and provide immunoprotection to the vaccinated subject. In some embodiments, the target influenza virus may be an endemic circulating influenza virus identified in the population or species to be vaccinated. In some embodiments, the target influenza virus may be a strain or strains predicted to become pathogenic in the population or species to be vaccinated.

The influenza A virus genome consists of eight segments of negative-sense single-stranded RNA, encoding six internal proteins (PB2, PB1, PA, NP, M, and NS), and the two surface glycoproteins (HA and NA). The viral particle comprises a lipid bilayer envelope, within which all eight RNA genomic segments reside, and the outer layer of the lipid envelope is spiked with multiple glycoproteins HA and NA (and a small number of M2). Each of the eight independent genome segments can recombine among influenza viruses to produce new subtypes during a process called reassortment. During replication, the genomic viral RNA is transcribed into positive-strand mRNA and negative-strand genomic cRNA in the nucleus of the host cell. Each of the eight genomic segments is packaged into ribonucleoprotein complexes that contain, in addition to the RNA, NP and a polymerase complex (PB1, PB2, and PA). The influenza virus is characterized by a viral particle (virion) having surface HA and NA extending from the particle envelope, and viral RNAs that make up the eight-segment genome inside the particle core and bound to ribonuclear proteins (RNPs). HA is responsible for viral cell entry by membrane fusion, whereas NA plays important roles in viral release and cell-to-cell spread of infection. Thus, vaccines according to the invention are designed to induce neutralizing antibody responses against the influenza virions and more specifically against the HA and NA glycoproteins.

One embodiment of the invention comprises technology to generate modified bat viruses. In one embodiment of the invention the modified/chimeric bat virus produced by this technology can be used to create whole-virus vaccines. In one embodiment of the invention the vaccine is attenuated in pigs or other animals when compared to the wild type virus and is immunogenic to produce hemagglutination inhibition antibodies. The advantages of these modified bat viruses used for attenuated live influenza vaccines is that they do not reassort with canonical influenza. A viruses, resulting in a safe vaccine without reassortment potential.

The viral segments are derived from known virus strains. As used herein the term "derived from" means that the modified or chimeric bat virus is synthetically generated from genome segments constructed directly using the known sequences for the corresponding segment of each strain and chemical or enzymatic synthesis and assembly of the oligonucleotides. For example, internal segment for PB2 of the synthetic virus is "derived from" PB2 of bat influenza, in that the genome segment encoding for PB2 of the synthetic virus is constructed synthetically using the known coding sequence for PB2 of bat influenza as the template. Various synthetic genetics techniques are known in the art, including those described in WO 2014/115104, incorporated by reference herein to the extent not inconsistent with this disclosure. Such techniques are also described in Dormitzer P R, et al. and Liu Q, et al. infra. Briefly, the synthetic constructs comprise coding sequences for expressing one or more viral RNA segment(s) of an influenza virus genome. The encoded segments can be expressed and then function as viral RNAs which can be packaged into virions. For example, the synthetic expression construct can drive expression in a eukaryotic cell of viral segments encoded therein. The expressed viral segment RNA can be translated into a viral protein that can be incorporated into a virion. Exemplary techniques for producing constructs include (i) synthesizing a plurality of overlapping fragments of the synthetic expression construct, wherein the overlapping fragments span the complete synthetic expression construct, and (ii) joining the fragments to provide the synthetic expression construct. The synthetic expression construct can encode all (eight) viral segments necessary to produce an influenza virus, or the viral segments can be provided in multiple expression construct(s).

In one or more embodiments, each of the eight viral segments is synthesized into individual expression constructs, each containing one copy of the viral cDNA. For example, Hoffmann, et al. disclose an eight-plasmid DNA transfection system for the rescue of infectious influenza A virus from cloned cDNA (Proc. Natl. Acad. Sci., vol. 97, no. 11, A DNA transfection system for generation of influenza A virus from eight plasmids (2000)). In this plasmid-based expression system, synthesized cDNA for the virus is inserted between the RNA polymerase I (pol I) promoter and terminator sequences. The plasmids are transfected into a eukaryotic cell system. This entire pol I transcription unit is flanked by an RNA polymerase II (pol II) promoter and a polyadenylation site. The orientation of the two transcription units allows the synthesis of negative-sense viral RNA and positive-sense mRNA from one viral cDNA template. The mRNAs are translated into viral proteins. Interaction of these molecules derived from the cellular transcription and translation machinery results in the interaction of all synthesized molecules (vRNPs and structural proteins) to generate functional (infectious) viral particles.

Advantageously, the bat influenza virus backbone can be used as a platform strain(s) for the generation of live attenuated vaccines for influenza. Thus, the backbone viral genome segments are synthesized according to backbone sequences of one or more bat influenza virus strains. As used herein, reference to "backbone" or "platform" sequences refers to sets of genome segments encoding influenza virus proteins other than surface proteins HA and NA (and thus, generally refers to the internal core genome segments). Thus, the "platform" strain or virus refers to the virus from which backbone segments (or sequence information relating thereto) originate. More specifically, the six internal protein coding vRNAs for PB2, PB1, PA, NP, M, and NS from bat-influenza can be synthesized (via cDNA) from known or determined sequences to produce viral backbone genome segments. Sequence fragments may also be used so long as they are "functional fragments" meaning that they nonetheless encode a functional protein for the virus from which the sequence was derived.

Exemplary bat influenza strains are A/little yellow-shouldered bat/Guatemala/164/2009 (H17N10) and A/flat-faced bat/Peru/033/2010 (H18N11). Sequence information for A/little yellow-shouldered bat/Guatemala/164/2009 (H17N10) backbone segments are available under Genbank accession Nos. CY103881.1, CY103882.1, CY103883.1, CY103885.1, CY103887.1, and CY103888.1, incorporated by reference herein. In one or more embodiments, the backbone segments are synthesized from synthetic constructs of H17N10 comprising SEQ ID NO:5 (PB2), SEQ ID NO:6 (PB1), SEQ ID NO:7 (PA), SEQ ID NO:8 (NP), SEQ ID NO:10 (M1, M2), SEQ ID NO: 13 (NS1, NEP), SEQ ID NO:15 (NS1-128, NEP), or SEQ ID NO:16 (NS1-73, NEP). In one or more embodiments, the backbone segments encode for one or more viral proteins selected from the group consisting of SEQ ID NO:9 (NP), SEQ ID NO:11 (M2), SEQ ID NO:1.2 (M1), SEQ ID NO:14 (NS1), SEQ ID NO:39 (PB2), SEQ ID NO:40 (PB1), SEQ ID NO:41 (PA), and SEQ ID NO:42 (NS2). Sequence information for A/flat-faced bat/Peru/033/2010 (H18N11) backbone segments are available under Genbank accession no. CY125942.1, CY125943.1, CY125944.1, CY125946.1, CY125948.1, and CY125949.1, incorporated by reference herein. In one or more embodiments, the backbone segments are synthesized from synthetic constructs of H18N11 comprising SEQ ID NO:17 (PB2), SEQ ID NO:18 (PB1), SEQ ID NO:19 (PA), SEQ ID NO:21 (NP), SEQ ID NO:23 (M1, M2), or SEQ ID NO:24 (NS1, NEP). In one or more embodiments, the backbone segments encode for one or more viral proteins selected from the group consisting of SEQ ID NO:43 (PB2), SEQ ID NO:44 (PB1), SEQ ID NO:45 (PA), SEQ ID NO:47 (NP), SEQ ID NO:49 (M1), SEQ ID NO:50 (M2), SEQ ID NO:51 (NS1), and SEQ ID NO:52 (NS2).

Heterologous gene(s) or genome segment(s) encoding a complete open reading frame for non-bat surface proteins HA and NA are likewise synthesized based upon sequence information for the target influenza virus to be vaccinated against. The term "non-bat" is used herein to denote that the surface proteins are not native to bat influenza, but instead originate from a virus strain in a species other than bat (e.g., human, avian, swine, equine etc.). The sequence of the coding region for the non-bat HA or NA can be obtained by sequencing the circulating strain, or from recombinant or reassortants of the target strain. It is preferred that the complete coding region is used, although fragments may be used so long as they encode a functional (immunogenic/antigenic) HA or NA surface glycoprotein of the virus from which the coding region is derived (i.e., are "functional fragments"). The heterologous influenza HA or NA cDNA is synthetized and flanked by control sequences, and more particularly, is a chimeric gene in which the noncoding regions and viral packaging sequences from the platform bat influenza virus is retained. That is, in the synthesized HA or NA gene sequence, the protein open reading frame of the platform bat influenza HA or NA sequence is replaced by the protein open reading frame sequence for the HA or NA of the target circulating influenza virus. If necessary, silent substitutions or other mutations can be introduced to disrupt the native packaging signals in the non-bat influenza HA and NA terminal coding regions. Thus, the HA and NA viral genome segments are each chimeric genes comprising (consisting essentially, or even consisting of) bat-influenza viral packaging sequence(s), bat-influenza non-coding regions, and a non-bat influenza open reading frame encoding for non-bat HA or non-bat NA. Thus, the protein coding region is flanked by cis-acting terminal packaging signals from bat-influenza selected for similarity to regions known to be central to packaging of the non-bat influenza. For example, the working examples demonstrate modified bat-influenza viruses A/little yellow-shouldered bat/Guatemala/164/2009 (H17N10) and A/flat-faced bat/Peru/033/2010 (H18N11) that had the HA and NA coding regions replaced with HA and NA coding regions from either H1N1 A/PR/8/1934 (PR8) or H3N2 A/swine/Texas/4199-2/1998 (TX98) virus. Sequence information for surface protein HA of H17N10 is available under Genbank accession no. CY103884.1, and the NA sequence is available under Genbank accession no. CY103886.1, incorporated by reference herein. Sequence information for surface protein HA of H18N11 is available under Genbank accession no. CY125945.1, and the NA sequence is available under Genbank accession no. CY125947.1, incorporated by reference herein. The synthesized cDNA sequence for H18N11 HA is shown in SEQ ID NO:20, with the viral protein sequence shown in SEQ ID NO:46. The synthesized cDNA sequence for H19N11 NA is shown in SEQ ID NO:22, with the viral protein sequence shown in SEQ ID NO:48. In one or more embodiments, the HA segment is a synthetic construct comprising (consisting essentially of or even consisting of) SEQ ID NO:1 or 3, where N in such sequences indicates the location where the target (non-bat) virus protein coding cDNA is inserted into the bat influenza platform HA sequence. In one or more embodiments, the NA segment is a synthetic construct comprising (consisting essentially of or even consisting of) SEQ ID NO:2 or 4, where N in such sequences indicates the location where the target (non-bat) virus protein coding cDNA is inserted into the bat influenza platform NA sequence(s).

Thus, it will be appreciated that when a new circulating influenza strain is identified, the HA and NA segments of that strain may be synthesized into cDNA and included in an expression construct along with the bat-influenza backbone segments (in the same or a different construct) for generating the chimeric viral particles. For example, the synthesized segments (e.g., SEQ ID Nos: 1-4, along with selected backbone segments SEQ ID Nos: 5-8, 10, 13, 15-19, 21, 23-24) can be inserted or cloned into suitable vectors for propagation, and preferably plasmid vectors. In one or more embodiments, individual plasmids can be generated for each of the eight influenza segments, one encoding fir each of PB2, PB1, PA, NP, M, and NS, as well as chimeric HA and NA. The plasmids are then transfected into appropriate cells for generation of the chimeric virions. The resulting cell transfection supernatants can then be incubated with various cells (e.g., primary cells or cell lines, such as MDCK, mink lung Mv1-Lu, swine testis, Vero, A549 cells, Calu-3, bat lung epithelial Tb1Lu) and/or embryonated chicken eggs and passaged followed by propagation. Suitable cells are preferably mammalian, although avian or insect cells can also be used. It will be appreciated that the virus can be passaged in cell culture and subsequently propagated in embryonated chicken eggs, although it also possible to passage the virus through embryonated chicken eggs followed by propagation in cell culture.

Regardless, the resulting chimeric virus can be used for live attenuated vaccines against influenza type A to prevent or mitigate influenza infection in the subject. As used herein, the term "vaccine" refers to an immunogenic composition capable of eliciting partial or complete immunogenic protection against a disease or condition in the subject to which it has been administered. Although vaccines are generally considered prophylactic, the vaccines may be used for therapeutic treatment of a disease or a condition. The terms "prophylactic" or "prevent," as used herein, refer to vaccines that are intended to inhibit or ameliorate the effects of a future viral infection or disease to which a subject may be exposed (but is not currently infected with). In some cases the vaccine may prevent the development of observable morbidity from viral infection (i.e., near 100% prevention). In other cases, the vaccine may only partially prevent and/or lessen the extent of morbidity due to the viral infection (i.e., reduce or mitigate the severity of the symptoms and/or effects of the infection, and/or reduce or mitigate the duration of the infection/symptoms/effects). In either case, the vaccine is still considered to "prevent" the target infection or disease in the context of this disclosure. Conversely, the terms "therapeutic" or "treat," as used herein, refer to vaccines that are intended to produce a beneficial change in an existing condition (e.g., viral infection, disease) of a subject, such as by reducing the severity of the clinical symptoms and/or effects of the infection, and/or reducing the duration of the infection/symptoms/effects.

The vaccines comprise the chimeric bat-influenza virus described herein dispersed in a pharmaceutically-acceptable carrier. The term carrier is used herein to refer to diluents, excipients, vehicles, and the like, in which the chimeric bat-influenza virus may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the chimeric bat-influenza virus or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), aqueous dextrose solutions, aqueous glycerol solutions, ethanol, normal allantoic fluid, various oil-in-water or water-in-oil emulsions, as well as dimethyl sulfoxide (DMSO) or other acceptable vehicles, and the like.

The vaccine can comprise a therapeutically effective amount of live attenuated chimeric bat-influenza virus dispersed in the carrier. As used herein, a "therapeutically effective" amount refers to the amount that will elicit the biological or medical response of a tissue, system, or subject that is being sought by a researcher or clinician, and in particular elicit some desired protective effect as against the viral infection by priming or stimulating an immune response specific for one or more strains of influenza virus (and preferably at least the target strain). One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of a chimeric bat-influenza virus described herein, and preferably from about 30% to about 90% by weight of the chimeric bat-influenza virus, based upon the total weight of the composition taken as 100% by weight. In some embodiments, combinations of more than one type of the described chimeric bat-influenza virus can be included in the composition, in which case the total levels of all such viral particles will (preferably fall within the ranges described above. Such multi-valent vaccines are preferred for use in vaccination against the flu virus.

Other ingredients may be included in the composition, such as adjuvants, other active agents, preservatives, buffering agents, salts, other pharmaceutically-acceptable ingredients, including residual amounts of ingredients used in vaccine manufacturing. The term "adjuvant" is used herein to refer to substances that have immunopotentiating effects and are added to or co-formulated in the vaccine composition in order to enhance, elicit, and/or modulate the innate, humoral, and/or cell-mediated immune response against the vaccine components. Suitable adjuvants include: aluminum salts, such as aluminum hydroxide, aluminum phosphate, alum (potassium aluminum sulfate), or mixed aluminum salts, peptides, oil or hydrocarbon emulsions, or any other adjuvant deemed suitable for human or animal use. In some embodiments, the vaccine is substantially free of any adjuvants, where the term "substantially free" means that the ingredient is not intentionally added or part of the composition, although it is recognized that residual or incidental amounts or impurities may be present in low amounts (e.g., less than about 0.1% by weight and preferably less than about 0.01% by weight, based upon the total weight of the composite taken as 100% by weight). Other active agents that could be included in the composition include other antiviral compounds or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used. Antibiotics can also be used as part of vaccine production and may be present in small amounts in the vaccine, such as neomycin, polymyxin B, streptomycin and gentamicin. In some embodiments, the vaccine composition is substantially free of any other active (immunogenic) agents, other than the live attenuated chimeric bat-influenza virus and optional adjuvant, dispersed in the carrier.

In use, the vaccine composition is administered to a subject. Various routes of administration can be used depending upon the particular carrier and other ingredients used. For example, the vaccine can be injected intramuscularly, subcutaneously, intradermally, or intravenously using a needle and syringe, or a needleless injection device. The vaccine can also be administered mucosally, such as intranasal administration. For intranasal administration, the vaccine composition is usually administered through the nasal passage as drops, large particle aerosol (greater than about 10 microns), or spray into the upper respiratory tract. While stimulation of a protective immune response with a single dose is preferred, additional dosages can be administered, by the same or different route, to achieve the desired prophylactic effect. The vaccine can also be administered using a prime and boost regime if deemed necessary. In some embodiments, the methods described herein are useful for preventing the occurrence or incidence of influenza infection and/or preventing the effects of influenza infection, as described above.

In some embodiments, the vaccine can be provided in unit dosage form in a suitable container. The term "unit dosage form" refers to a physically discrete unit suitable as a unitary dosage for human or animal use. Each unit dosage form may contain a predetermined amount of the vaccine (and/or other active agents) in the carrier calculated to produce the desired effect. In other embodiments, the vaccine can be provided separate from the carrier (e.g., in its own vial, ampule, sachet, or other suitable container) for on-site mixing before administration to a subject. A kit comprising the vaccine is also disclosed herein. The kit further comprises instructions for administering the vaccine to a subject. The virus can be provided as part of a dosage unit, already dispersed in a pharmaceutically-acceptable carrier, or it can be provided separately from the carrier. The kit can further comprise instructions for preparing the virus for administration to a subject, including for example, instructions for dispersing the virus in a suitable carrier.

All results indicate that modified bat viruses can be used as live attenuated vaccines. Advantageously, there are no safety concerns regarding reassortment between a bat-influenza-based attenuated live vaccine and endemic circulating influenza viruses. Thus, the vaccine virus strains used are "non-reassortant." Using the methodology and technology described herein, different subtype attenuated influenza vaccines can be developed and used for swine and other species including, but not limited to, human, canine, equine, feline, avian, primate, rodents, and the like.

The methods can be also applied for clinical research and/or study. Thus, kits for study and/or generation of additional chimeric virus strains are also described herein. The kits comprise vectors (plasmids) as described herein encoding for the bat-influenza backbone genome segments to produce the platform virus. The kit can also include vectors encoding for the surface proteins HA and NA of the target virus. Alternatively, such sequences can be determined by the end-user. The kit may include plasmids for subsequently inserting the determined HA and NA sequences for generation of the chimeric virus. The kit may further include additional components, including cells, culture medium, buffers, along with instructions for their use to generate the chimeric viruses.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used a list of two or more items, means that any one of the listed items can be employed h itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Results

Figure 2A:
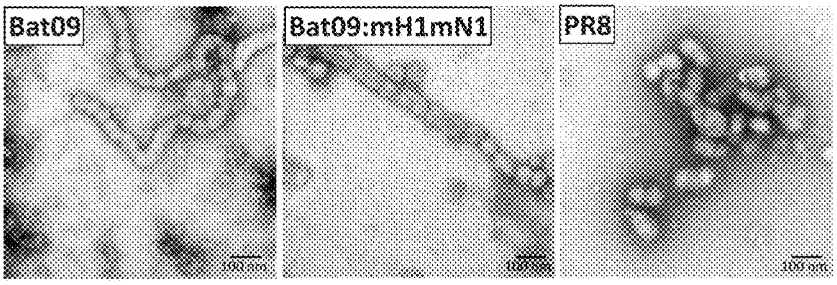
FIGS. 2A-2E related to generation of viruses relevant to Bat09.

1. Synthetic Genomics Generated Bat-Influenza Virus-Like Particles but they were not Infectious in Many Host Cell Substrates Lack of infectious particles in the original bat specimens is a potential factor in the inability to isolate/culture bat-influenza using multiple host cell substrates. Based on digital sequence information published by Tong et al. (*A distinct lineage of influenza A virus from bats. Proc Natl Acad Sci USA* 109: 4269-4274), we synthesized the complete genome of A/little yellow-shouldered bat/Guatemala/164/2009 (H17N10) (FIG. 1) and cloned it into reverse genetics plasmids to rescue this putative bat-influenza virus (Bat09). Thousands of spherical influenza-like particles budded into the supernatants of human cells (293T) transfected with the Bat09 reverse genetics plasmids (FIG. 2A). The supernatants were inoculated into embryonated chicken eggs and cell lines derived from many species (canine (MDCK), mink (Mv1-Lu), swine (ST), African green monkey (Vero), human (A549, Calu-3), and free-tailed bat (*Tadarida brasiliensis*, Tb1Lu); however, none of the host cell substrates tested supported productive virus infection. (determined by serial passage and subsequent real-time RT-PCR).

Previous biochemical and structural studies with purified proteins of Bat09 hemagglutinin (HA) and neuraminidase (NA) indicate that the HA doesn't bind to canonical sialic acid receptors of influenza viruses and the NA doesn't have neuraminidase activity, which is characteristic of IAV and IBV NAs. To further examine if the HA and NA proteins are the major blocks to the propagation of the Bat09 virus, we attempted to rescue reassortant viruses that contained the 6 internal protein coding vRNAs (PB2, PB1, PA, NP, M, and NS) from Bat09 and the surface glycoprotein vRNAs (HA and/or NA) from a recombinant strain A/Puerto Rico/8/1934 (PR8). PR8 is a lab adapted H1N1 virus that has been used for many years in research and vaccine settings because it replicates efficiently in embryonated chicken eggs, cell lines (e.g., MDCK) and in the mice, but has low risk to humans.

Figure 2B:
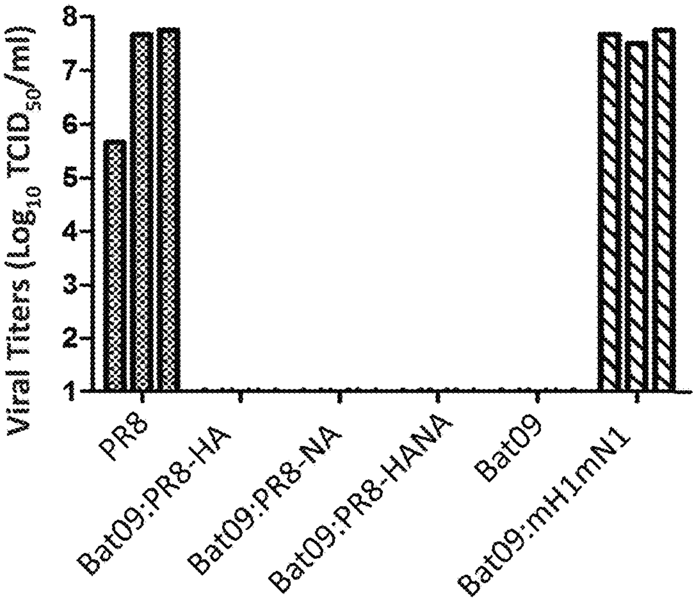

However, the three PR8-HA/NA reassortant genotypes containing the Bat09 internal protein vRNAs couldn't be rescued following transfection (FIG. 2B). While the Bat09 internal protein/vRNAs are capable of generating proteins and producing influenza-like particles, they may have critical mutations that were inhibiting infectivity, or they can't cooperate efficiently with the PR8-HA/NA proteins/vRNAs.

Figure 2C:
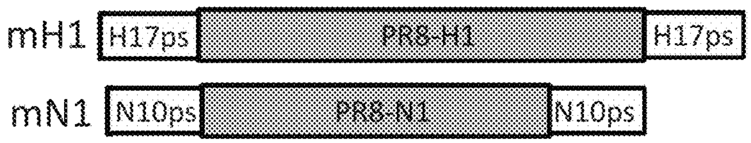
Figure 2D:
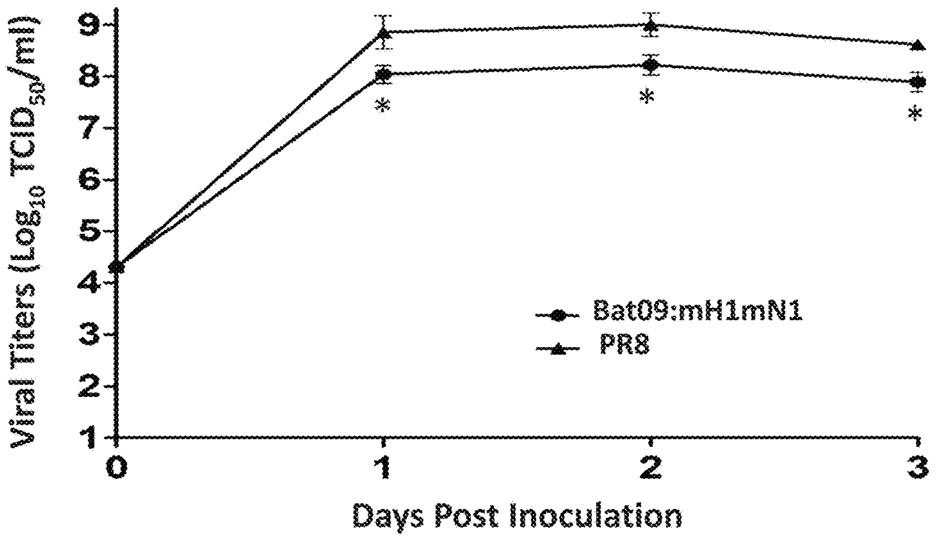
Figure 2E:
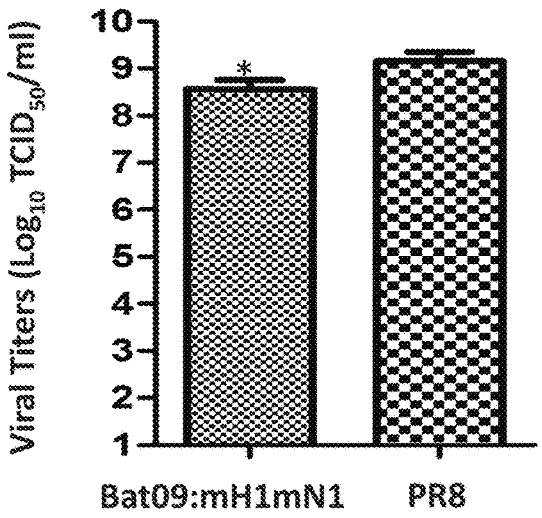

2. Modified Bat-Influenza Virus could be Generated and it Replicated Efficiently In Vitro, in Ovo and In Vivo To further address the inability to rescue Bat09 or the Bat09:PR8-HA/NA reassortants, we created a modified HA nRNA (mH1; SEQ ID NO:30) that contained the protein coding region from PR8-H1 (SEQ ID NO:29) flanked by putative cis-acting terminal packaging signals from Bat09 that we hypothesized would be similar to the regions known to be central to packaging of A/WSN/1933 and PR8 (FIG. 2C and FIG. 3). The Bat09 NA gene segment was modified using a similar strategy to replace the NA coding region with PR8-N1 (SEQ ID NO:32), while the putative bat NA packaging signals were retained (mN1; SEQ ID NO:33) (FIG. 2C and FIG. 3). Co-expression of the mH1 and mN1 vRNAs with the six Bat09 internal protein vRNAs efficiently rescued a reassortant Bat09:mH1mN1 virus (FIG. 2B). The reassortant Bat09:mH1mN1 formed particles similar to that of Bat09 (FIG. 2A) and replicated robustly in vitro and in ovo (FIGS. 2D, 2E). Next generation sequencing demonstrated that the consensus sequence of the virus stocks from 1 passage in MDCK cells or embryonated chicken eggs was identical to that of the reverse genetics plasmids. Furthermore, even after 3 passages in MDCK cells, we still didn't identify any nucleotide polymorphisms accounting for >10% of the genomic population that would suggest strong selective pressure on Bat09 genes or the modified HA/NA genes of PR8.

Figure 4A:
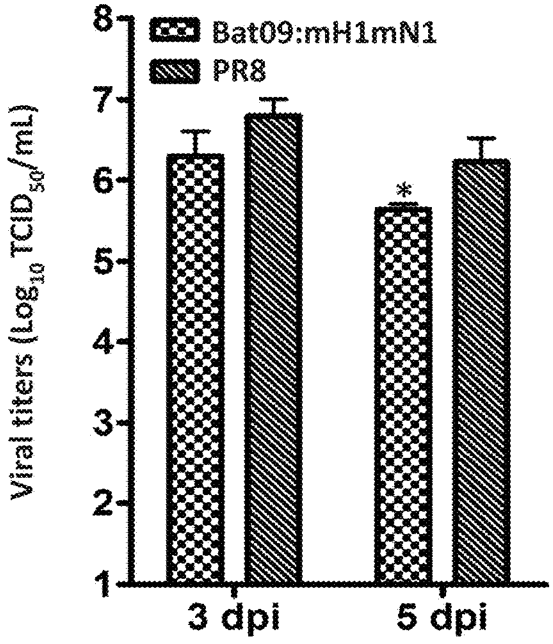
FIGS. 4A-4E show data on pathogenicity of Bat09: mH1mN1 and PR8 viruses in mice.
Figure 4B:
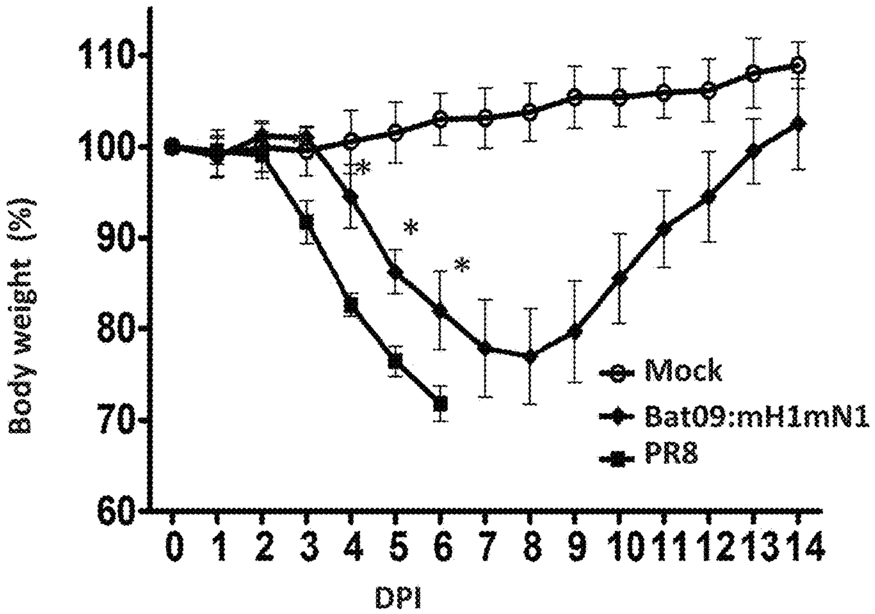
Figure 4C:
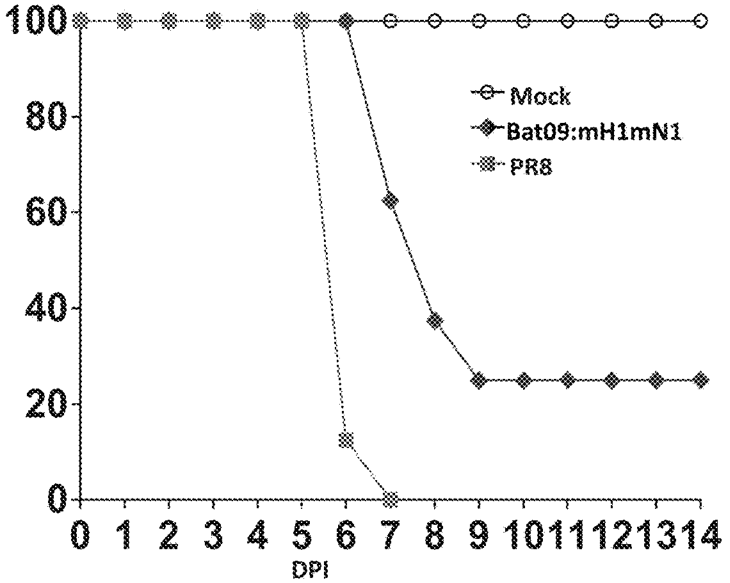
Figure 4D:
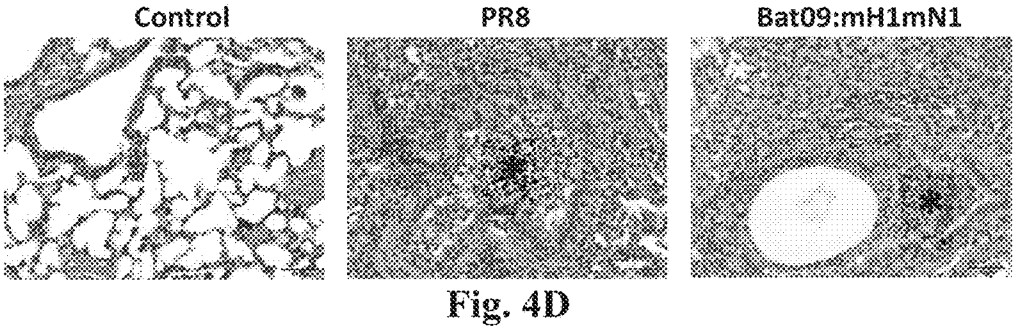
Figure 4E:
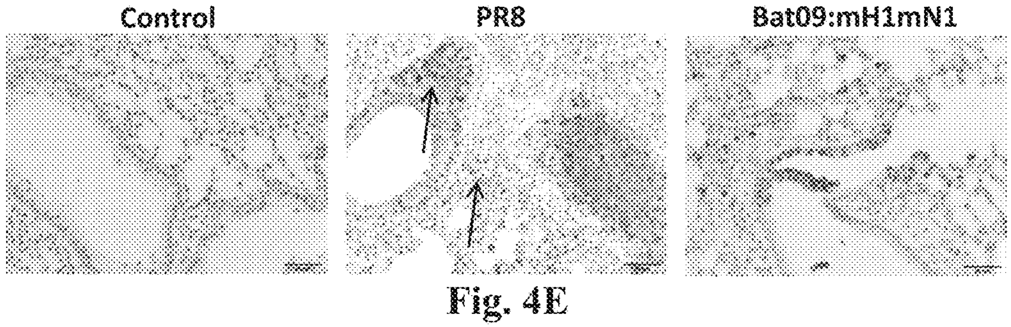

To investigate whether Bat09:mH1mN1 is able to infect and replicate in mice, a mouse study was performed using the mouse-adapted PR8 IAV as a positive control. Bat09:mH1mN1 replicated efficiently in mouse lungs (FIG. 4A), and caused significant weight loss as early as at 4 days post inoculation (4 dpi) (FIG. 4B). The virulence of Bat09:mH1mN1 (75% mortality) was close to that of the PR8 virus (100% mortality) (FIG. 4C). Histopathological analysis showed that the Bat09:mH1mN1 virus caused typical influenza-like lesions characterized by a varying degree of broncho-alveolar epithelial degeneration and necrosis, and interstitial pneumonia. The peribronchiolar and perivascular areas were infiltrated by moderate numbers of lymphocytes and plasma cells (FIG. 4D). The histopathology identified correlates with presence of virus antigen in the mouse lungs (FIG. 4E).

Next generation sequencing was used to determine if the Bat09 vRNAs were genetically stable in mice. Although nucleotide polymorphisms (at the level of 12%-36%) were detected at sporadic loci throughout the Bat09 vRNAs, each lung sample only had one such polymorphism on average, and none of the mutations were found in more than one mouse. Nonetheless, serial passage of this virus in mice may identify mutations in the Bat09 backbone critical to replication/pathogenesis in mice. We did identify a low level nucleotide polymorphism in the modified PR8 HA at residue at 187 that emerged in multiple Bat09:mH1mN1 inoculated mouse lung samples collected at 3 and 5 dpi (HA-K187E, 10%-20% of the genomic population). This unanticipated result may have also occurred in PR8 inoculated mice; however the lung specimens from these mice were not sequenced.

Figure 5A:
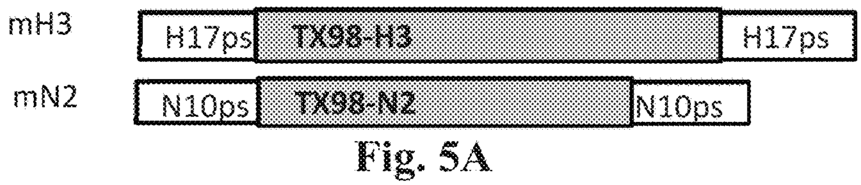
FIGS. 5A-5D show data related to the Bat09:mH3mN2 construct, and pathogenicity of Bat09:mH3mN2 and TX98 viruses in mice.
Figure 5B:
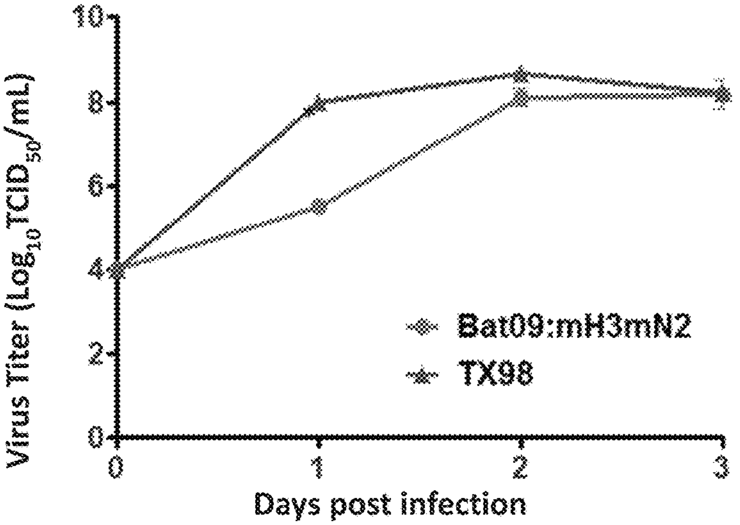
Figure 5C:
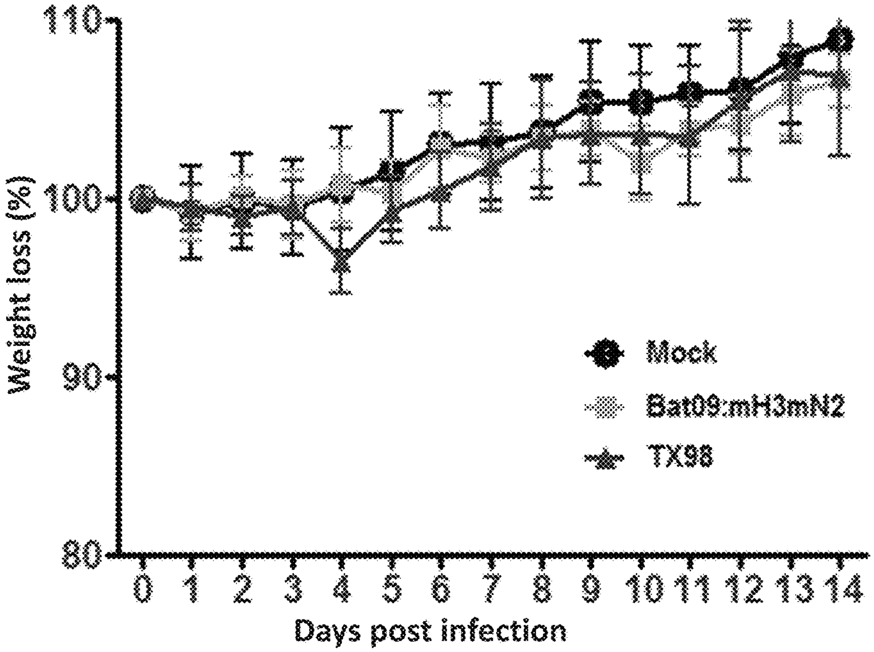
Figure 5D:
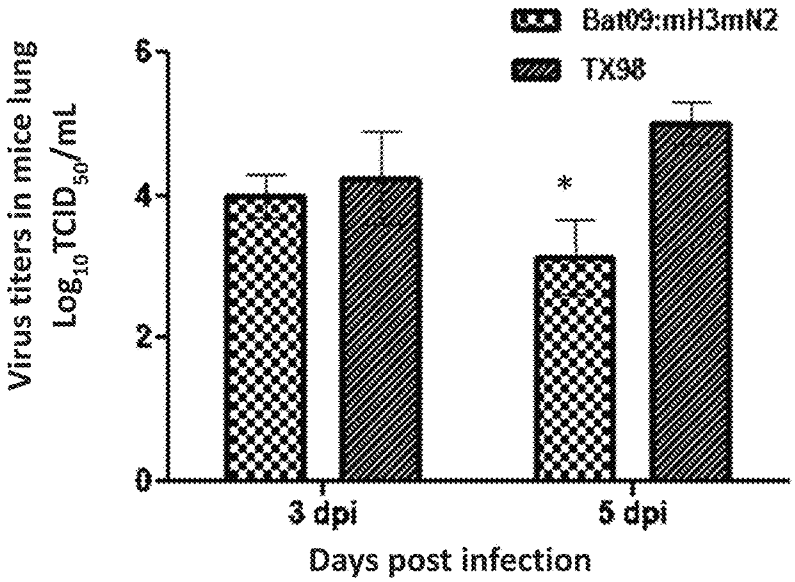

The virulence of the Bat09:mR1mN1 in mice could partly result from the H1 and N1 of the mouse adapted PR8 virus. To further investigate pathogenicity of Bat09-like viruses we rescued another modified Bat09 virus that expresses H3N2 surface glycoproteins from A/swine/Texas/4199-2/1998 (H3N2) (TX98), which we have used in pigs previously. The HA/NA vRNAs of Bat09:mH3mN2 were modified using a similar strategy used to generate the mH1/mN1, whereby the coding regions of Bat09 glycoproteins were replaced with TX98 H3N2, while the putative Bat09 packaging signals were retained (mH3/mN2) (FIG. 5A). To construct the mH3, TX98-HA coding region was flanked by the putative packaging regions from Bat09-HA and all potential start codons in the Bat09-HA 5' packaging region were mutated. To construct the mN1, PR8-NA coding region was flanked by the putative packaging regions from Bat09-NA and all start codons in the Bat09-NA 5' packaging region were mutated. The rescued Bat09:mH3mN2 virus replicated to peak titers close to that of TX98 (FIG. 5B) and both viruses were inoculated into mice to compare the morbidity (weight loss), mortality and virus replication at various times post inoculation. All mice survived infection and both viruses (Bat09:mH3mN2 and TX98) caused little effect on weight gain as compared to the mock inoculated animals (FIG. 5C), indicating little overall disease. Titration of virus in the lung tissues showed that the Bat09:mH3mN2 virus replicated as efficiently as the TX98 control in the mice at early time points, yet it appeared to be cleared more rapidly (FIG. 5D). This data suggests that some of the pathogenicity observed in the Bat09:mH1mN1 infected mice likely results from the mouse adapted HA/NA of PR8. However, it is clear that the bat influenza internal protein vRNAs do support replication of the modified viruses (Bat09:mH1mN1 and Bat09:mH3mN2) in vitro, in ovo, and in the mouse lungs. The slightly lower replication efficiency and pathogenicity of those two viruses compared to the corresponding PR8 and TX98 viruses could be ascribable to either the nature of the Bat09 internal protein vRNAs or the engineering of the modified HAs and NAs.

Figure 6A:
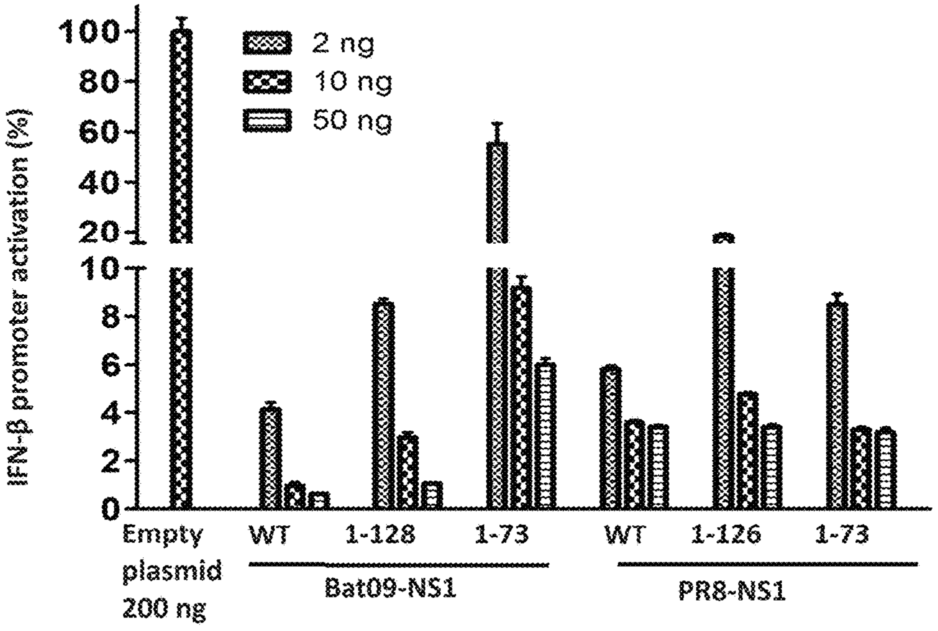
FIGS. 6A-6C show data relating to the in vitro properties of Bat-NS1 mutants.

3. Bat-Influenza NS1 Shows Strong Innate Immune Suppression in Human Cells and in Mice Bat-influenza viruses appear to have diverged from IAV a very long time ago and their internal protein vRNAs have many unique features that are not seen in IAVs. Therefore, the biological roles of the various vRNA segments and their protein products are likely to have both similarities and intriguing differences. Many deadly bat viruses (e.g., filoviruses) have evolved powerful molecular mechanisms that inhibit host (e.g., human) immune responses. Therefore, to gain an understanding of how bat-influenza viruses may evade the host innate immune response we analyzed the Bat09 NS1 protein using interferon induction experiments and carboxy-terminal truncation mutations known to attenuate IAVs. The NS1 protein of IAVs is critical for pathogenicity of many strains because of its ability to antagonize the host interferon response. To compare the direct effect of Bat09-NS1 and PR8-NS1 on interferon-β production, we expressed the proteins ectopically in human HEK-293T and then infected them with Sendai virus to stimulate the innate immune response. Activation of interferon-β promoter was determined by a luciferase mediated reporter assay. Bat09-NS1 inhibited host interferon-β induction comparable to that of the PR8-NS1, and carboxy-terminal truncation of Bat-NS1 protein (NS1-128 and NS1-73, see FIG. 3C for diagram) decreased its ability to inhibit interferon-β production (FIG. 6A). These results are consistent with the attenuating effect that these NS1 truncations have on PR8 (FIG. 6A) and other IAV NS1 proteins; thereby, providing a strategy to generate live attenuated influenza vaccines.

Figure 6B:
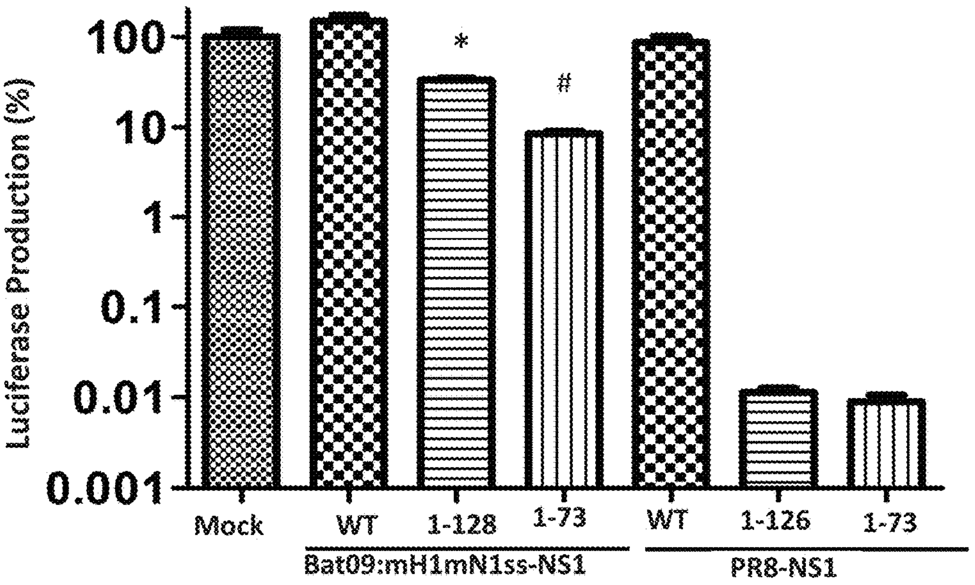
Figure 6C:
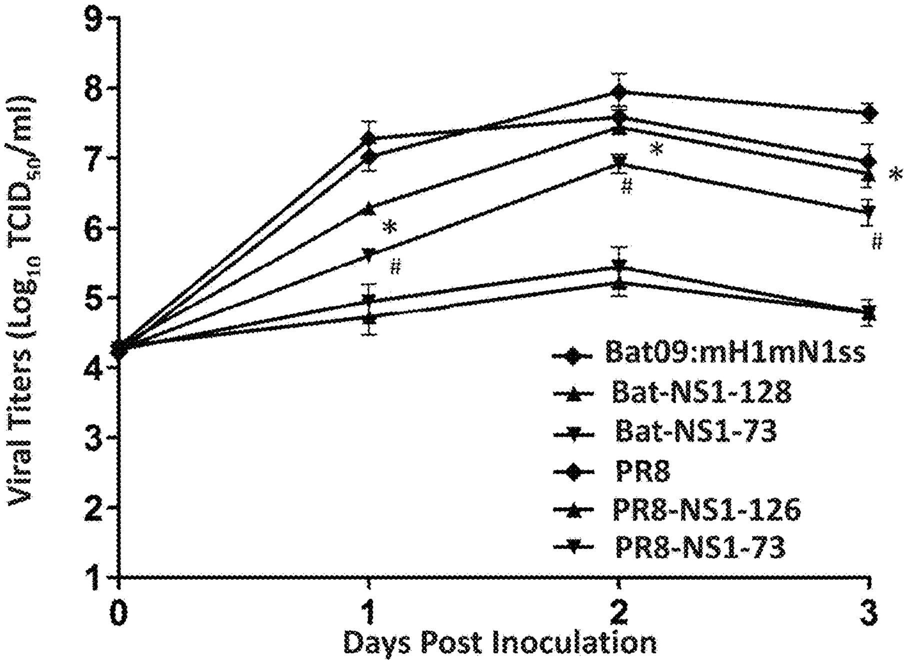

A VSV-luciferase virus mediated bioassay was also performed to compare the effect the NS1 truncations have on the Bat09 viruses' ability to inhibit host innate immune response. The replication of the VSV-luciferase virus, which is sensitive to innate immune activation, is inversely correlated with type 1 interferon induced by influenza virus. Truncation of the Bat09-NS1 modestly reduced VSV replication, whereas truncation of the PR8-NS1 severely inhibited VSV replication (i.e., luciferase expression) (FIG. 6B). These results were confirmed by analysis of influenza virus replication kinetics in a human lung epithelial cell line (FIG. 6C). The Bat09-NS1 truncated viruses (Bat09:mH1mN1ss-NS1-128 and Bat09:mH1mN1ss-NS1-73) replicated to titers of $10^6$-$10^7$ $TCID_{50}$/ml (near wild type NS1; Bat09: mH1mN1ss), whereas the PR8-NS1 truncation mutants had 100-1000 fold lower titers than PR8 (FIG. 6C, FIG. 3A-C for gene and virus diagrams).

Figure 7A:
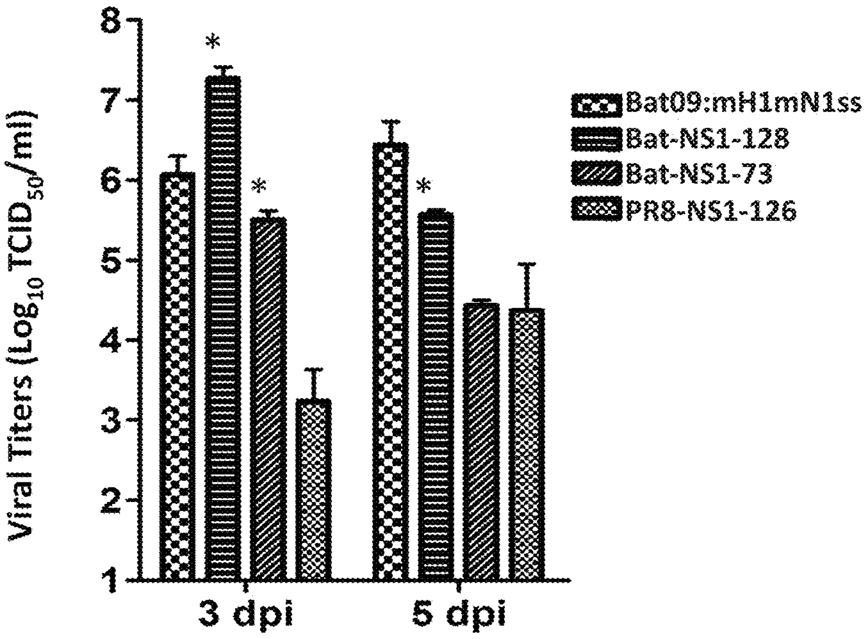
FIGS. 7A-7C show data relating to the pathogenicity of Bat-NS1 mutants in mice.
Figure 7B:
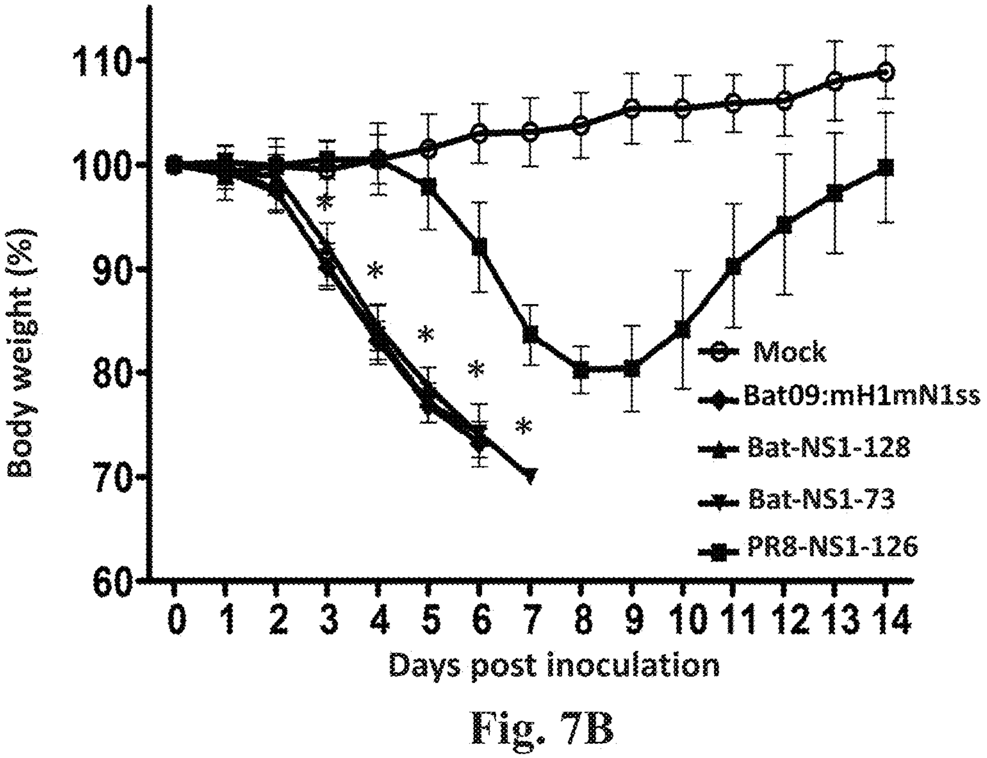
Figure 7C:
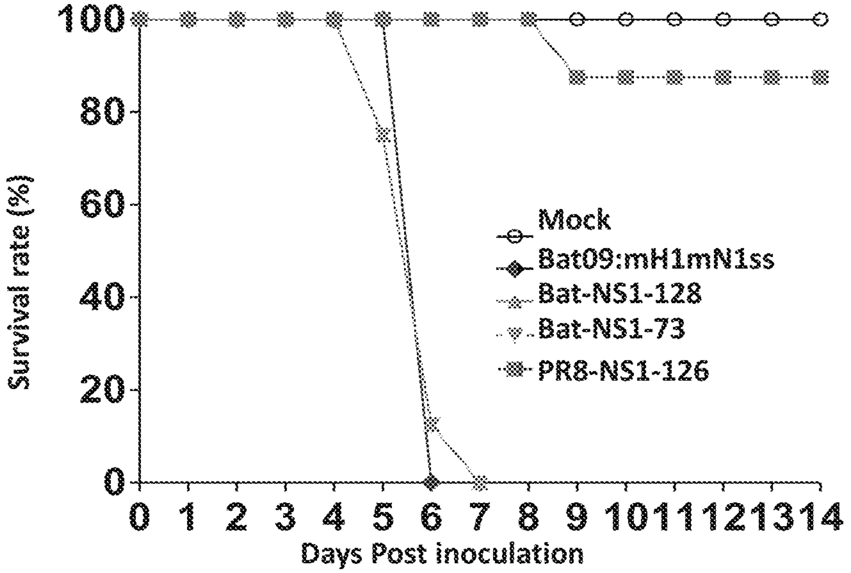

To analyze the impact of these Bat NS1 truncation mutations in vivo we inoculated mice with the same panel of modified Bat09 viruses, or the PR8-NS1-126 as a control. In contrast to the significant attenuation conferred by the truncated NS1 in PR8 (PR8-NS1-126), recombinant bat-influenza viruses with truncated NS1 genes (Bat09: mH1mN1ss-NS1-128 and Bat09:mH1mN1ss-NS1-73) replicated efficiently in the lungs (FIG. 7A), caused significant morbidity (FIG. 7B), and remained 100% lethal in mice (FIG. 7C). Altogether the NS1 studies show that the Bat09 NS1 protein inhibits host interferon-β production and carboxy-terminal truncation mutations reduce its ability to antagonize this response, likely through mechanisms similar to IAV (FIG. 6A). However, in contrast to IAV, truncation (NS1-128, NS1-73) of the Bat09 NS1 didn't dramatically impact the viruses' ability to antagonize the host innate response, or replicate and cause disease in mice (FIGS. 6B, C and FIG. 7).

Figure 8A:
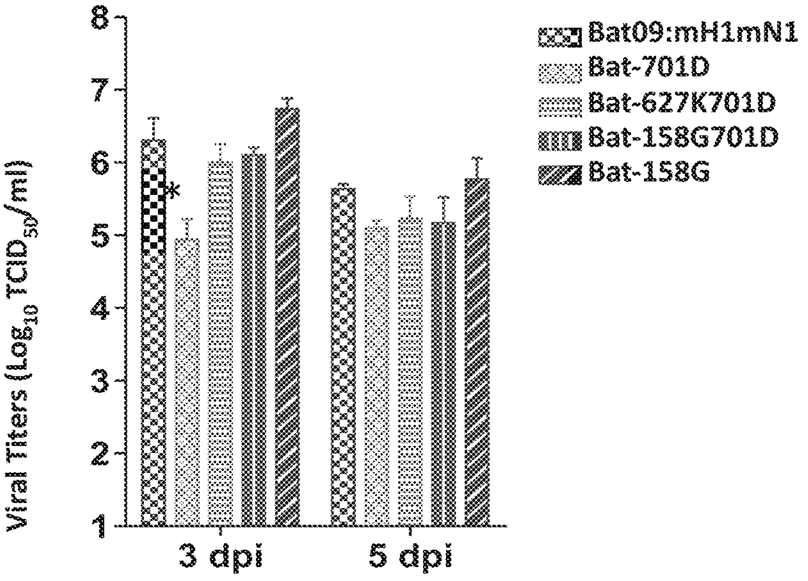
FIGS. 8A-8C show data relating to the pathogenicity of Bat-PB2 mutants in mice.
Figure 8B:
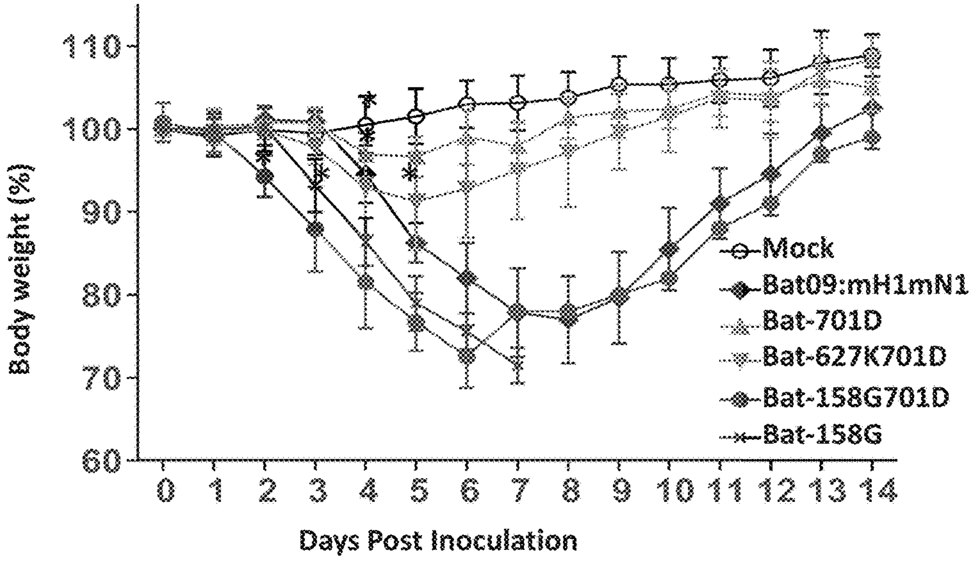
Figure 8C:
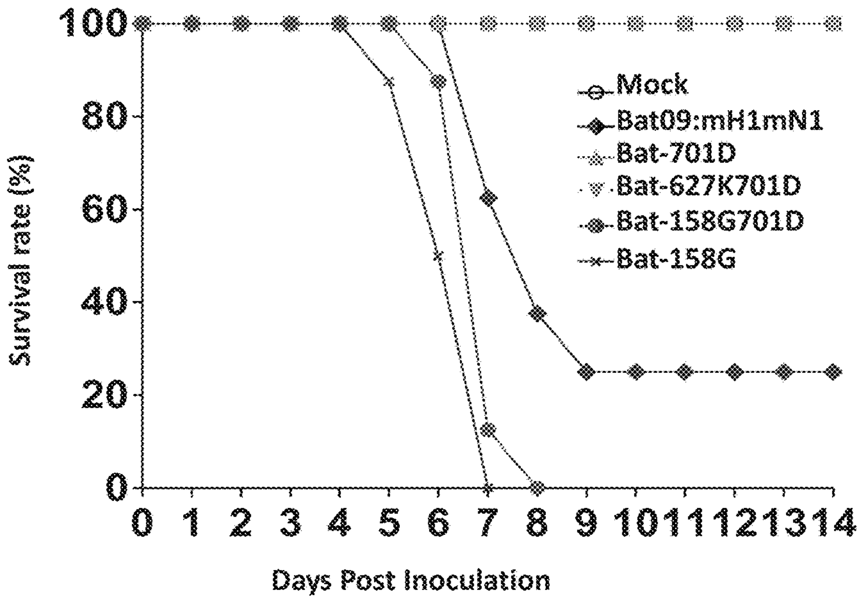

4. Pathogenesis of the Modified Bat09 Virus can be Manipulated by Amino Acid Substitutions at Residues Important in Virulence of IAVs We analyzed the Bat09 PB2 gene because of its central role in the species specificity of IAVs, and some of the critical residues involved are known to be virulence determinants in mice and ferrets. Asparagine (N) 701 in the PB2 protein is a mammalian-signature in IAVs and when this residue was mutated to aspartic acid (D, an avian-signature) in the modified Bat09 (Bat-701D), it decreased virus titers in lungs (FIG. 8A), morbidity (minor weight loss) (FIG. 8B), and resulted in 100% survival (FIG. 8C). The bat-influenza PB2 also has a serine (S) residue at position 627, which is unlike either mammalian or avian IAVs. Replacing the serine 627 with the mammalian-signature residue lysine (K) in the context of 701D (Bat-627K/701D) increased virus replication in the lungs but only caused slightly more weight loss (compared to the Bat-701D virus) and it remained attenuated in mice (FIG. 8A-C). In contrast, introducing another virulence marker PB2-E158G into the PB2-N701D virus (Bat-158G/701D) dramatically increased the pathogenicity of the Bat09 virus (100% mortality), which was higher than the Bat09 virus with wild type PB2 (Bat09:mH1mN1, FIG. 8A-C). In addition, introducing the PB2-E158G (Bat-158G) into the wild type PB2 resulted the most significant increase of virus replication, morbidity, and mortality (FIG. 8A-C), indicating there is an additive effect between the two virulence determinants (PB2-158G and PB2-701N) in the Bat09 PB2. All viruses collected from mouse lungs were deep sequenced to confirm the stability of the engineered mutations and although sporadic nucleotide polymorphisms (10%-44%) were detected in the viral genomes (1 to 2 such polymorphisms per mouse sample on average), none of them occurred at the engineered loci. The high genetic stability of the modified Bat09 viruses in mice is consistent with the notion that the bat influenza viruses are mammalian viruses that have, been evolving and adapting in the bats for a long period of time.

Figure 9:
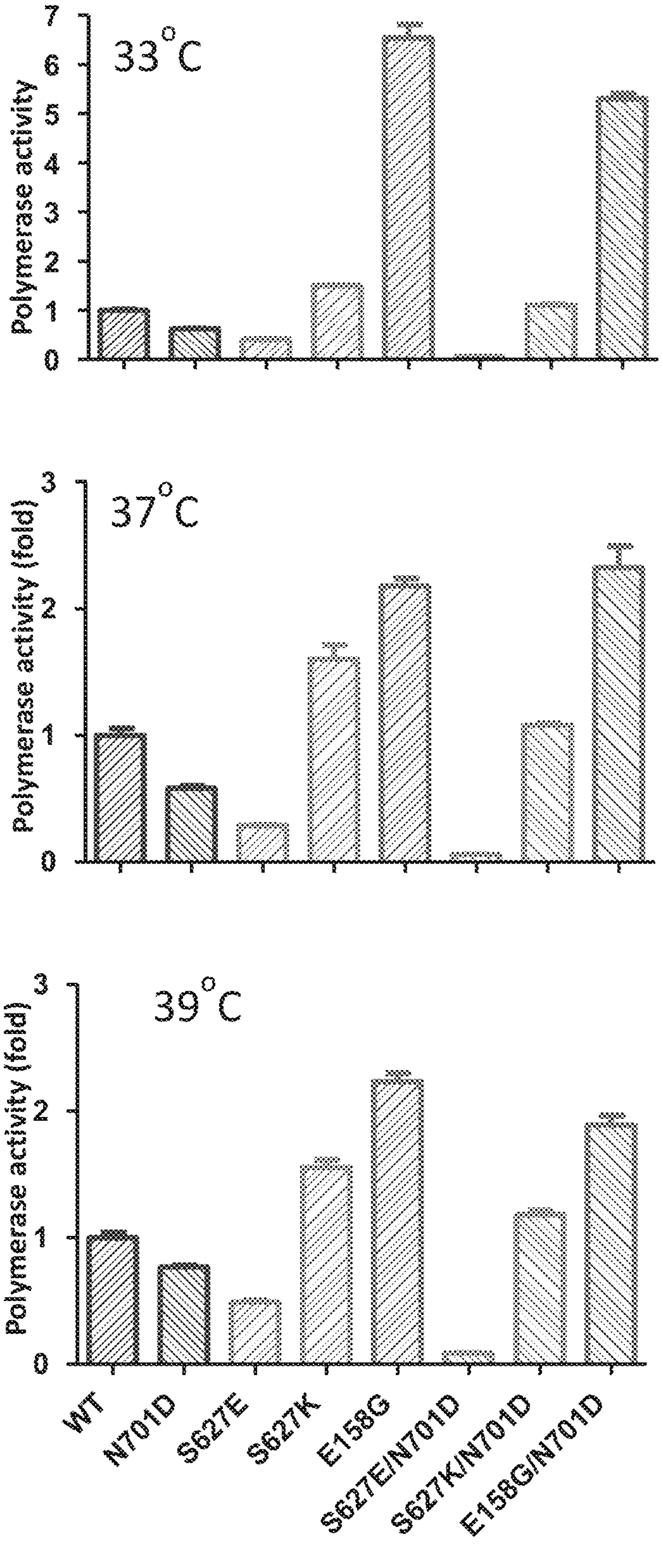
FIG. 9 shows graphs for polymerase activity of Bat09 with wild type and mutant PB2 based upon a luciferase mediated mini-genome replication assay was performed at 33° C., 37° C., and 39° C. by co-transfecting 293T cells with Bat09 PB2 (WT or mutant), PB1, PA, NP, and a vRNA-like luciferase reporter. Relative luciferase activity were determined to represent the viral polymerase activity. *, $P<0.05$, compared to WT.

To determine the molecular basis for the altered pathogenicity imparted by the various mutations in the PB2 we examined their effects on the viral polymerase activity in human 293T cells using a luciferase-mediated mini-genome replication assay (FIG. 9). At all temperatures tested, the PB2-N701D mutation decreased the polymerase activity and the PB2-E158G mutation enhanced the polymerase activity, consistent with the decreased and increased pathogenicity in mice, respectively (FIG. 8). Interestingly, the PB2-627S showed intermediate polymerase activity compared to the PB2-627K and PB2-627E (FIG. 9). In addition, the polymerase activity of the PB2-158G and PB2-627E/K mutants decreased proportionally when they were combined with the PB2-701D mutation (FIG. 9). This result is consistent with the observation that Bat-158G/701D appeared to be less pathogenic than the Bat-158G virus (FIG. 9). Collectively, the data collected on the Bat09 PB2 show that amino acid residues known to be important in replication, species specificity, transmission, and/or pathogenesis of IAV are important in the replication and pathogenesis of Bat09.

Figure 3A:
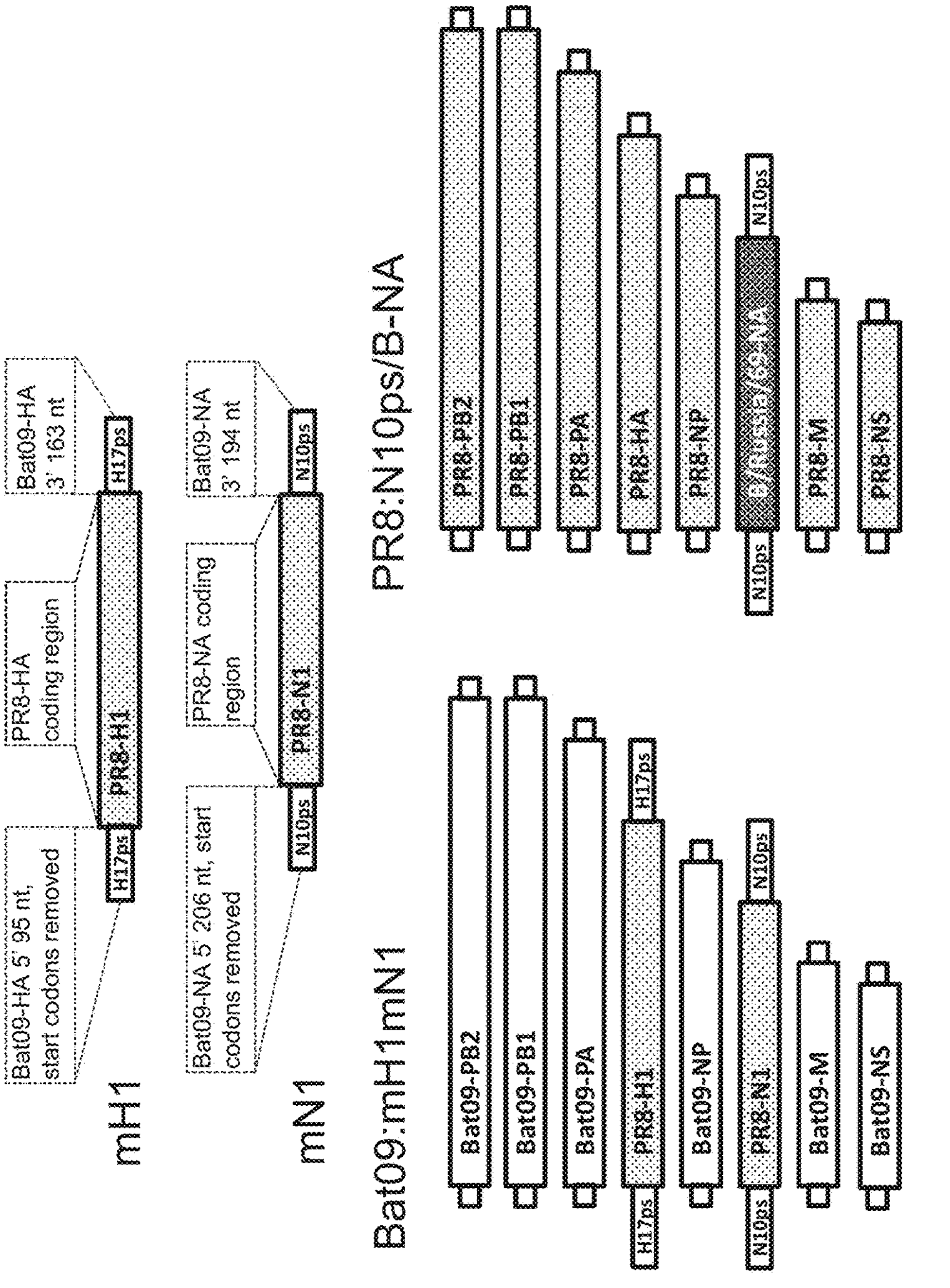
FIGS. 3A-3E show diagrams of select constructs and viruses used in this study. All constructs shown are in cDNA sense complementary to viral RNA.
Figure 3B:
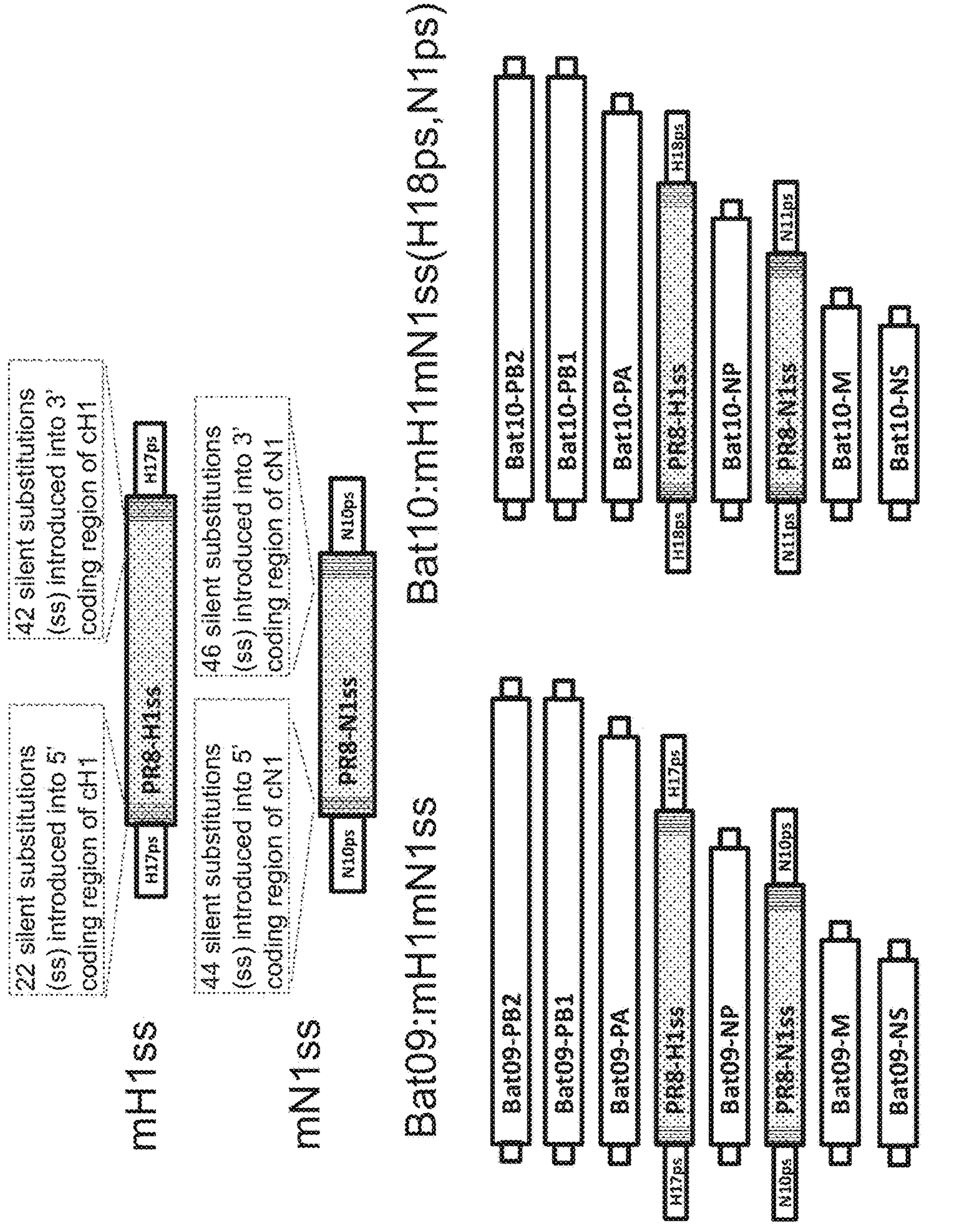
Figure 3C:
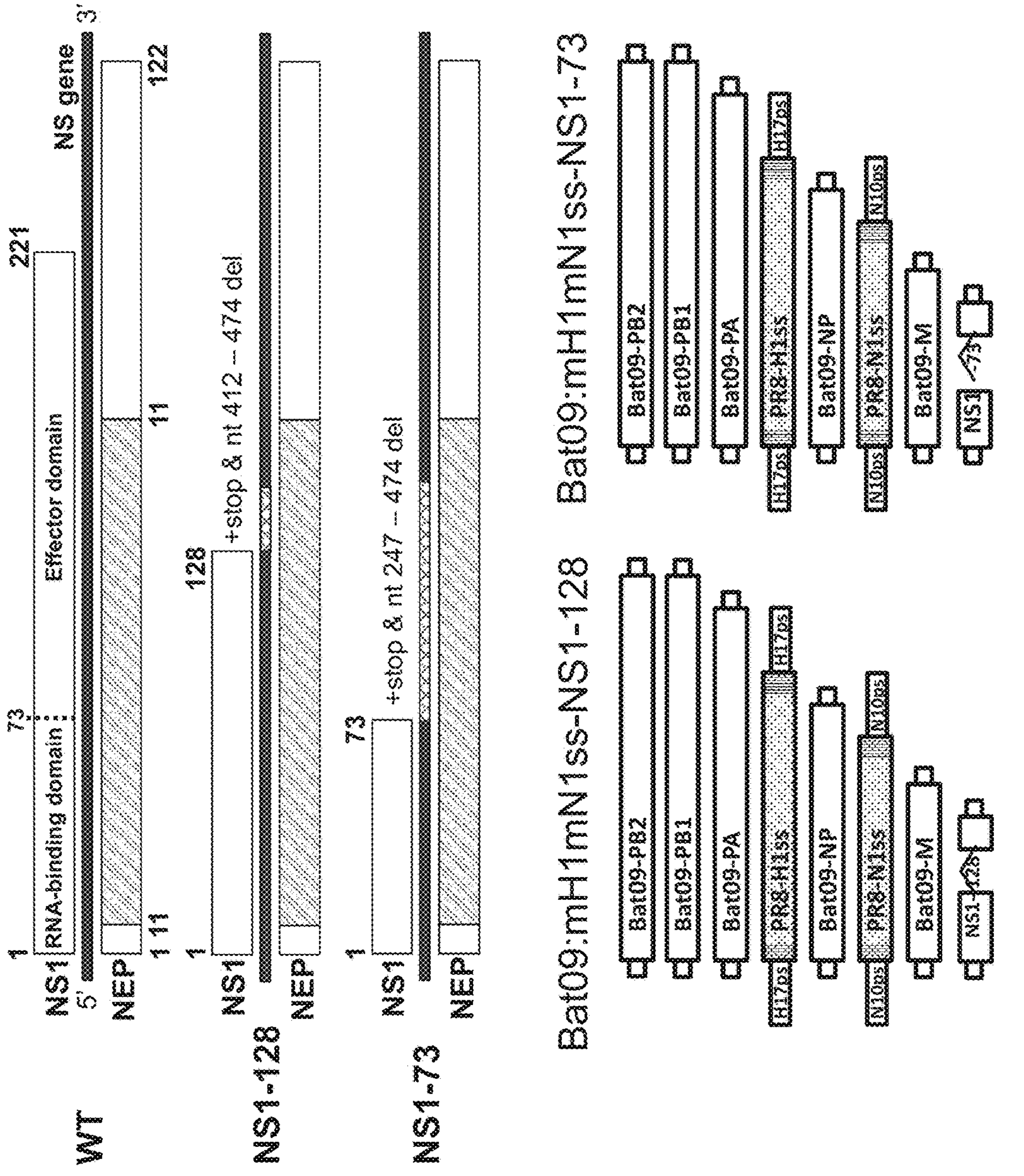
Figure 3D:
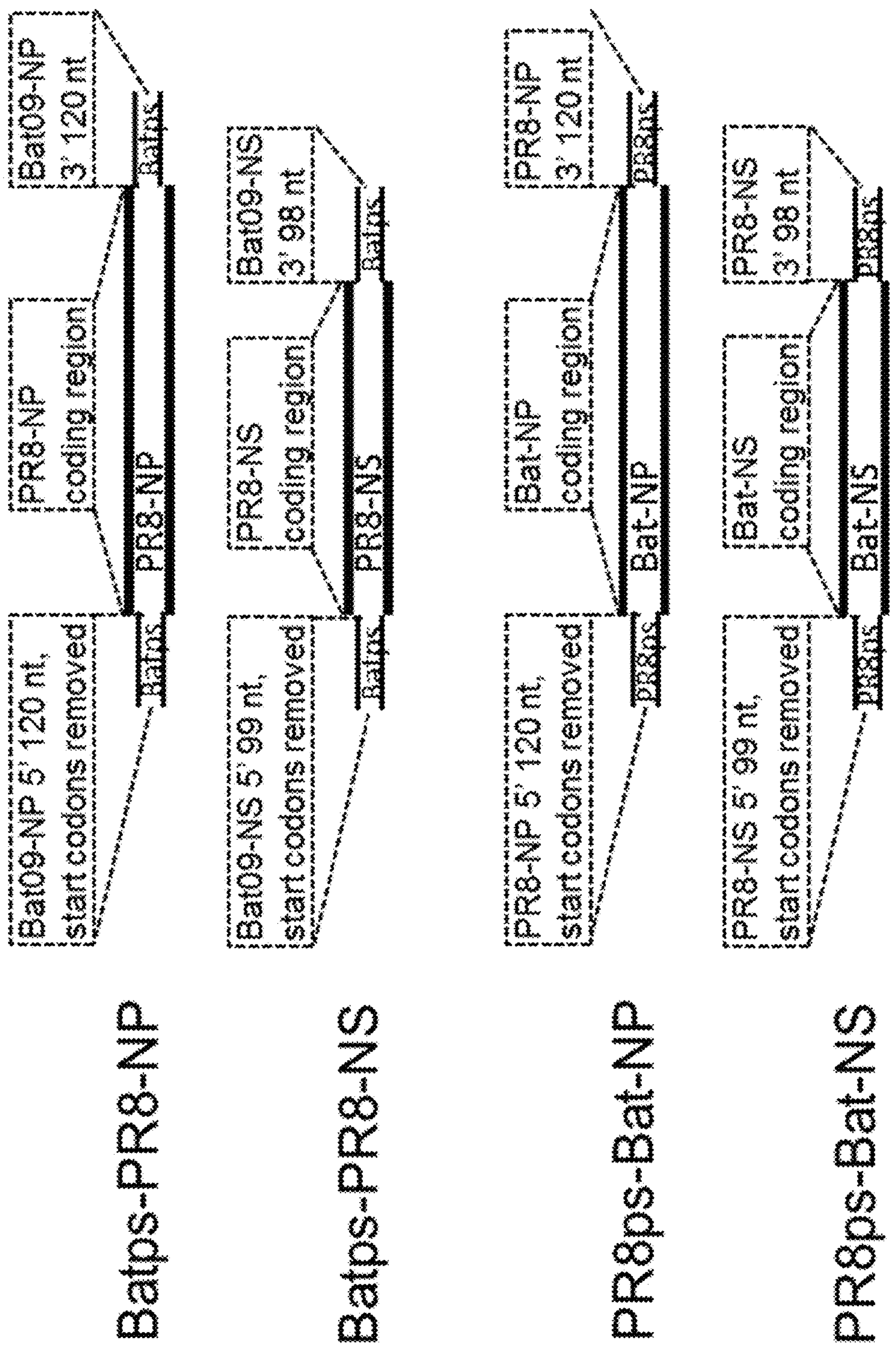
Figure 3E:
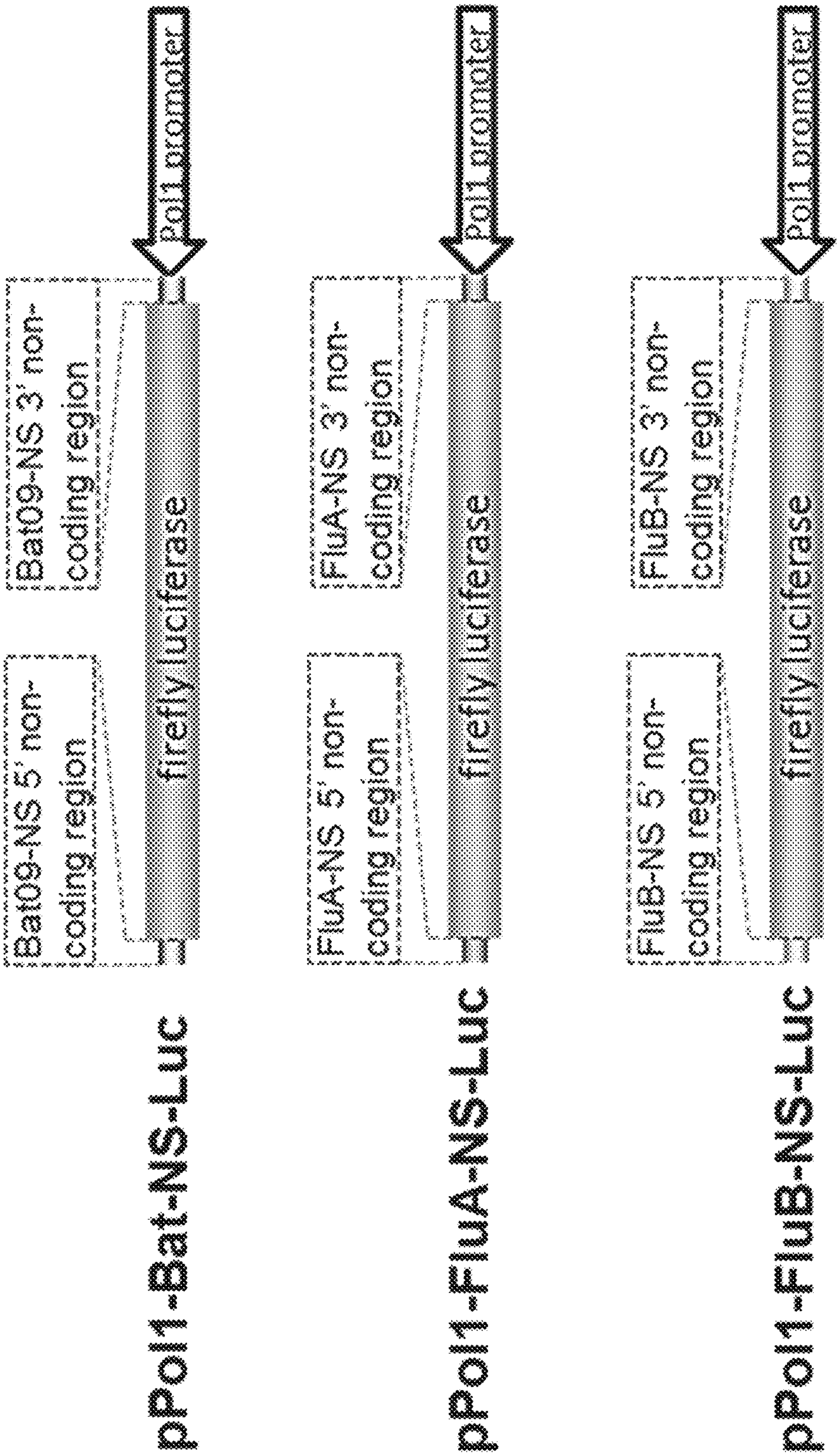
Figure 10:
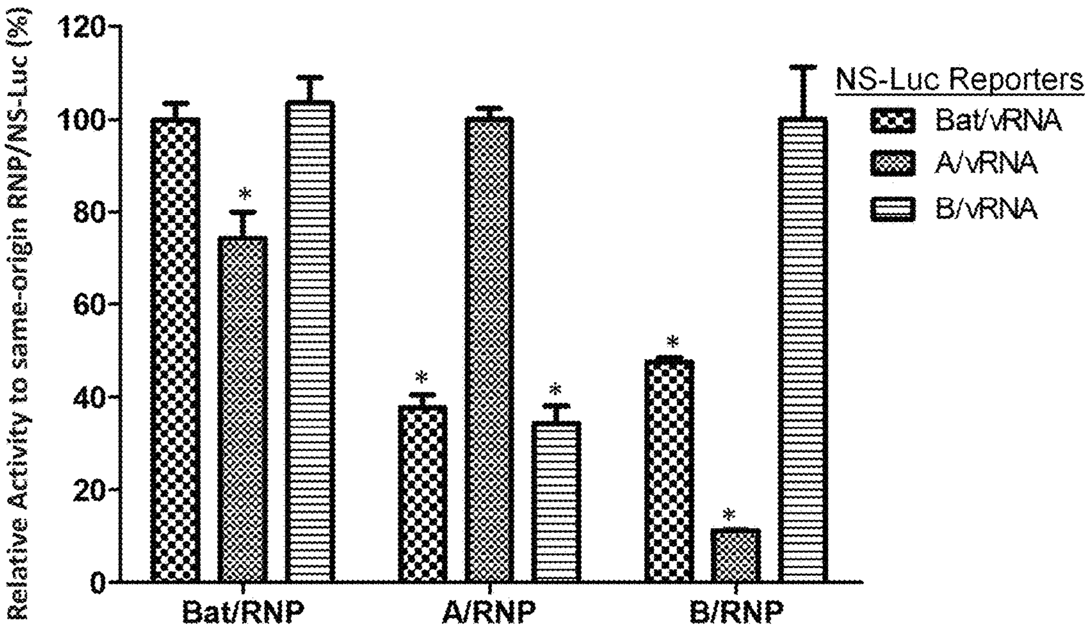
FIG. 10 is a graph showing the compatibility between RNPs and viral RNA promoters from different viruses. Left, RNP from Bat09 and luciferase reporter flanked by NS non-coding regions from bat-influenza virus, IAV, and IBV. Middle, RNP from influenza A and the three luciferase reporters. Right, RNP from IBV and the three luciferase reporters. Within each group of RNP, * indicates $P<0.05$, compared to the vRNA reporter from the same type of virus as the RNP.
Figure 11A:
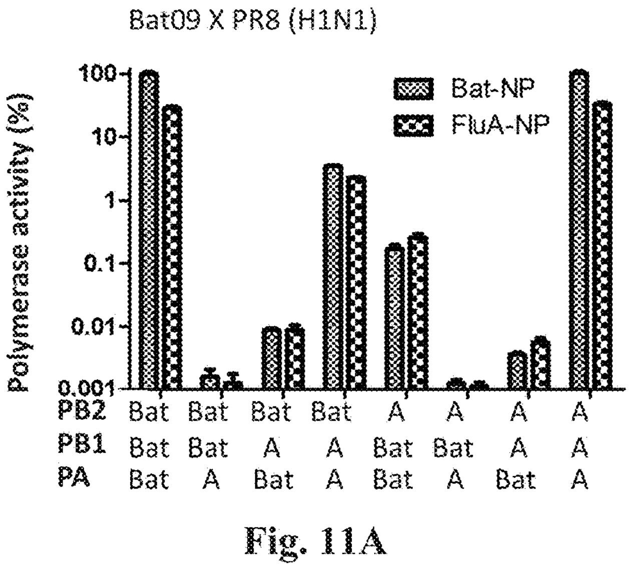
FIGS. 11A-11K show data from the mini-genome replication assay for compatibility of the PB2, PB1, PA and NP originated from Bat09 and other influenza viruses.
Figure 11B:
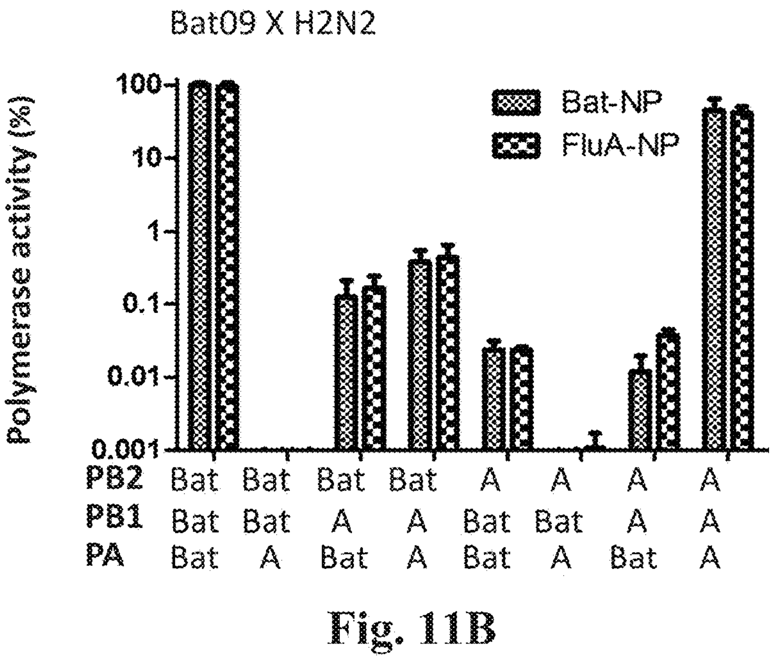
Figure 11C:
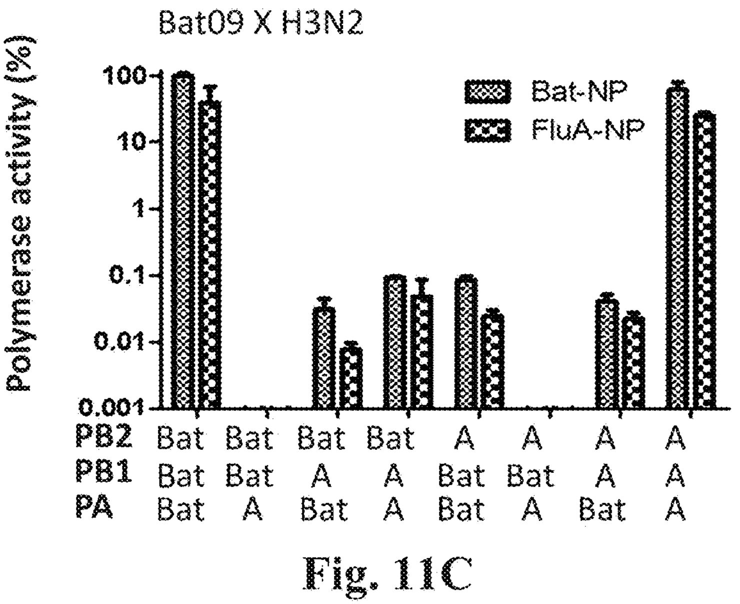
Figure 11D:
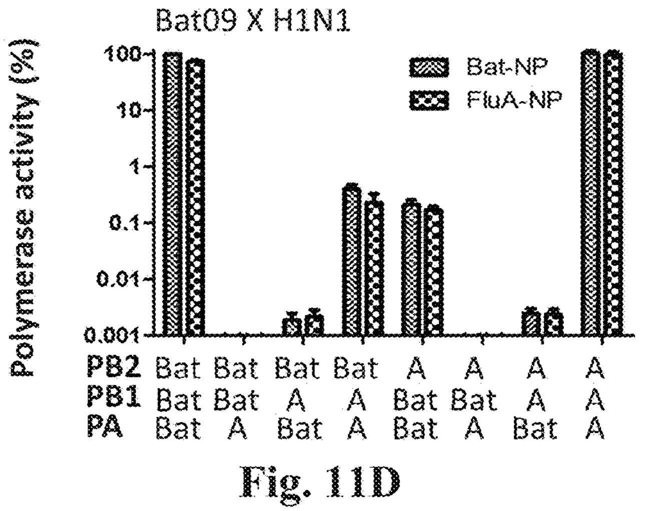
Figure 11E:
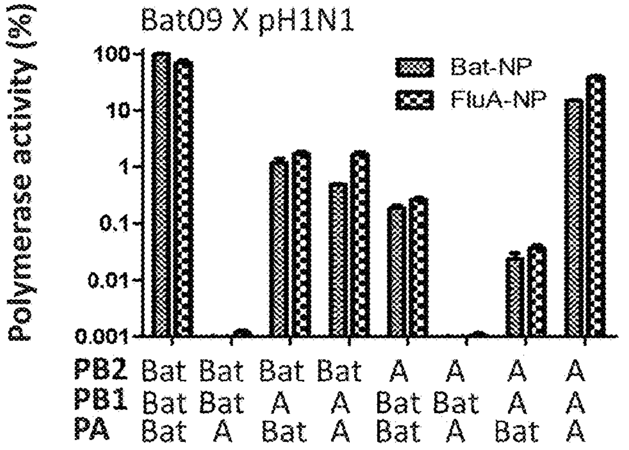
Figure 11F:
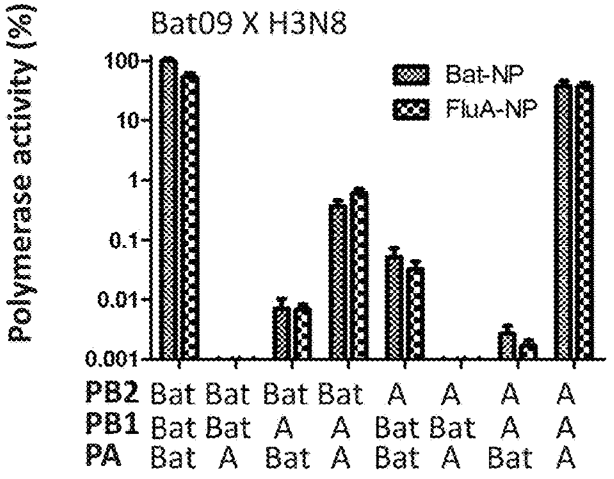
Figure 11G:
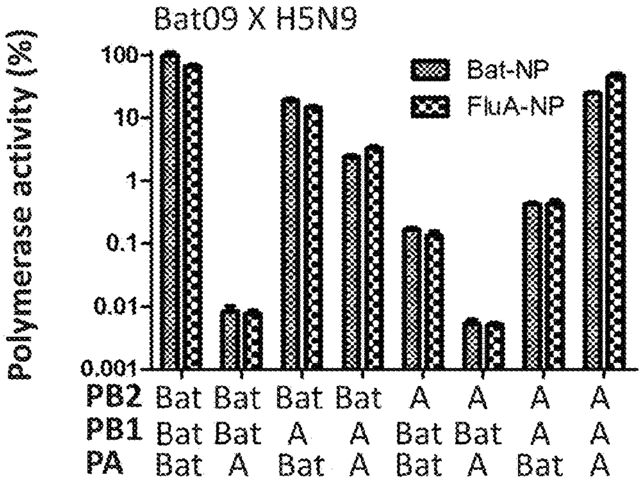
Figure 11H:
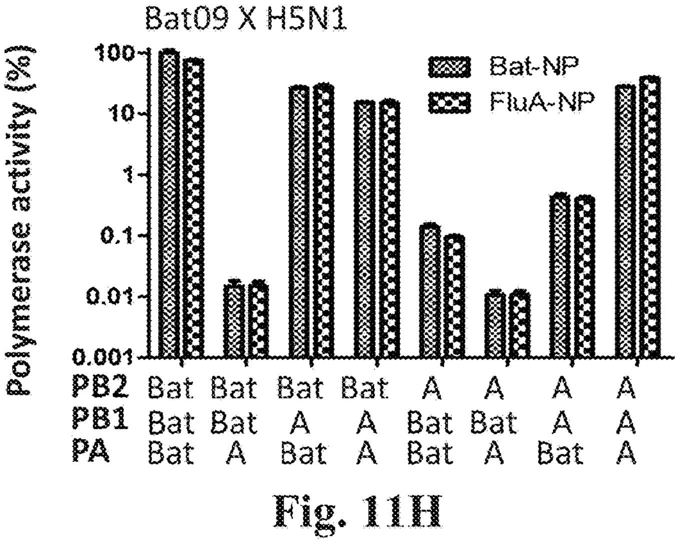
Figure 11I:
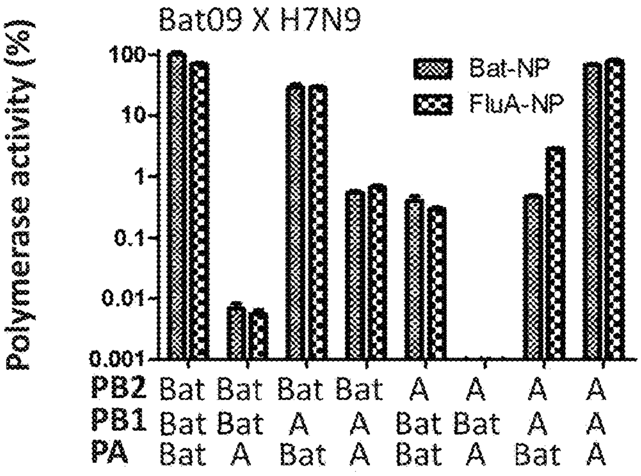
Figure 11J:
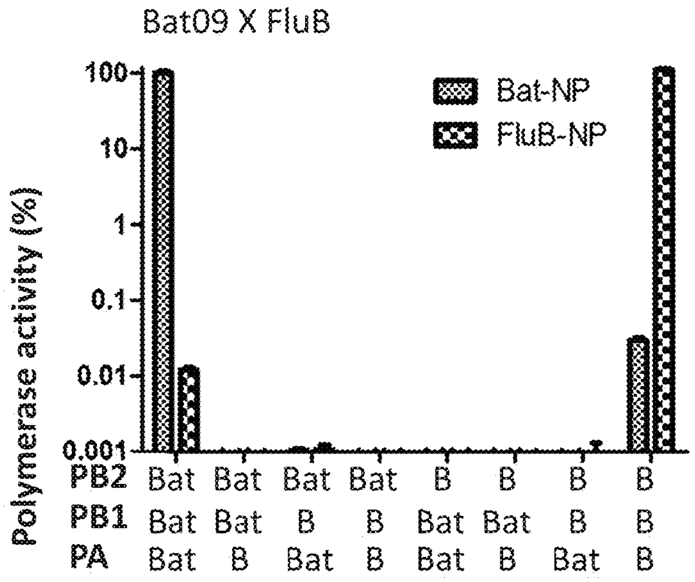

5. Internal Protein-Coding vRATAs of Bat-Influenza don't Efficiently Reassort with IAV or IBV Reassortment of IAVs is important in the evolution of IAVs and generation of panzootic and pandemic strains. Furthermore, efficient replication of bat-influenza internal protein vRNAs in human cells and mice, as well as their pathogenicity, necessitated an assessment of reassortment potential between Bat09 and other influenza viruses. Replication of vRNAs from different parental viruses is a factor critical in the generation of reassortant progeny. Transcription/replication of mini-genome reporter constructs showed that the viral RNA dependent RNA polymerase (RdRp), which is a heterotrimer of PB1, PB32, and PA, from bat-influenza, IAVs, and IBVs generally recognize and transcribe their cognate vRNAs more efficiently than non-cognate vRNAs (FIG. 10). Intriguingly, the Bat09 polymerase replicated the IBV reporter very efficiently (FIG. 10). Additionally, most RdRp combinations (PB2, PB1, PA) between bat-influenza and IAVs nearly abolished the polymerase activity in this very sensitive mini-genome reporter assay (FIG. 11A-I). The vRNA reporters used for the compatibility test between Bat09 and IAVs (FIG. 11A-I) were an equal ratio of pPolI-Bat-NS-Luc and pPolI-FluA-NS-Luc (FIG. 3E for gene diagrams). For compatibility test between Bat09 and IBV (FIG. 11J) the vRNA reporters used were pPolI-Bat-NS-Luc and pPolI-FluB-NS-Luc (FIG. 3E for gene diagrams). For compatibility test between Bat09 and Bat10 (FIG. 11K) only the pPolI-Bat-NS-Luc plasmid was used. Interestingly, the NP protein, which is a single-strand RNA-binding nucleoprotein, is completely compatible between Bat09 and IAVs (FIG. 11A-I), but it is incompatible between the bat-influenza and IBV (FIG. 11J).

Although some gene segment combinations showed limited polymerase activity in the mini-genome assays, we couldn't generate any reassortant viruses using reverse genetics between Bat09:mH1mN1 and PR8 that contain partly compatible RdRp components (e.g., Bat-PB2/PR8-PB1/PR8-PA), including the highly compatible NP vRNA/protein (Table 1 and Table 2).

TABLE 1

Rescue efficiency of PB2, PB1, PA reassortants between Bat09:mH1mN1 and PR8.

| | PB2 | PB1 | PA | NP, M, NS | HA, NA | Rescue* |
|---|---|---|---|---|---|---|
| 1 | Bat | Bat | Bat | Bat | mB1, mN1 | ++++ |
| 2 | PR8 | Bat | Bat | Bat | mH1, mN1 | Neg |
| 3 | Bat | PR8 | Bat | Bat | mH1, mN1 | Neg |
| 4 | Bat | Bat | PR8 | Bat | mH1, mN1 | Neg |
| 5 | PR8 | PR8 | Bat | Bat | mH1, mN1 | Neg |
| 6 | PR8 | Bat | PR8 | Bat | mH1, mN1 | Neg |
| 7 | Bat | PR8 | PR8 | Bat | mH1, mN1 | Neg |
| 8 | PR8 | PR8 | PR8 | Bat | mH1, mN1 | Neg |
| 9 | Bat | Bat | Bat | PR8 | PR8 | Neg |
| 10 | PR8 | Bat | Bat | PR8 | PR8 | Neg |
| 11 | Bat | PR8 | Bat | PR8 | PR8 | Neg |
| 12 | Bat | Bat | PR8 | PR8 | PR8 | Neg |
| 13 | PR8 | PR8 | Bat | PR8 | PR8 | Neg |
| 14 | PR8 | Bat | PR8 | PR8 | PR8 | Neg |
| 15 | Bat | PR8 | PR8 | PR8 | PR8 | Neg |
| 16 | PR8 | PR8 | PR8 | PR8 | PR8 | ++++ |

*Rescue efficiency definition.

Very easy (++++); P0 viral titer $10^6$-$10^8$ $TCID_{50}$/ml, or severe CPE observed in P1 within 1 dpi;

Moderate (+++): P0 titer $10^4$-$10^6$ $TCID_{50}$/ml, or obvious CPE observed in P1 within 2 dpi;

Difficult (++): P0 liter $10^2$-$10^4$ $TCID_{50}$/ml, or weak. CPE observed in P1 within 4 dpi;

Very difficult (+): P0 liter lower than $10^2$ $TCID_{50}$/ml, or CPE not observed until P2/P3;

Negative (Neg): rescue failed, no CPE observed through passage 3.

For each combination, the rescue was repeated at least 3 times.

TABLE 2

Rescue efficiency of internal gene reassortants between Bat09:mH1mN1 and PR8.

| | Pols* | NP | M | NS | HA, NA | Rescue** |
|---|---|---|---|---|---|---|
| 1 | Bat | Bat | Bat | Bat | mH1, mN1 | ++++ |
| 2 | Bat | Bat | Bat | PR8 | mH1, mN1 | Neg |
| 3 | Bat | Bat | PR8 | Bat | mH1, mN1 | +++ |
| 4 | Bat | Bat | PR8 | PR8 | mH1, mN1 | Neg |
| 5 | Bat | PR8 | Bat | Bat | mH1, mN1 | Neg |
| 6 | Bat | PR8 | Bat | PR8 | mH1, mN1 | Neg |
| 7 | Bat | PR8 | PR8 | Bat | mH1, mN1 | Neg |
| 8 | Bat | PR8 | PR8 | PR8 | mH1, mN1 | Neg |
| 9 | PR8 | Bat | Bat | Bat | mH1, mN1 | Neg |
| 10 | PR8 | Bat | Bat | PR8 | mH1, mN1 | Neg |
| 11 | PR8 | Bat | PR8 | Bat | mH1, mN1 | Neg |
| 12 | PR8 | Bat | PR8 | PR8 | mH1, mN1 | Neg |
| 13 | PR8 | PR8 | Bat | Bat | mH1, mN1 | Neg |
| 14 | PR8 | PR8 | Bat | PR8 | mH1, mN1 | Neg |
| 15 | PR8 | PR8 | PR8 | Bat | mH1, mN1 | Neg |
| 16 | PR8 | PR8 | PR8 | PR8 | mH1, mN1 | Neg |
| 17 | Bat | Bat | Bat | Bat | PR8 | Neg |
| 18 | Bat | Bat | Bat | PR8 | PR8 | Neg |
| 19 | Bat | Bat | PR8 | Bat | PR8 | Neg |
| 20 | Bat | Bat | PR8 | PR8 | PR8 | Neg |
| 21 | Bat | PR8 | Bat | Bat | PR8 | Neg |
| 22 | Bat | PR8 | Bat | PR8 | PR8 | Neg |
| 23 | Bat | PR8 | PR8 | Bat | PR8 | Neg |
| 24 | Bat | PR8 | PR8 | PR8 | PR8 | Neg |
| 25 | PR8 | Bat | Bat | Bat | PR8 | Neg |
| 26 | PR8 | Bat | Bat | PR8 | PR8 | Neg |
| 27 | PR8 | Bat | PR8 | Bat | PR8 | Neg |
| 28 | PR8 | Bat | PR8 | PR8 | PR8 | Neg |
| 29 | PR8 | PR8 | Bat | Bat | PR8 | Neg |
| 30 | PR8 | PR8 | Bat | PR8 | PR8 | Neg |
| 31 | PR8 | PR8 | PR8 | Bat | PR8 | Neg |
| 32 | PR8 | PR8 | PR8 | PR8 | PR8 | ++++ |

*Pols = Co-transfection of PB1, PB2, and PA reverse genetics plasmids.

**Rescue efficiency defined in Table 1. For each combination, the rescue was repeated at least 3 times.

Instead, the PR8-M segment could unidirectionally substitute for the Bat09-M segment (Table 2). This likely results from the highly conserved nature of the M vRNA and proteins (M1, M2). Swapping the putative cis-acting packaging signals of the Bat-NP and known packaging signals of the PR8-NP, or between the Bat-NS and PR8-NS didn't enable rescue of viruses containing either the NP or NS vRNAs in a heterologous virus background (Table 3 and see FIG. 3D for diagrams).

TABLE 3

Rescue efficiency of reassortants with NP and NS containing modified packaging signals.

| | PB2 | PB1 | PA | NP | M | NS | HA, NA | Rescue* |
|---|---|---|---|---|---|---|---|---|
| 1 | Bat | Bat | Bat | Bat | Bat | Bat | mH1, mN1 | ++++ |
| 2 | Bat | Bat | Bat | Batps-PR8-NP | Bat | Bat | mH1, mN1 | Neg |
| 3 | Bat | Bat | Bat | Bat | Bat | Batps-PR8-NS | mH1, mN1 | Neg |
| 4 | Bat | Bat | Bat | Batps-PR8-NP | Bat | Batps-PR8-NS | mH1, mN1 | Neg |
| 5 | Bat | Bat | Bat | PR8ps-Bat-NP | Bat | Bat | mH1, mN1 | Neg |
| 6 | Bat | Bat | Bat | Bat | Bat | PR8ps-Bat-NS | mH1, mN1 | + |
| 7 | PR8 | PR8 | PR8 | PR8ps-Bat-NP | PR8 | PR8 | PR8 | Neg |
| 8 | PR8 | PR8 | PR8 | PR8 | PR8 | PR8ps-Bat-NS | PR8 | Neg |
| 9 | PR8 | PR8 | PR8 | PR8ps-Bat-NP | PR8 | PR8ps-Bat-NS | PR8 | Neg |
| 10 | PR8 | PR8 | PR8 | Batps-PR8-NP | PR8 | PR8 | PR8 | Neg |
| 11 | PR8 | PR8 | PR8 | PR8 | PR8 | Batps-PR8-NS | PR8 | +++ |
| 12 | PR8 | PR8 | PR8 | PR8 | PR8 | PR8 | PR8 | ++++ |

*Rescue efficiency defined in Table 1.

For each combination, the rescue was repeated at least 3 times.

6. Interrogation of Reassortment Between IAV and Modified Bat09 Using a Classical Co-Infection Approach While the generation of reassortants through plasmid-based reverse genetics is a powerful and sensitive way to rescue influenza viruses, it's difficult to generate every possible gene constellation and accompanying minor nucleotide variations that could give rise to progeny reassortants during co-infection. Therefore, we attempted to generate reassortants between a modified Bat09 virus and PR8 using a classical co-infection approach. However, when MDCK cells were inoculated at a high multiplicity of infection (MDI) with both PR8 and Bat09:mH1mN1 viruses, reassortment between the two parental viruses was not detected. We plaque purified 118 progeny viruses from the co-infection and 53 of them were the parental PR8 virus and 65 of them were the parental Bat09:mH1mN1 virus. Although more exhaustive classical reassortant studies are needed to completely evaluate the generation of natural reassortants between these viruses, the data indicate that PR8 and Bat09:mH1mN1 don't efficiently reassort.

7. Divergent Bat-Influenza Viruses are Highly Compatible for Reassortment

Figure 11K:
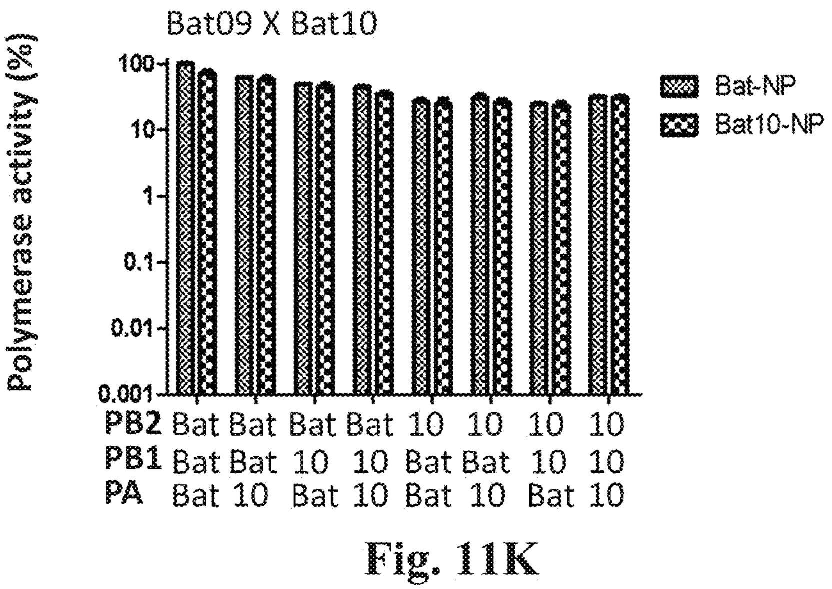

Recently, another bat-influenza virus A/flat-faced bat/Peru/033/2010 (H18N11) (Bat10) was identified in Peru and phylogenetic analysis indicated this virus diverged from the bat-influenza viruses identified in Guatemala (e.g., Bat09) so long ago that genetic diversity between these two bat-influenza viruses is higher than that of IAVs. Reassortment of the PB2, PB1, PA, and NP segments in mini-genome polymerase activity assay demonstrated that the Bat09 and Bat10 viruses were fully compatible (FIG. 11K). Most importantly, successful reassortment between the two modified bat viruses (Bat09:mH1mN1ss and Bat10:mH1mN1ss) (Table 4 and FIG. 3 for diagrams of constructs) proved that these genetically divergent bat-influenza virus vRNAs were highly interchangeable, in contrast to their very low compatibility with IAV and IBV.

TABLE 4

Rescue efficiency of reassortants between Bat09:mH1mN1ss and Bat10:mH1mH1ss.

| | PB2 | PB1 | PA | NP | M | NS | HA | NA | Rescue* |
|---|---|---|---|---|---|---|---|---|---|
| 1 | Bat09 | Bat09 | Bat09 | Bat09 | Bat09 | Bat09 | H17ps-H1ss | N10ps-N1ss | ++++ |
| 2 | Bat10 | Bat09 | Bat09 | Bat09 | Bat09 | Bat09 | H17ps-H1ss | N10ps-N1ss | +++ |
| 3 | Bat09 | Bat10 | Bat09 | Bat09 | Bat09 | Bat09 | H17ps-H1ss | N10ps-N1ss | ++ |
| 4 | Bat09 | Bat09 | Bat10 | Bat09 | Bat09 | Bat09 | H17ps-H1ss | N10ps-N1ss | + |
| 5 | Bat09 | Bat09 | Bat09 | Bat10 | Bat09 | Bat09 | H17ps-H1ss | N10ps-N1ss | +++ |
| 6 | Bat09 | Bat09 | Bat09 | Bat09 | Bat10 | Bat09 | H17ps-H1ss | N10ps-N1ss | ++++ |
| 7 | Bat09 | Bat09 | Bat09 | Bat09 | Bat09 | Bat10 | H17ps-H1ss | N10ps-N1ss | ++++ |
| 8 | Bat09 | Bat09 | Bat09 | Bat09 | Bat09 | Bat09 | H18ps-H1ss | N10ps-N1ss | ++++ |
| 9 | Bat09 | Bat09 | Bat09 | Bat09 | Bat09 | Bat09 | H17ps-H1ss | N11ps-N1ss | ++++ |
| 10 | Bat09 | Bat09 | Bat09 | Bat09 | Bat09 | Bat09 | H18ps-H1ss | N11ps-N1ss | +++ |
| 11 | Bat10 | Bat10 | Bat10 | Bat10 | Bat10 | Bat10 | H18ps-H1ss | N11ps-N1ss | ++++ |
| 12 | Bat09 | Bat10 | Bat10 | Bat10 | Bat10 | Bat10 | H18ps-H1ss | N11ps-N1ss | + |
| 13 | Bat10 | Bat09 | Bat10 | Bat10 | Bat10 | Bat10 | H18ps-H1ss | N11ps-N1ss | +++ |
| 14 | Bat10 | Bat10 | Bat09 | Bat10 | Bat10 | Bat10 | H18ps-H1ss | N11ps-N1ss | ++ |
| 15 | Bat10 | Bat10 | Bat10 | Bat09 | Bat10 | Bat10 | H18ps-H1ss | N11ps-N1ss | +++ |
| 16 | Bat10 | Bat10 | Bat10 | Bat10 | Bat09 | Bat10 | H18ps-H1ss | N11ps-N1ss | +++ |
| 17 | Bat10 | Bat10 | Bat10 | Bat10 | Bat10 | Bat09 | H18ps-H1ss | N11ps-N1ss | ++++ |
| 18 | Bat10 | Bat10 | Bat10 | Bat10 | Bat10 | Bat10 | H17ps-H1ss | N11ps-N1ss | +++ |
| 19 | Bat10 | Bat10 | Bat10 | Bat10 | Bat10 | Bat10 | H18ps-H1ss | N10ps-N1ss | +++ |
| 20 | Bat10 | Bat10 | Bat10 | Bat10 | Bat10 | Bat10 | H17ps-H1ss | N10ps-N1ss | +++ |

*Rescue efficiency definition described in Table 1.

Interestingly, classical co-infection of the Bat09:mH1mN1 and Bat110:mH1mN1 viruses in MDCK cells readily generated reassortant progeny viruses with various genotypes, and some were apparently preferentially selected (e.g., Bat10:Bat09-NS reassortant, Table 5), demonstrating the merit of classic co-infection strategy in identification of gene constellations that may have certain advantages.

TABLE 5

Co-infection results for reassortment between Bat09:mH1mN1 and Bat10:mH1mN1.

| | PB2 | PB1 | PA | NP | M | NS | HA | NA | No. of Plaques* |
|---|---|---|---|---|---|---|---|---|---|
| 1 | Bat09 | Bat09 | Bat09 | Bat09 | Bat09 | Bat09 | H17ps-H1 | N10ps-N1 | 39 |
| 2 | Bat10 | Bat09 | Bat10 | Bat09 | Bat10 | Bat09 | H17ps-H1 | N10ps-N1 | 1 |
| 3 | Bat10 | Bat09 | Bat10 | Bat09 | Bat10 | Bat10 | H18ps-H1 | N10ps-N1 | 1 |
| 4 | Bat10 | Bat10 | Bat10 | Bat09 | Bat10 | Bat10 | H17ps-H1 | N10ps-N1 | 2 |
| 5 | Bat10 | Bat10 | Bat10 | Bat10 | Bat09 | Bat09 | H18ps-H1 | N10ps-N1 | 1 |
| 6 | Bat09 | Bat10 | Bat10 | Bat10 | Bat10 | Bat09 | H17ps-H1 | N10ps-N1 | 1 |
| 7 | Bat10 | Bat10 | Bat10 | Bat10 | Bat10 | Bat10 | H17ps-H1 | N10ps-N1 | 1 |
| 8 | Bat10 | Bat10 | Bat10 | Bat10 | Bat10 | Bat10 | H18ps-H1 | N10ps-N1 | 1 |

TABLE 5-continued

Co-infection results for reassortment between Bat09:mH1mN1 and Bat10:mH1mN1.

| | PB2 | PB1 | PA | NP | M | NS | HA | NA | No. of Plaques* |
|---|---|---|---|---|---|---|---|---|---|
| 9 | Bat10 | Bat10 | Bat10 | Bat10 | Bat10 | Bat10 | H17ps-H1 | N11ps-N1 | 1 |
| 10 | Bat10 | Bat10 | Bat10 | Bat09 | Bat10 | Bat10 | H18ps-H1 | N11ps-N1 | 2 |
| 11 | Bat10 | Bat10 | Bat10 | Bat10 | Bat10 | Bat09 | H18ps-H1 | N11ps-N1 | 13 |
| 12 | Bat10 | Bat10 | Bat10 | Bat10 | Bat10 | Bat10 | H18ps-H1 | N11ps-N1 | 45 |

*Totally 108 plaques were purified for genotyping

Collectively the mini-genome replication, reverse genetics reassortment, and co-infection reassortment experiments strongly suggest that two divergent bat-influenza viruses readily reassort with each other, whereas they won't reassort with canonical IAVs in the natural setting.

Materials and Methods

1. Biosafety and Ethics Statement

The study was reviewed and approved by the institutional Biosafety Committee at Kansas State University (protocol #903), and by the institutional biosafety committee at the J. Craig Venter Institute (protocol #3414). We conducted the initial studies using PR8 gene fragments to generate the modified bat-influenza viruses and to test the reassortment potential because PR8 is a widely used lab/mouse adapted BSL2 virus that poses very low risk to humans or livestock. Subsequently, TX98 H3N2 genes were used in a few experiments because this is a BSL2 swine virus, which we have used previously and the viruses generated were considered low risk.

The animal studies were performed in strict accordance with the recommendations in the Guide for the Care and Use of Laboratory Animals of the National Institutes of Health. The animal protocol (protocol #3339) was reviewed and approved by the Institutional Animal Care and Use Committee at Kansas State University. All animal studies were performed in a Biosafety Level 3 facility located at the Biosecurity Research Institute at Kansas State University under the approved protocol #3339 following the American Veterinary Medicine Association guidelines on euthanasia. For virus inoculation, each mouse was anesthetized by inhaling 4% isoflurane. Mice were euthanized if more than 25% of weight was lost after virus inoculation. Euthanasia of mice was conducted by inhaling 4% isoflurane followed by cardiac puncture and cervical dislocation. No survival surgery was performed, and all efforts were made to minimize suffering.

2. Cells

Human embryonic kidney 293T (HEK-293T) cells, mouse rectum epithelial carcinoma (CMT-93) cells, and African green monkey kidney (Vero) cells were maintained in Dulbecco's modified Eagle's medium (DMEM) supplemented with 10% fetal bovine serum (FBS). Madin-Darby canine kidney (MDCK) cells were maintained in minimum essential medium (MEM) supplemented with 5% FBS. Human lung epithelial (A549) cells, bat lung epithelial (Tb1Lu) cells, mink lung epithelial (Mv1Lu) cells and swine testis (ST) cells were maintained in MEM supplemented with 10% FBS. Human lung epithelial (Calu-3) cells were maintained in MEM supplemented with 10% FBS, 1% nonessential amino acids, and 1 mM sodium pyruvate.

3. Complete Genome Synthesis and Plasmid Construction

Figure 12A:
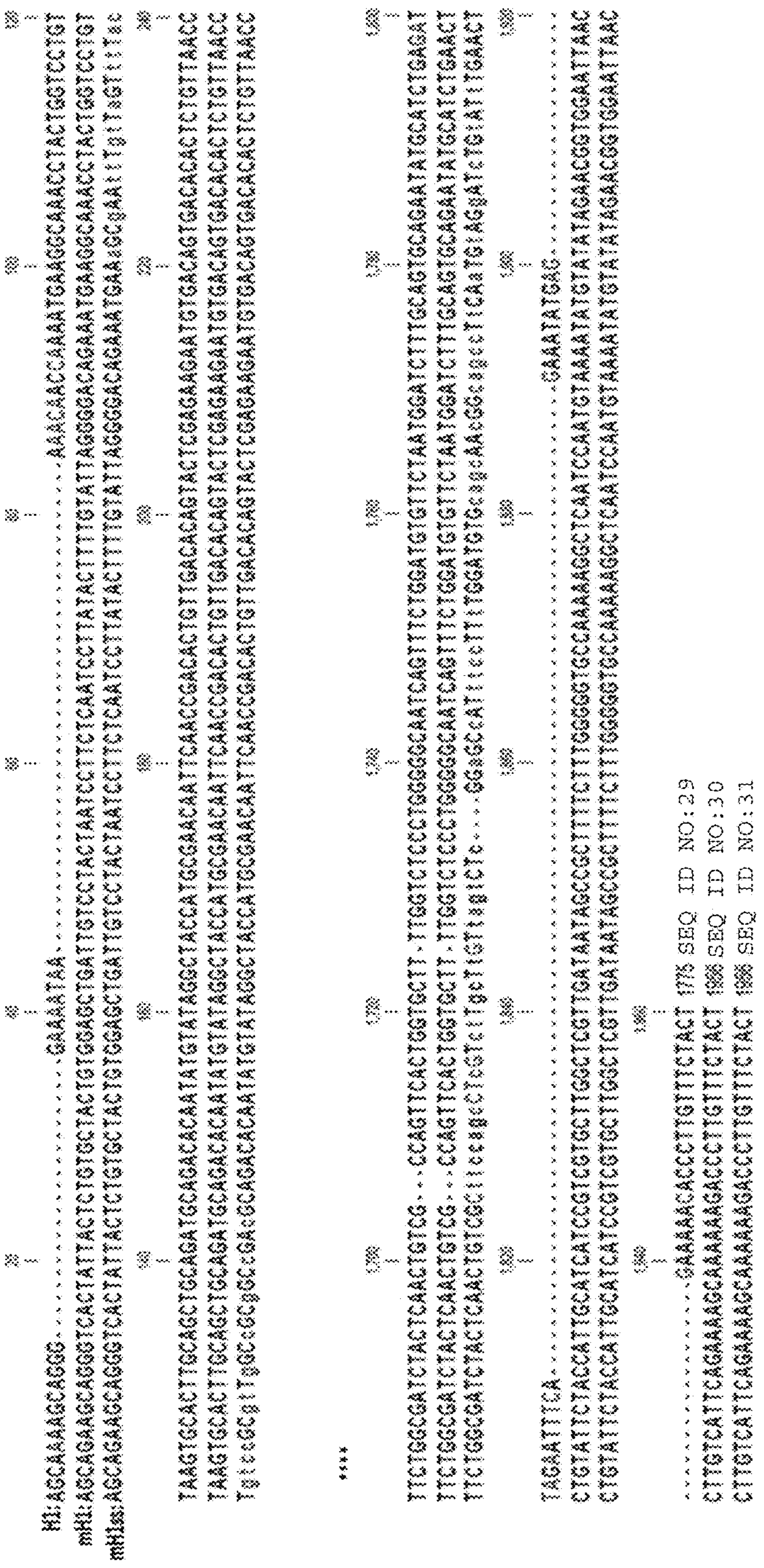
Figure 12B:
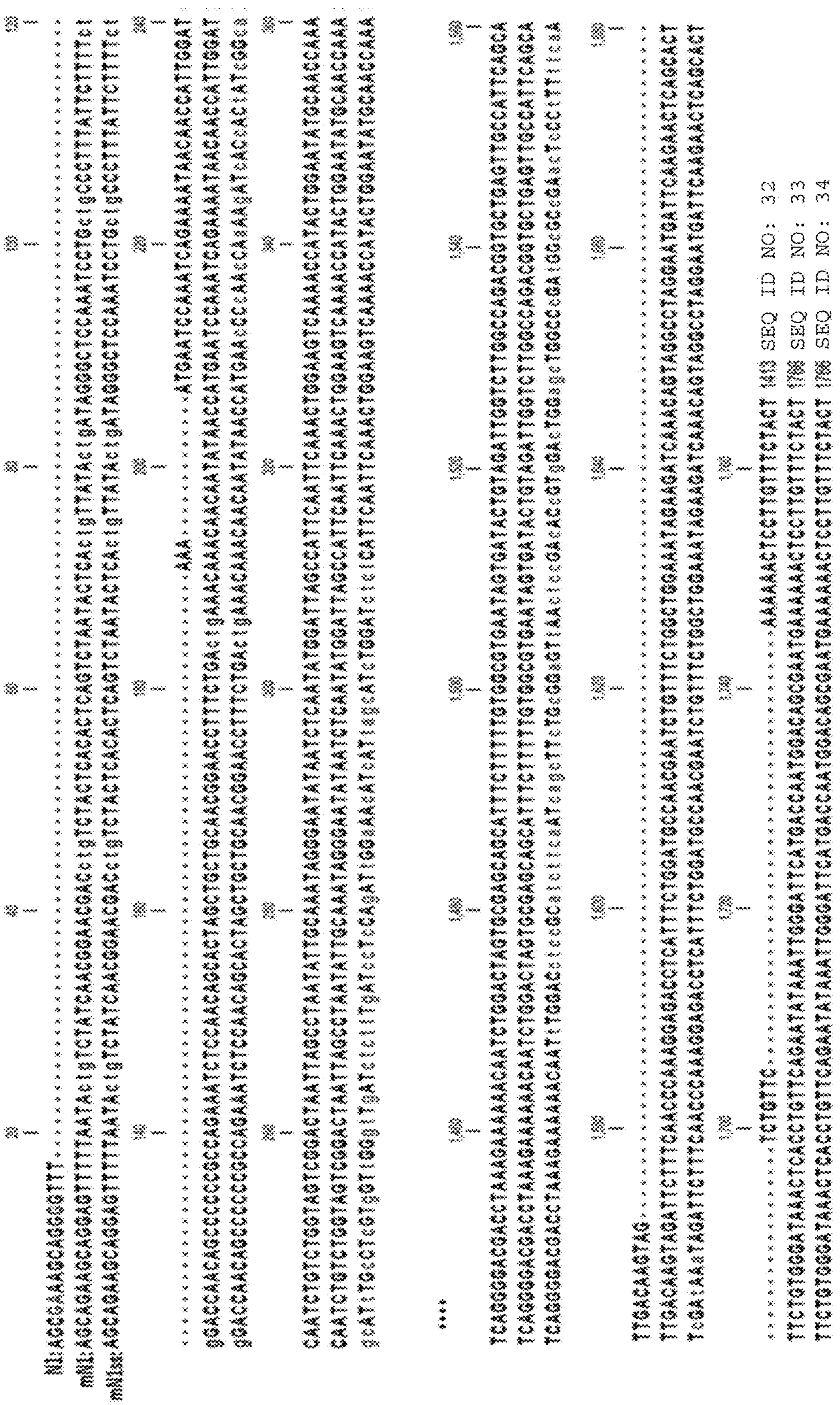

Nucleotide sequences of the eight gene segments of A/little yellow-shouldered bat/Guatemala/164/2009 (H17N10) (Bat09) were retrieved from the GenBank database. A total of 472 oligonucleotides of 56-60 bases in length were designed for enzymatic assembly of the eight segments. The assembly and error correction processes were performed as described in Dormitzer P R, et al. (Synthetic generation of influenza vaccine viruses for rapid response to pandemics. Sci Transl Med 5: 185ra168(2013)); and Liu Q, et al. (Analysis of Recombinant H7N9 Wild-Type and Mutant Viruses in Pigs Shows that the Q226L Mutation in HA is Important for Transmission. J Virol 88: 8153-8165 (2014)), except that the protocol was modified with increased time at all extension steps (from 72° C. for 1 min to 72° C. for 2 min) for efficient assembly of the polymerase segments. The synthesized segments (FIG. 1) were cloned into the modified bidirectional influenza reverse genetics vectors pBZ66A12 using the recombination-based method and transformed into Stella competent *E. coli* cells (Clontech). Colonies were selected and sequenced. The appropriate clones for each segment were propagated for plasmid preparation and verified by sequencing. The resulting plasmids are paZ146A1 (PB2), pBZ147A11 (PB1), pBZ148A20 (PA), pBZ149A30 (HA), pBZ150A31 (NP), pBZ151A36 (NA), pBZ152A42 (M) and pB1153A45 (NS). The whole process only took seven days to complete. The plasmids containing Bat09 PB2 mutations were constructed by site-directed mutagenesis using the pBZ1.46A1 as template. The NS1 truncation constructs were generated by Gibson assembly and details of the truncations are diagramed in FIG. 3C. The modified (m) Bat09 HA and NA (mH1, mN1, mH1ss, and mN1ss, see FIGS. 3A, 3B for diagrams, and FIGS. 12A-12B for sequence alignment) were synthetized by Gibson assembly from oligonucleotides. To construct the MH1 (SEQ ID NO:30), PR8-HA coding region (SEQ ID NO:29) was flanked by the putative packaging regions from Bat09-HA and all ATG in the Bat09-HA 5' packaging region were mutated. To construct the mN1 (SEQ ID NO:33), PR8-NA coding region (SEQ ID NO: 32) was flanked by the putative packaging regions from Bat09-NA and all ATG in the Bat09-NA 5' packaging region were mutated. As shown in FIG. 3B, mH1ss (SEQ ID NO:31) was constructed by introducing 64 of silent substitutions into the coding region of mH1 to disrupt the remaining packaging signals in the PR8-HA coding region. mN1ss (SEQ ID NO:34) was constructed by introducing 90 of silent substitutions into the coding region of mN1 to disrupt the remaining packaging signals in the PR8-NA coding region. The mH1ss was referred as H17ps-H1ss and the mN1ss was referred as N10ps-N1ss in Table 4. The H18ps-H1ss and N11ps-N1ss have the HA and NA packaging regions from Bat10. FIG. 3C shows the wild type NS gene and the NS1 truncated NS gene from Bat09. NS1 truncated PR8-NS genes were constructed similarly. For Bat09, NP and NS coding regions were flanked by putative cis-acting packaging regions from PR8 NP and NS. PR8 NP and NS coding regions flanked by putative cis-acting packaging regions from Bat NP and NS.

Silent substitutions (ss) were introduced to disrupt the putative packaging signals in the PR8 HA and NA terminal coding regions. The mH1ss and mN1ss are thus more appropriate than the mH1 and mN1 to assess the HA and NA packaging signal compatibility between Bat09 and PR8. The Batps-PR8-NP, PR8ps-Bat-NP, Batps-PR8-NS, and PR8ps-Bat-NP constructs were constructed similarly and diagramed in FIG. 3D. As a comparison of the speed of different synthesis strategies, the eight gene segments of A/flat-faced bat/Peru/033/2010 (H18N11) (Bat10) were synthesized by Genewiz (NJ, USA) in the vector plasmid of pUC57 based on the GenBank database and subcloned into pHW2000 vector. The resulting plasmids (pHW-H18-PB2, pHW-H18-PB1, pHW-H18-PA, pHW-H18-HA, pHW-H18-NP, pHW-H18-NA, pHW-H18-M and pHW-H18-NS) were confirmed by sequencing. The whole process took more than one month. The PB2, PB1, PA and NP genes were also subcloned into the pDZ vector for use in the mini-genome assay. Diagrams of the mutant or modified genes of Bat09 and Bat10 are described in FIG. 3. The pPol1-NS-Luc reporters used in the mini-genome polymerase activity assay were described in FIG. 3E. Sequences of the constructs used in this study were confirmed to ensure absence of unwanted mutations and the GenBank accession numbers are KM203345-KM203356.

4. Virus Rescue

Briefly, 0.6 μg of plasmid for each gene segment was mixed and incubated with 15 μl of Mirus TranIT-LT1 (Mirus Bio, Madison, Wis.) at 20° C. for 20 min. The transfection mixture was transferred to 90% confluent 293T/MDCK cell monolayers in a 35-mm tissue culture dish and incubated at 37° C. with 5% $CO_2$ for 8 h. The transfection supernatant was replaced with 3 ml of Opti-Mem I medium (Life Technologies) supplemented with 0.3% bovine serum albumin (BSA) fraction V (Life Technologies), 3 μg/ml tosylsulfonyl phenylalanyl chloromethyl ketone (TPCK)-trypsin (Worthington, Lakewood, N.J.), and 1% antibiotic-antimycotic (Life Technologies). Three days post-transfection, culture supernatant (passage 0, P0) was collected and 0.5 ml of that was inoculated into MDCK cells in 6-well plates at 37° C. Supernatant (P1) was collected at 4 days post-inoculation (dpi), or when severe cytopathic effect (CPE) was observed. The P1 supernatant was further passaged blindly for two passage before determined to be negative for rescue. Titers of the viruses used in this study were determined by $TCID_{50}$ assay in MDCK cells.

Rescue efficiency definition. Very easy (++++): P0 viral titer $10^6$-$10^8$ $TCID_{50}$/ml, or severe CPE observed in P1 within 1 dpi; Moderate (+++): P0 titer $10^4$-$10^6$ $TCID_{50}$/ml, or obvious CPE observed in P1 within 2 dpi; Difficult (++): P0 titer $10^2$-$10^4$ $TCID_{50}$/ml, or weak CPE observed in P1 within 4 dpi; Very difficult (+): P0 titer lower than $10^2$ $TCID_{50}$/ml, or CPE not observed until P2/P3; Negative (Neg): rescue failed, no CPE observed through passage 3.

Various transfection conditions including different transfection reagents, temperatures, and incubation time before supernatant collection were attempted to rescue the wild type Bat09 virus and the reassortants between Bat09 and PR8. However, none of them generated any positive rescue results if they were negative under standard rescue condition described above. Bat09 transfection supernatants were also transferred to various cells (MDCK, mink lung Mv1-Lu, swine testis, Vero, A549 cells, Calu-3, bat lung epithelial Tb1Lu) and embryonated chicken eggs and passaged at least three times. The real-time RT-PCR assays targeting Bat09 and PR8 M genes were used to confirm negative results (primers and probes are possible upon request).

5. Electron Microscopy

To determine whether virus particles of Bat09 and other viruses can be produced by reverse genetics system, a total of thirty-five ml of transfected 293T cell supernatants for each virus were collected at 48 hours post transfection and centrifuged at 8,000 rpm for 20 minutes to remove the cell debris. Then the clear supernatant was loaded on 30% (w/v) sucrose in centrifuge tubes and was concentrated at 27,000 rpm (Optima LE-80K ultracentrifuge, Beckman Coulter) for 2 hours. The virus pellets was dissolved in 100 μl of water and the viral particles were fixed by incubating with 0.2% paraformaldehyde at 37° C. for 48 hours. The fixed particles were dipped on a 200 mesh copper grid and the grid was dried and stained with negative staining before observation under an electron microscope.

5. Virus Replication In Vitro and In Ovo

MDCK monolayers in 12-well plates were washed twice with PBS, and then 2 ml of virus growth medium (VGM) was added to each well. The cells were inoculated at a multiplicity of infection (MOI) of 0.01 $TCID_{50}$/cell with the Bat09:mH1mN1 virus or PR8 virus (Bat09:mH3mN2 virus or TX98 virus) and incubated at 37° C. Supernatants were collected at 1, 2, and 3 days post inoculation (dpi). Inoculations of Calu-3 cells were performed similarly, except that an MOI of 0.02 $TCID_{50}$/cell was used for the following viruses: Bat09:mH1mN1ss, Bat09:mH1mN1ss-NS1-73, Bat09:mH1mN1ss-NS1-128, PR8, PR8-NS1-73, and PR8-NS1-126. The VGM used for MDCK cells was EMEM supplemented with 0.15% BSA fraction V, 2 μg/ml TPCK-trypsin, and 1% antibiotic-antimycotic, and the VGM used for Calu-3 cells was EMEM supplemented with 0.3% BSA fraction V, 1 μg/ml TPCK-trypsin, and 1% antibiotic-antimycotic. All virus titers were determined by $TCID_{50}$ assay using MDCK cells.

Six of 10-day-old embryonated chicken eggs were inoculated with Bat09:mH1mN1 or PR8 at $10^3$ $TCID_{50}$/egg. After 2 days incubation at 35° C., allantoic fluid was collected from each egg and titrated individually. The 4 eggs with the highest titers in each virus group was used to calculate the average titer and generate the graph in FIG. 2E.

6. Next Generation Sequencing and Analysis

A modified Multi-segment RT-PCR was used to amplify influenza-specific segments. The only modification to the procedure was the primers used for amplification were changed to match bat influenza termini. The oligonucleotide primers used were Uni12/Inf-5G (SEQ ID NO:35) and Uni13/Inf-1 (SEQ ID NO:36). The M-RTPCR amplicons were used for Illumina Miseq library construction via Nextera DNA sample prep kit (Illumina, Inc.) and sequenced using the Illumina MiSeq (Illumina, Inc.) according to manufacturer's instructions. SNP variations were identified using custom software that applies statistical tests to minimize false positive SNP calls that could be caused by the types of sequence-specific errors that may occur in Illumina reads identified and described in Nakamura, et al. (Sequence-specific error profile of Illumina sequencers. Nucleic Acids Res 39: e90(2011)). To overcome this problem, the protocol requires observing the same SNP, at a statistically significant level, in both sequencing directions. Once a minimum minor allele frequency threshold and significance level are established by the user, the number of minor allele observations and major allele observations in each direction and the minimum minor allele frequency threshold are used to calculate a p-value based on the binomial distribution cumulative probability, and if the p-values calculated in each of the two sequencing directions are both less than the Bonferroni-corrected significance level, then the SNP call is accepted. For our analyses, we used a significance level of 0.05 (Bonferroni-corrected for tests in each direction to 0.025), and a minimum minor allele frequency threshold of 10% of the read population.

7. Interferon-β Reporter Assay

To measure the IFN-antagonist function of NS1, a luciferase-based, Sendai virus-mediated IFN-β promoter activation assay was conducted as previously described. Briefly, 293T cells in 24-well plates were transfected with empty vector (200 ng) or increasing amounts of wild type (WT) or carboxyl terminal truncated NS1 from Bat09 and PR8 (2 ng, 10 ng, and 50 ng of NS1 expression plasmids supplemented with 198 ng, 190 ng, and 150 ng of empty vector, respectively). Also co-transfected were 200 ng of an IFN-β-promoter-luciferase reporter plasmid (pIFNβ-Luc) and 20 ng of a plasmid constitutively expressing Renilla luciferase (pRL-TK from Promega). At 18 hours post transfection, cells were infected with Sendai-virus to induce the IFN-β promoter. A dual-luciferase assay was performed at 18 hour post virus inoculation, and firefly luciferase was nationalized to Renilla luciferase activity. The relative luciferase activity of the group with empty vector was set as 100%, and the other groups were presented relative to that.

8. Interferon Bioassay with VSV-Luciferase Virus

As previously described for the VSV-GFP virus mediated interferon bioassay, in the VSV-Luciferase virus mediated bioassay, A549 cells were inoculated with one of the wild type or NS1 truncated viruses at an MOI of 4 $TCID_{50}$/cell, or were mock-inoculated; supernatants were then collected at 24 hpi. Supernatants were treated with UV irradiation to inactivate viruses and were then transferred to naïve A549 cells. Following 24 h of incubation at 37° C., supernatants were removed, and the cells were inoculated with VSV-Luciferase virus, at an MOI of 2 $TCID_{50}$/cell. The firefly luciferase expression in the cells was measured using the Luciferase Assay System (Promega) at 4 hpi with VSV-Luciferase.

9. Mini-Genome Polymerase Activity Assay

The luciferase-mediated mini-genome polymerase activity assay was performed as previously described, using a PolI-driven reporter plasmid and pDZ-based PB2, PB1, PA, and NP bidirectional expression plasmids. To determine the effects of PB2 mutations on polymerase activity (FIG. 9) 293T cells were co-transfected with 0.2 μg each of the PB2 (WT or mutant), PB1, PA, NP, and a pPol1-FluA-NS-Luc (firefly luciferase flanked by A/New York/1682/2009). As a control for transfection efficiency, 0.02 μg of the Renilla lucifrase plasmid pRL-TK (Promega) was also co-transfected. After 18 hours of incubation at 33° C., 37° C., and 39° C., luciferase production was assayed using the dual-luciferase reporter assay system (Promega) according to the manufacturer's instructions. Firefly luciferase expression was normalized to Renilla luciferase expression (relative activity). The relative activity of the PB2-WT was set as 1 fold, and the relative activities of the PB2 mutants were presented relative to that (FIG. 9).

To test the compatibility between RNPs (PB2, PB1, PA, and NP) and viral RNA promoters from bat-influenza virus (Bat09) (FIG. 10), IAV (A/PR/8/1934), and IBV (B/Russia/1969), 293T cells were co-transfected with 0.2 μg each of the PB2, PB1, PA, NP, and a pPol1-NS-Luc reporter plasmid, followed by incubation at 37° C. for 18 hours. Three reporters were used in this study, including pPolI-Bat-NS-Luc (firefly luciferase flanked by Bat09 NS non-coding regions), pPol1-FluA-NS-Luc, and pPolI-FluB-NS-Luc (firefly luciferase flanked by B/Russia/1969 NS non-coding regions) (FIG. 3E). For each combination of RNP and pPolI-NS-Luc reporter (from Bat09, A, or B Type), three independent replicates were conducted. For each RNP, the luciferase activity with the reporter from__ the same virus (e.g., Bat-RNP and pPol1-Bat-NS-Luc) was set at 100%, and the activities with the other two reporters (e.g., pPol1-FluA-NS-Luc and pPol1-FluB-NS-Luc) were presented relative to that (FIG. 10).

The PB2, PB1, PA, and NP compatibility between Bat09 and the following influenza viruses was examined in the study (FIG. 11): A/PR/8/1934 (lab adapted human H1N1), A/Ann Arbor/6/1960 (human H2N2), A/New York/238/2005 (human H3N2); A/New York/1692/2009 (human H1N1 seasonal), A/New York/1682/2009 (human H1N1 pandemic), A/canine/New York/6977983/2010 (canine H3N8), A/turkey/Ontario/7732/1966 (avian H5N9), A/Hong Kong/213/2003 (avian H5N1), A/Anhui/1/2013 (human H7N9). B/Russia/1969 (lab adapted human IBV), and A/flat-faced bat/Peru/033/2010 (bat H18N11). For the compatibility test between Bat09 and IAVs (FIG. 11A-I), 293T cells were co-transfected with 0.2 μg each of the PB2, PB1, PA, NP (from Bat09 or LAV), 0.1 μg of pPolI-Bat-NS-Luc plasmid and 0.1 μg of pPolI-FluA-NS-Luc. For compatibility test between Bat09 and IBV (FIG. 11J), 293T cells were co-transfected with 0.2 μg each of the PB2, PB1, PA, NP (from Bat09 or B/Russia/1969), 0.1 μg of pPolI-Bat-NS-Luc plasmid and 0.1 μg of pPolI-FluB-NS-Luc. For compatibility test between Bat09 and Bat10 (FIG. 11K), 0.2 μg each of the PB2, PB1, PA, NP (from Bat09 or Bat10), and pPolI-Bat-NS-Luc plasmids were used (The NS non-coding regions of Bat09 and Bat10 have the same sequence). Renilla luciferase was also co-transfected and dual-luciferase reporter assay system was used. For each combination of PB2, PB1, PA, and NP (from Bat09 or another influenza virus), three independent replicates were conducted at 37° C., the luciferase activity of the all-Bat09-combination (Bat09-PB2/Bat09-PB1/Bat09-PA/Bat09-NP) was set at 100%, and the activities of other 15 combinations were presented relative to that.

10. Pathogenicity of PR8, Modified Bat-Influenza Virus (Bat09:mH1mN1) and PB2 Mutants A total of 98 female BALB/c mice aged 6 to 7 weeks were randomly allocated to 7 groups (14 mice/group). Six mice were intranasally inoculated with $10^3$ $TCID_{50}$ of each virus (Bat 09:mH1mN1, Bat09:mH1mN1-PB2-701D, Bat09:mH1mN1-PB2-627K701D, Bat09:mH1mN1-PB2-158G701D, Bat09:mH1mN1-PB2-158G, PR8, or MEM Mock) in 50 μL fresh MEM medium while under light anesthesia by inhalation of 4% isoflurane. To determine the virus replication in mouse lungs, three mice from each group were euthanized on both 3 and 5 day post-inoculation (dpi). Another 8 mice from each group were intranasally inoculated with $10^4$ $TCID_{50}$ of viruses in 50 μL MEM medium; all eight mice were kept to monitor body weights and clinical signs. Weights were recorded daily and general health status was observed twice daily. After the onset of disease, the general health status was observed three times daily. Severely affected mice (i.e., more than 25% body weight loss) were euthanized immediately, and the remaining mice were euthanized on 14 dpi. All control mice were intranasally inoculated with 50 μL fresh MEM (mock group), three control mice were necropsied at 3 and 5 dpi, the remaining mice were kept until the end of the animal study.

During necropsy, the right part of the lung was frozen at −80° C. for virus titration, and the left part of the lung was fixed in 10% formalin for histopathologic examination. For virus titration, the 10% lung homogenate was prepared in cold fresh MEM medium by using a Mini Bead Beater-8

(Biospec Products; 16 Bartlesville, Okla.). The homogenate was centrifuged at 6000 rpm for 5 minutes, and the supernatant was titrated by infecting MDCK cells in 96-well plates. For the histopathologic examination, lung tissues fixed in 10% phosphate-buffered formalin were processed routinely and stained with hematoxylin and eosin. The lungs were examined microscopically both for the percentage of the lung involved and for the histopathologic changes seen, including bronchiolar and alveolar epithelial necrosis, intraalveolar neutrophilic inflammation, peribronchiolar inflammation, and bronchiolar epithelial hyperplasia and atypia. For detection of virus NP antigens in lung sections on day 5 post infection, a rabbit anti-H1N1 (2009 flu pandemic) NP polyclonal antibody was used (Genscript, USA). A pathologist examined each slide in a blinded fashion.

11. Pathogenicity of Modified Bat-Influenza Viruses (Bat09: mH1mN1ss) Containing, Truncated NS1 Genes A total of 70 female BALB/c mice aged 6 to 7 weeks were randomly allocated to 5 groups (14 mice/group). To determine virus replication, six mice were intranasally inoculated with $10^4$ $TCID_{50}$ of each virus (Bat09:mH1mN1ss-NS1-WT, Bat09:mH1N1ss-NS1-73, Bat09:mH1mN1ss-NS1-128, and PR8-NS1-126) in 50 μL MEM medium while under light anesthesia by inhalation of 4% isoflurane. Three mice from each group were killed on both 3 and 5 day post-inoculation (dpi). Another 8 mice from each group were intranasally inoculated with $10^5$ $TCID_{50}$ of each virus in 50 μL MEM medium for morbidity and mortality comparison. All the other procedures are same with described previously.

12. Pathogenicity of TX98 and Modified Bat Influenza (Bat09:mH3mN2) Viruses

A total of 42 female BALB/c mice aged 6 to 7 weeks were randomly allocated to 3 groups (14 mice/group). To investigate virus replication in mice, six mice from each group were intranasally inoculated with $3\times10^4$ $TCID_{50}$ of virus or mock-inoculated with 50 μL fresh MEM medium while under light anesthesia by inhalation of 4% isoflurane. Three of six inoculated mice from each group were euthanized at 3 and 5 day post-inoculation (dpi). To evaluate viral pathogenicity in mice, the remaining eight mice from each group were intranasally inoculated with $3\times10^5$ $TCID_{50}$ of virus (Bat09:mH3mN2, and TX98) in 50 μL fresh MEM medium or mock-inoculated with 50 μL fresh MEM medium. The mice were monitored body weights and general health status daily. After the onset of disease, the general health status was observed twice per day. Severely affected mice (i.e., more than 25% body weight loss) were humanly euthanized, and the remaining mice were euthanized and bloods were collected from each mouse to isolate serum for the HI assay at 14 dpi. Sample collection and analysis, and virus titration were performed as described above.

13. Co-Infection Study for Assessment of Reassortment

To study the reassortment between Bat09:mH1mN1 and PR8 or Bat10:mH1mN1, confluent monolayer of MDCK cells in 6-well-plates were co-infected with both viruses (Bat09:mH1mN1 and PR8, or Bat09:mH1mN1 and Bat10: mH1mN1). Both modified Bat09:mH1mN1 and Bat10: mH1mN1 viruses showed similar replication kinetics in MDCK cells, whereas the PR8 replicated more efficiently than both modified viruses in MDCK cells. Therefore, for the co-infection study with PR8 and Bat09:mH1N1 viruses, the cells were infected with the PR8 at MOI of 1 and with the Bat09:mH1mN1 at MOI of 4 (a ratio of both viruses is 1:4). For the co-infection study with Bat09:mH1mN1 and Bat10:mH1mN1 viruses, the cells were infected with each virus at MOI of 1 (a ratio of both viruses is 1:1). The co-infected MDCK cells were incubated at 37° C. with 5% CO2 for 1 hour. After 1 hour of incubation, the supernatant was removed and the infected cells were washed with fresh MEM for 10 times. One mL of infection medium supplemented with 1 μg/mL TPCK-trypsin (Worthington, Lakewood, N.J.) was added on cells. The supernatant containing progeny viruses was collected at 24 hours after inoculation. Plaque assays were performed in MDCK cells to select single virus from co-infected supernatants. The purified single virus (plaque) was amplified for further analysis. To identify the origin of each gene of the purified single virus, specific RT-PCR was used to differentiate internal genes from Bat09:mH1mN1, Bat10:mH1mN1 and PR8 viruses (primers for specific RT-PCR are available upon request). The surface HA and NA genes were differentiated by sequencing HA and NA non-coding regions (packaging signals) since three parental viruses contain identical HA and NA ORF sequences and different sequences in non-coding region (it is difficult to differentiate them by RT-PCR). For the RT-PCR, RNAs were extracted from each amplified single virus using a QIAamp Viral RNA Mini Kit (Qiagen). cDNA was synthesized by using the bat universal 12 primer (SEQ ID NO:37) for the samples from the co-infection study with Bat09:mH1mN1 and Bat10: mH1mN1 viruses, and by using a mixture of an IAV universal 12 primer (SEQ ID NO:38) and the bat universal 12 primer (SEQ ID NO:37) for the samples from the co-infection study with Bat09:mH1mN1 and PR8 viruses. If the origin of internal genes determined by the specific RT-PCR was inconclusive, sequencing was performed to confirm the results from specific RT-PCR (All sequence primers are available upon request).

14. Statistical Analysis luciferase activity, virus titers, and mouse weights were analyzed by using analysis of variance (ANOVA) in GraphPad Prism version 5.0 (GraphPad software Inc, CA). One-way ANOVA with Dunnett's multiple comparison test was used to determine the significance of the differences ($P<0.05$) among different groups. For simple comparisons, Student's t test was used to examine the significance of differences observed. Error bars represent standard deviation (±SD).

Discussion

The generation of synthetic modified bat-influenza viruses (e.g., Bat09:mH1mN1) that grow to high titers in commonly used influenza virus culture substrates and mice is an important step toward understanding these novel bat-influenza viruses. The rescue of Bat09:mH1mN1 and Bat09:mH3mN2 viruses demonstrates that the putative vRNAs of Bat09 function efficiently together and are probably derived from either one virus, or a group of compatible viruses, whose PB2, PB1, PA, NP, M, and NS proteins efficiently replicate and package vRNAs in host cells commonly used to culture influenza viruses (FIG. 2). Importantly, the data also shows that the bat-influenza HA and NA were the sole determinants inhibiting Bat09 virus rescue, and that the terminal regions of HA and NA of bat-influenza viruses selected for our constructs contain cis-acting vRNA packaging signals. Although wild type bat-influenza virus (Bat09) couldn't be propagated in the human, canine, mink, avian, porcine or bat cell lines we tested, it is likely that the bat-influenza virus can infect some other cell cultures from other species and/or tissues, especially cells derived from appropriate bat species.

Our Bat09:mH1mN1 studies provide other unique insights, which can't be gleaned from non-infectious assays. For instance, non-infectious assays (interferon-β reporter assay, FIG. 6A) showed the Bat09 NS1 carboxy-terminal truncations (NS1-128 and NS1-73) were similar to the truncated PR8 NS1 (NS1-126 and NS1-73), which largely lost the ability to inhibit the host interferon response. However, mouse experiments with the replicative bat-influenza viruses revealed that the truncation of Bat09 NS1 had minimal effects on the viral pathogenesis compared to the truncation of PR8 NS1 (FIG. 7). Differences in the attenuating impact observed in the PR8-NS1 and the Bat09-NS1 truncated viruses suggests that Bat09 has novel molecular mechanisms that have evolved in the amino terminal portion of NS1 and/or other internal protein vRNAs to antagonize/evade the host innate immune response.

The PB2 of IAV plays important roles in replication, species specificity, transmission, and pathogenesis. Our analysis of bat-influenza PB2 demonstrated that it is also a virulence determinant and as anticipated conversion of mammalian-signature residues at position 701 to avian-signature (N701D) attenuated the virus, and the E158G substitution enhanced virulence. PB2-627 is one of the most studied positions differentiating avian viruses (glutamic acid) and mammalian viruses (lysine). Intriguingly, the bat-influenza PB2 has a serine at position 627, which is unlike mammalian or avian IAVs. Our data show that PB2-627S has intermediate polymerase activity compared to PB2-627E and PB2-627K in mammalian cells, suggesting an alternative evolutionary pathway that avian influenza viruses may be able to take for mammalian adaptation.

Reassortment of the segmented genomes of Orthomyxoviruses is a powerful evolutionary mechanism that is central to the success of these pathogens. Viruses within a Genus readily reassort upon co-infection of a single host cell (e.g., avian and swine IAV); whereas, viruses from a different Genus (e.g., IAV and IBV) don't reassort. The factors important for generation of reassortant progeny from two parental influenza viruses include: recognition and replication of vRNAs by parental virus RdRp, protein-protein interaction/compatibility (e.g. heterotrimeric RdRp), and vRNA-protein interactions needed for virion morphogenesis. The RNA transcription/replication promoter of each influenza vRNA segment is formed by base pairing of highly conserved nucleotides at the 5' and 3' termini, which form a partially double-stranded structure. The IAV Genus has specific nucleotide variations within the termini that distinguish it from IBV. The termini of bat-influenza vRNAs also show conserved 5' and 3' complementarity; however, they also have distinct nucleotide variation. Therefore, we used mini-genome replication studies to analyze promoter recognition and RdRp activity of various combinations of the PB1, PB2, PA subunits in combination with various NPs from IAV, IBV, or bat-influenza. The data show that the wild type RdRp most efficiently replicate their cognate vRNAs, and that both IAV and IBV RdRp have 50-60% reduction in activity with the bat-influenza mini-genome. Many PB1, PB2, PA combinations between bat-influenza and IAV/IBV dramatically reduce activity, which demonstrates protein-protein incompatibility between the RdRp subunits. Interestingly, the bat-influenza NP and IAV NP were completely compatible in the mini-genome assay, however NP reassortant viruses could not be generated (Table 2 and Table 3) suggesting that the incompatibility of NPs may also involve complicated protein-vRNA interactions.

IAVs of various subtypes can infect and reassort in bat cell lines, providing a permissive environment for them to reassort with bat-influenza viruses. However, our reassortant analysis indicates that while two divergent bat-influenzas readily reassort, bat-influenza and IAVs don't easily reassort in co-infection experiments. Reverse genetics reassortment studies showed the PB2, PB1, PA, NP, and NS vRNAs of bat-influenza don't efficiently reassort with the IAV or IBV, and provide many additional tantalizing results. For example, reassortants were not rescued from relatively compatible RdRp combinations in the mini-genome assay (e.g. Bat-PB2/PR8-PB1/PR8-PA, FIG. 11A) and demonstrate that divergent Bat09 and Bat10 can efficiently reassort with each other. The M segment is the most highly conserved gene among influenza A and B viruses. We found that the PR8-M segment could substitute for the Bat09-M segment, indicating that the M vRNAs/protein(s) of PR8 and Bat09 have enough conservation in both cis-acting packaging signals and functional domains of the proteins (M1/M2) to enable the replication of the modified Bat09 virus. In contrast, putative packaging signal swapping of the NP and NS segments didn't overcome reassortment defects suggesting that incompatibility at the protein-protein or protein-nRNA level is likely to be a critical factor inhibiting reassortment between the bat-influenza and other influenza viruses. Alternatively, one could argue that that since the vRNA packaging signals of bat-influenza NP and NS segments have not been delineated, the putative packaging regions incorporated in the Batps-PR8 constructs may not be sufficient for packaging the modified vRNAs. However, the well-defined PR8 packaging signals incorporated in our modified gene segments should be sufficient to package the corresponding bat-influenza NP and NS vRNAs (PR8ps-Bat-NP and PR8ps-Bat-NS, FIG. 3D) in the PR8 backbone. The failure to rescue the PR8ps-Bat NP or NS viruses, as well as the PR8:Bat09-M reassortant virus, strongly suggests protein-protein or protein-vRNA level incompatibility and provides a unique opportunity to better understand the functional domains of these proteins through characterizing chimeric/mosaic proteins containing motifs/domains from both viruses.

Another caveat with our bat-influenza reassortment experiments is the focus on interactions with the laboratory adapted PR8 virus, which was chosen primarily due to biosafety concerns. Reassortment between the Bat09:mH1mN1 virus and other IAVs, particularly avian viruses (e.g., H5N1, H7N9) that appear to be more compatible in the mini-genome assay (FIG. 11), are needed to fully assess reassortment potential of bat-influenza. However, based on our results from the NP reassortment and the Bat-PB2/PR8-PB1/PR8-PA reassortment experiments, the likelihood of rescuing a reassortant with RdRp components from both Bat and IAVs is very low. Finally, since the HAs and NAs of the bat influenza viruses can't be used to rescue viruses using contemporary influenza virus host substrates, we were not able to fully assess the ability of the HA or NA to reassort with other influenza viruses. However, the known bat influenza viruses (Bat09, Bat10) could pose a pandemic threat if their HA and NA acquire mutations that impart binding to canonical influenza virus receptors and rescuing the NA for neuraminidase activity, or acquisition of binding and entry through alternative human cell surface receptors.

Collectively, our experiments suggest that the bat-influenza virus is unlikely to reassort with an IAV or IBV and spread to other species even if they were to infect the same host cell. The restriction on reassortment appears to result from multiple levels of incompatibility (RNA-RNA, RNA-protein, and/or protein-protein) that are either additive or synergistic. Consequently, our data suggest that due to the extremely limited ability of genetic information exchange between bat-influenza and IAV or IBV, the International Committee on Taxonomy of Viruses could consider classifying these two bat-influenza virus lineages as a new Genus or Species within the Orthomyxoviridae.

This study also demonstrated the power of synthetic genomics in rapid characterization and risk assessment of an emerging virus, even when the virus itself is not readily cultured. The synthetic genomics/reverse genetics strategy employed provides an infinite supply of wild type bat-influenza particles that can be used to identify permissive cells or animals. The availability of our modified bat-influenza virus, opens many other avenues of investigation and discovery, including, for instance, to gain a better understanding of cis-acting signals in the vRNAs that are important in bat-influenza transcription, replication, packaging/particle morphogenesis, and to use forward genetics to elucidate viral protein-protein and/or viral protein-host protein interactions. Finally, continued study of bat-influenza viruses and integration of data from other contemporary influenza viruses is important in the elucidation of the evolutionary history of influenza viruses.

Example 2

Modified Bat Influenza Viruses are Infectious, but are Attenuated in Pigs

Figure 13:
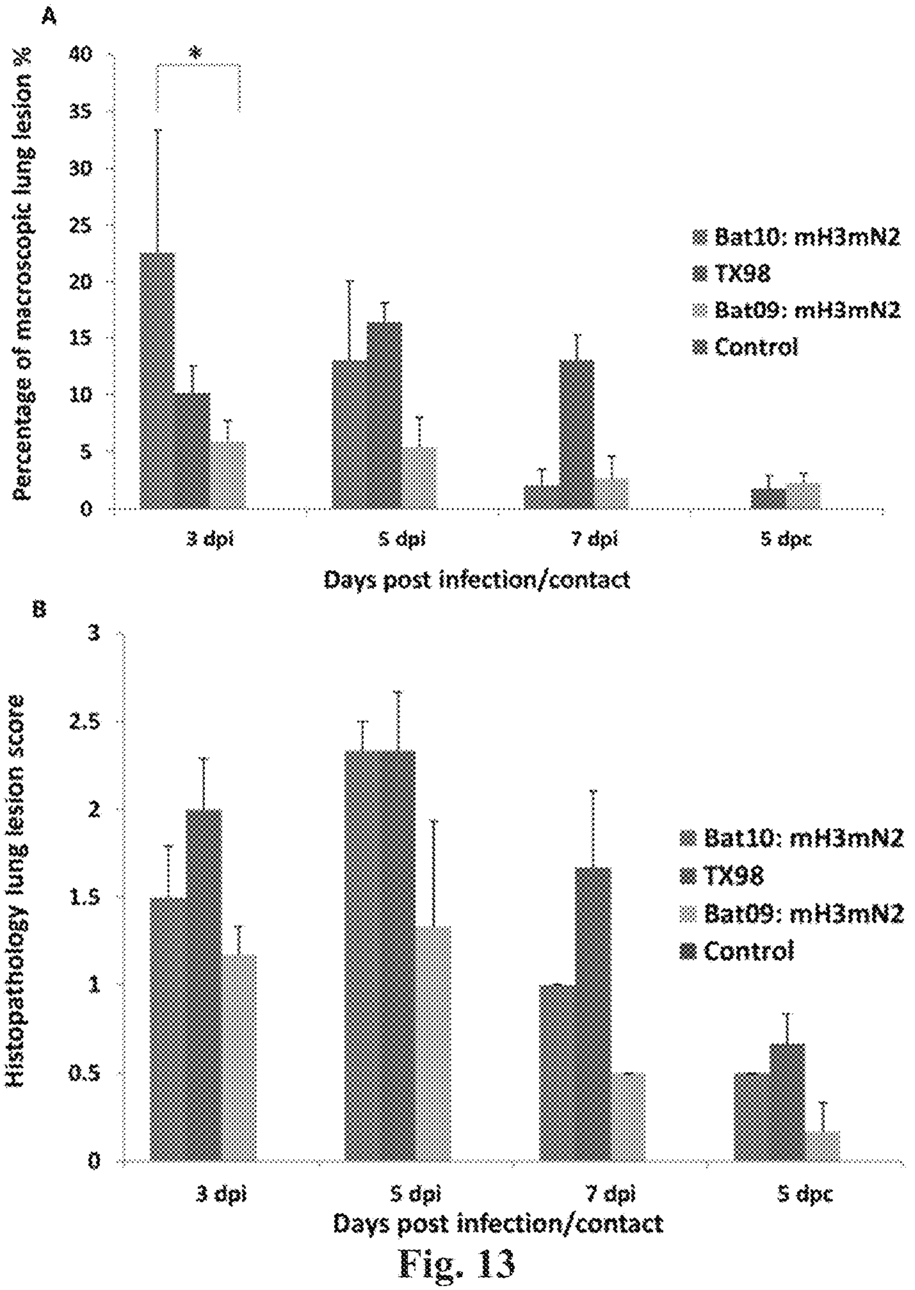
FIG. 13 shows graphs of the macroscopic and microscopic lung lesion scores of infected and contact pigs. A) Macroscopic lung lesion scores of infected pigs at 3, 5 and 7 dpi and contact pigs at 5 dpc: The lung lesion scores were counted as percentage of the lung; data indicate mean±SEM; B) Microscopic lung lesion score of infected pigs at 3, 5 and 7 dpi and contact pigs at 5 dpc. The lung lesion score is determined by the following criteria: 0=no lesion, 1=mild, 2=moderate 3=severe; data indicate mean±SEM. (* $P<0.05$;  $P<0.01$; * $P<0.001$).

Using synthetic genomics and reverse genetics, we generated two modified bat-influenza viruses (Bat09:mH3mN2 and Bat10:mH3mN2) that had the HA and NA coding regions replaced with those of A/swine/Texas/4199-2/1998 (H3N2) (TX98) and the remaining 6 internal genes from either the H17N10 A/little yellow-shouldered bat/Guatemala/164/2009 (Bat09) (SEQ ID NO:27 (HA) or 28 (NA)) or the H18N11 A/flat-faced bat/Peru/033/2010 (Bat10) virus (SEQ ID NO:25 (HA) or 26 (NA)). A group of four-week-old pigs were intratracheally infected with $5\times10^5$ $TCID_{50}$/pig of the either Bat09:mH3mN2 or Bat10:mH3mN2 or TX98 viruses. All pigs (9/9) infected with the TX98 virus showed fever that lasts for 3-4 days whereas both Bat09:mH3mN2 and Bat10:mH3mN2 only induced 6 out of 9 infected pigs fever that lasts for 1-2 days. No fever was seen in the mock-infected group. All three viruses were able to cause lung lesions of all infected pigs. The TX98 virus induced more severe lung lesions than both modified bat viruses at all tested time points (3, 5 and 7 dpi) with the exception of 3 dpi in which the Bat10:mH3mN2 caused severe lung lesions (FIG. 13A).

Figure 14:
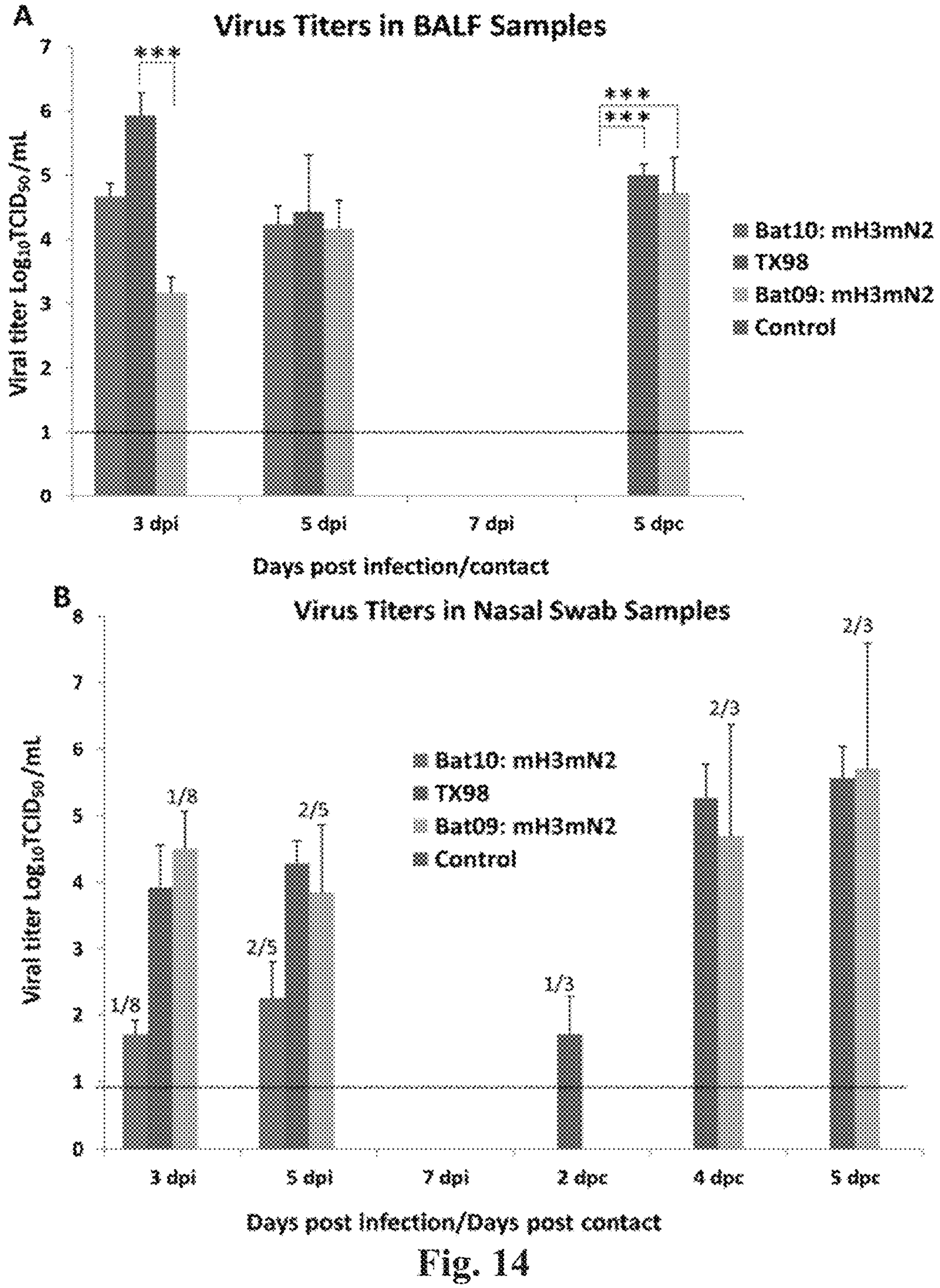
FIG. 14 shows graphs of the virus loads in BALF and nasal swabs samples of contact and principal pigs infected with wild type TX98 and modified bat influenza viruses. A)

All three viruses were able to replicate and were detected in lungs of all infected pigs at 3 and 5 dpi, no virus was detected in pigs' lungs at 7 dpi (FIG. 14A). At 3 dpi, the TX98 replicated a higher virus titer in pigs' lungs than both Bat09:mH3mN2 and Bat10:mH3mN2 viruses; but significant difference at virus titer was only observed between the TX98 and Bat09:mH3mN2 virus infection groups. All three viruses were able to induce typical microscopic lung lesions, but the wild type TX98 induced more severe lung damage in infected pigs than the two modified bat influenza viruses at early (3 dpi) and later (7 dpi) time points (FIG. 13B). All pigs infected with either modified bat influenza viruses or the wild type H3N2 virus seroconverted at day 5 and 7 post infection (Table 6).

Virus nasal shedding of both modified bat influenza viruses was detected from 1 out of 8 infected pigs at 3 dpi and from 2 out of 5 infected pigs at 5 dpi, whereas all pigs infected with the wild type TX98 virus shed virus on both days post infection (FIG. 14B). All contact pigs from three infected groups did not show obvious respiratory clinical symptoms. Fever was observed from all 3 contact pigs from both wild type TX98 and Bat10:mH3mN2 infection groups, only 1 out of 3 contact pigs displayed fever in the Bat09:mH3mN2 infection group. Macroscopic lung lesions were found in all 3 contact pigs from both wild type TX98 and Bat09:mH3mN2 infection groups; no lesions were observed from any contact pigs of the Bat10:mH3mN2 infection group (FIG. 13A). Virus was detected from lungs of all 3 contact pigs from both wild type TX98 and Bat09:mH3mN2 infection groups with a high titer of more than $10^4$ $TCID_{50}$/mL; no virus was detected from lungs of any contact pigs of the Bat10:mH3mN2 infection group (FIG. 14A). Nasal virus shedding was found in contact pigs from both wild type TX98 and Bat09:mH3mN2 infection groups, no contact pig shed virus in the Bat10:mH3mN2 infection group FIG. 14B). However, the wild type TX98 shed more efficiently than the Bat09:mH3mN2 virus, evidenced by that the wild type virus was detected in the early time point (⅓, 2 dpc) and from all contact animals (3/3) at later time points (4 and 5 dpc), whereas the Bat09:mH3mN2 virus was only detected from 2 out of 3 contact animals at late time points (4 and 5 dpc). Moderate microscopic lung lesions were observed in the wild type TX98 contact pigs, and only minimal microscopic lung lesions were observed in both Bat09:mH3mN2 and Bat10:mH3mN2 group contact pigs (FIG. 13B). All contact pigs from three infected groups seroconverted (Table 6).

In conclusion, both modified Bat09:mH3mN2 and Bat10:mH3mN2 bat viruses are infectious in pigs that seroconverted at day 5 and 7 post infection. However, both viruses are attenuated when compared with the wild type TX98 virus, evidenced by that 1) less infected pigs displayed fever; 2) less macroscopic and microscopic lung lesions in infected pigs; 3) both virus shed not efficiently in both infected and contact pigs. Furthermore, we have shown that both modified Bat09:mH3mN2 and Bat10:mH3mN2 bat viruses cannot reassort with normal influenza A viruses by reverse genetics and the co-infection assay. Taken together, all these results indicate that both modified Bat09:mH3mN2 and Bat10:mH3mN2 bat viruses can be used as live attenuated vaccines in pigs or in other species.

TABLE 6

The hemagglutination-inhibition sera titer of infected and contact pigs

| | | Infected pigs | | | | | Contact pigs | | |
|---|---|---|---|---|---|---|---|---|---|
| | | Day 5 post infection | | | Day 7 post infection | | Day 5 post contact | | |
| | Pig# | #45 | #46 | #47 | #48 | #49 | #50 | #51 | #52 |
| Bat09:mH3mN2 | HI Titer | 80 | 80 | 40 | 1280 | 40 | 640 | 40 | 40 |

TABLE 6-continued

| The hemagglutination-inhibition sera titer of infected and contact pigs | | | | | | | | | | |
|---|---|---|---|---|---|---|---|---|---|---|
| | Pig# | #10 | #11 | #12 | #13 | #14 | | #16 | #17 | #18 |
| Bat10:mH3mN2 | HI Titer | 40 | 40 | 80 | 80 | 40 | | 40 | 40 | 80 |
| | Pig# | #22 | #23 | #24 | #22 | #23 | #24 | #22 | #23 | #24 |
| TX98 | HI Titer | 80 | 40 | 40 | 640 | 640 | 640 | 40 | 40 | 40 |

The HI titer of all control pigs lowers 10

We claim:

1. A vaccine composition useful for vaccination against a target influenza strain, said composition comprising a live synthetic influenza virus dispersed in a pharmaceutically-acceptable carrier, said influenza virus comprising:

a backbone of viral segments derived from a bat influenza strain, and heterologous surface proteins HA and NA each encoded by a chimeric viral segment comprising a protein open reading frame for said HA or NA of said target influenza strain and noncoding regions and viral packaging sequences derived from said bat influenza strain, wherein said chimeric viral segment for HA is a synthetic HA construct comprising SEQ ID NO: 1 or 3, where n encodes for said protein open reading frame for HA of said target influenza strain; and/or wherein said chimerical viral segment for NA is a synthetic NA construct comprising SEQ ID NO:2 or 4, where n encodes for said protein open reading frame for NA of said target influenza strain.

2. The vaccine composition of claim 1, wherein said backbone consists of six viral segments derived from: Genbank Accession No. CY103881, Genbank Accession No. CY103882, Genbank Accession No. CY103883, Genbank Accession No. CY103885, Genbank Accession No. CY103887, and Genbank Accession No. CY103888, or functional fragments thereof.

3. The vaccine composition of claim 1, wherein said backbone consists of six viral segments derived from SEQ ID NO:5, SEQ ID NO:6, SEQ ID NO:7, SEQ ID NO:8, SEQ ID NO:10, and any one of SEQ ID NO: 13, SEQ ID NO:15, SEQ ID NO:16, or functional fragments thereof.

4. The vaccine composition of claim 1, wherein said backbone segments encode for one or more viral proteins selected from the group consisting of SEQ ID NO:9, SEQ ID NO:11, SEQ ID NO:12, SEQ ID NO:14, SEQ ID NO:39, SEQ ID NO:40, SEQ ID NO:41, SEQ ID NO:42, and functional fragments thereof.

5. The vaccine composition of claim 1, wherein said backbone consists of six viral segments derived from SEQ ID NO:17, SEQ ID NO:18, SEQ ID NO:19, SEQ ID NO:21, SEQ ID NO:23, and SEQ ID NO:24, or functional fragments thereof.

6. The vaccine composition of claim 1, wherein said backbone segments encode for one or more viral proteins selected from the group consisting of SEQ ID NO:43, SEQ ID NO:44, SEQ ID NO:45, SEQ ID NO:47, SEQ ID NO:49, SEQ ID NO:50, SEQ ID NO:51, and SEQ ID NO:52.

7. The vaccine composition of claim 1, wherein said backbone consists of six viral segments derived from: Genbank Accession No. CY125942, Genbank Accession No. CY125943, Genbank Accession No. CY125944, Genbank Accession No. CY125946, Genbank Accession No. CY125948, and Genbank Accession No. CY125949, or functional fragments thereof.

8. The vaccine composition of claim 1, wherein said virus comprises a backbone of six protein coding vRNAs for PB2, PB1, PA, NP, M, and NS derived from A/little yellow-shouldered bat/Guatemala/164/2009 (H17N10) or A/flat-faced bat/Peru/033/2010 (H18N11), and heterologous surface proteins HA and NA derived from any combination of H1-H16 and N1-N9 subtypes of influenza A viruses.

9. The vaccine composition of claim 1, said composition being useful for vaccination against a second different target influenza strain and comprising a second live synthetic influenza virus dispersed in said carrier, said second influenza virus comprising a backbone of viral segments derived from a bat influenza strain, and heterologous surface proteins HA and NA derived from said second target influenza strain.

10. The vaccine composition of claim 1, wherein composition further comprising adjuvants, active agents, preservatives, buffering agents, salts, and mixtures thereof.

11. A method of vaccinating against a target influenza strain to prevent or mitigate influenza infection in a subject, said method comprising administering a vaccine composition according to claim 1 to said subject.

12. The method of claim 11, wherein said administering comprising injecting said vaccine composition intramuscularly, subcutaneously, intradermally, or intravenously using a needle and syringe, or a needleless injection device.

13. The method of claim 11, wherein said administering comprises intranasal administration.

14. The method of claim 13, wherein said vaccine composition is administered as drops, large particle aerosol, or a spray.

15. The method of claim 11, wherein said vaccine composition is administered as a unit dosage form.

16. A kit for vaccination against a target influenza strain to prevent or mitigate influenza infection in a subject, said kit comprising:

a vaccine composition according to claim 1; and instructions for administering said vaccine composition to said subject.

17. A synthetic cDNA encoding for hemagglutinin surface protein useful for generating live influenza viruses comprising SEQ ID NO:1 or 3.

18. A synthetic cDNA encoding for neuraminidase surface protein useful for generating live influenza viruses comprising SEQ ID NO:2 or 4.

* * * * *